(12) United States Patent
Newberry et al.

(10) Patent No.: US 10,973,470 B2
(45) Date of Patent: *Apr. 13, 2021

(54) SYSTEM AND METHOD FOR SCREENING AND PREDICTION OF SEVERITY OF INFECTION

(71) Applicant: Sanmina Corporation, San Jose, CA (US)

(72) Inventors: Robert Steven Newberry, New Hope, AL (US); Matthew Rodencal, Huntsville, AL (US)

(73) Assignee: SANMINA CORPORATION, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,646

(22) Filed: Apr. 14, 2020

(65) Prior Publication Data
US 2020/0253562 A1    Aug. 13, 2020

Related U.S. Application Data

(63) Continuation-in-part of application No. 16/779,453, filed on Jan. 31, 2020, and a continuation-in-part of
(Continued)

(51) Int. Cl.
*A61B 5/1455*        (2006.01)
*A61B 5/00*           (2006.01)
(Continued)

(52) U.S. Cl.
CPC .......... *A61B 5/7275* (2013.01); *A61B 5/0002* (2013.01); *A61B 5/0022* (2013.01);
(Continued)

(58) Field of Classification Search
None
See application file for complete search history.

(56) References Cited

U.S. PATENT DOCUMENTS

| 4,913,150 A | 4/1990 | Cheung et al. |
| 5,115,133 A | 5/1992 | Knudson |

(Continued)

FOREIGN PATENT DOCUMENTS

| CN | 102609627 A   | 7/2012 |
| EP | 2017001250 A1 | 1/2017 |

(Continued)

OTHER PUBLICATIONS

Bermejo-Martin et al. "Shared features of endothelial dysfunction between sepsis and its preceding risk factors (aging and chronic disease)." J Clin Med. 7(11):400, doi:10.3390/jcm7110400 (Oct. 30, 2018).

(Continued)

*Primary Examiner* — Marjan Fardanesh
(74) *Attorney, Agent, or Firm* — Loza & Loza LLP; Jessica Smith

(57) ABSTRACT

A photoplethysmography (PPG) circuit obtains PPG signals at a plurality of wavelengths of light reflected from tissue of a user. A processing device generates parameters using the PPG signals to screen the user for an infection, such as sepsis, influenza and/or COVID-19. The processing device may also determine a severity level of the infection and a confidence level in the determination. The parameters may include a measurement of nitric oxide (NO) level, respiration rate, heart rate and/or oxygen saturation.

28 Claims, 48 Drawing Sheets

Related U.S. Application Data application No. 16/711,038, filed on Dec. 11, 2019, and a continuation-in-part of application No. 16/433,947, filed on Jun. 6, 2019, now Pat. No. 10,736,580, and a continuation-in-part of application No. 16/391,175, filed on Apr. 22, 2019, and a continuation-in-part of application No. 16/270,268, filed on Feb. 7, 2019, and a continuation-in-part of application No. 16/239,417, filed on Jan. 3, 2019, and a continuation-in-part of application No. 16/208,358, filed on Dec. 3, 2018, and a continuation-in-part of application No. 16/183,354, filed on Nov. 7, 2018, now Pat. No. 10,744,262, and a continuation-in-part of application No. 16/172,661, filed on Oct. 26, 2018, now Pat. No. 10,744,261, and a continuation-in-part of application No. 15/958,620, filed on Apr. 20, 2018, now Pat. No. 10,524,720, and a continuation-in-part of application No. 15/898,580, filed on Feb. 17, 2018, said application No. 16/208,358 is a continuation of application No. 15/859,147, filed on Dec. 29, 2017, now Pat. No. 10,194,871, said application No. 16/270,268 is a continuation of application No. 15/811,479, filed on Nov. 13, 2017, now Pat. No. 10,238,346, said application No. 16/711,038 is a continuation of application No. 15/718,721, filed on Sep. 28, 2017, now Pat. No. 10,517,515, said application No. 15/958,620 is a continuation of application No. 15/680,991, filed on Aug. 18, 2017, now Pat. No. 9,968,289, said application No. 15/718,721 is a continuation of application No. 15/622,941, filed on Jun. 14, 2017, now Pat. No. 9,788,767, said application No. 15/811,479 is a continuation-in-part of application No. 15/490,813, filed on Apr. 18, 2017, now Pat. No. 9,980,676, said application No. 16/183,354 is a continuation of application No. 15/485,816, filed on Apr. 12, 2017, now Pat. No. 10,155,087, application No. 16/848,646, which is a continuation-in-part of application No. 15/404,117, filed on Jan. 11, 2017, and a continuation-in-part of application No. 15/400,916, filed on Jan. 6, 2017, now Pat. No. 10,750,981, said application No. 15/485,816 is a continuation of application No. 15/276,760, filed on Sep. 26, 2016, now Pat. No. 9,636,457, said application No. 15/490,813 is a continuation of application No. 15/275,388, filed on Sep. 24, 2016, now Pat. No. 9,642,578, said application No. 16/391,175 is a continuation of application No. 14/866,500, filed on Sep. 25, 2015, now Pat. No. 10,321,860.

(60) Provisional application No. 62/935,589, filed on Nov. 14, 2019, provisional application No. 62/675,151, filed on May 22, 2018, provisional application No. 62/613,388, filed on Jan. 3, 2018, provisional application No. 62/577,707, filed on Oct. 26, 2017, provisional application No. 62/463,104, filed on Feb. 24, 2017, provisional application No. 62/383,313, filed on Sep. 2, 2016, provisional application No. 62/312,614, filed on Mar. 24, 2016, provisional application No. 62/307,375, filed on Mar. 11, 2016, provisional application No. 62/194,264, filed on Jul. 19, 2015.

(51) Int. Cl.
*A61B 5/145* (2006.01)
*A61B 5/01* (2006.01)
*G16H 40/63* (2018.01)
*A61B 5/024* (2006.01)

(52) U.S. Cl.
CPC ............ *A61B 5/01* (2013.01); *A61B 5/02416* (2013.01); *A61B 5/1455* (2013.01); *A61B 5/14532* (2013.01); *A61B 5/14551* (2013.01); *A61B 5/4845* (2013.01); *A61B 5/6817* (2013.01); *A61B 5/6893* (2013.01); *A61B 5/743* (2013.01); *G16H 40/63* (2018.01); *A61B 5/681* (2013.01); *A61B 5/6826* (2013.01); *A61B 5/7225* (2013.01); *A61B 2560/0223* (2013.01)

(56) References Cited

U.S. PATENT DOCUMENTS

| | | |
|---|---|---|
| 5,269,310 A | 12/1993 | Jones et al. |
| 5,358,703 A | 10/1994 | Lai |
| 5,515,847 A | 5/1996 | Braig et al. |
| 5,673,692 A | 10/1997 | Schulze et al. |
| 5,823,966 A | 10/1998 | Buchert |
| 5,891,022 A * | 4/1999 | Pologe ............... A61B 5/14552 600/310 |
| 5,947,911 A | 9/1999 | Wong et al. |
| 5,983,121 A | 11/1999 | Tsuchiya |
| 6,087,087 A | 7/2000 | Yonetani et al. |
| 6,280,390 B1 | 8/2001 | Akselrod et al. |
| 6,285,896 B1 | 9/2001 | Tobler et al. |
| 6,305,804 B1 | 10/2001 | Rice et al. |
| 6,537,225 B1 | 3/2003 | Mills |
| 6,694,180 B1 | 2/2004 | Boesen |
| 6,719,705 B2 | 4/2004 | Mills |
| 6,819,950 B2 | 11/2004 | Mills |
| 6,921,367 B2 | 7/2005 | Mills |
| 6,985,763 B2 | 1/2006 | Boas et al. |
| 7,154,592 B2 | 12/2006 | Reynolds et al. |
| 7,167,736 B2 | 1/2007 | Winther |
| 7,171,251 B2 | 1/2007 | Sarussi et al. |
| 7,179,228 B2 | 2/2007 | Banet |
| 7,209,775 B2 | 4/2007 | Bae et al. |
| 7,291,497 B2 | 11/2007 | Holmes et al. |
| 7,371,562 B2 | 5/2008 | Cunningham et al. |
| 7,608,045 B2 | 10/2009 | Mills |
| 7,647,083 B2 | 1/2010 | Al-Ali et al. |
| 7,761,127 B2 | 7/2010 | Al-Ali et al. |
| 7,763,472 B2 | 7/2010 | Doctor et al. |
| 7,764,982 B2 | 7/2010 | Dalke et al. |
| 7,941,199 B2 | 5/2011 | Kiani |
| 8,224,411 B2 | 7/2012 | Al-Ali et al. |
| 8,255,027 B2 | 8/2012 | Al-Ali et al. |
| 8,328,420 B2 | 12/2012 | Abreu |
| 8,385,996 B2 | 2/2013 | Smith et al. |
| 8,401,605 B2 | 3/2013 | Huiku |
| 8,483,787 B2 | 7/2013 | Al-Ali et al. |
| 8,494,507 B1 | 7/2013 | Tedesco et al. |
| 8,597,274 B2 | 12/2013 | Sloan et al. |
| 8,652,040 B2 | 2/2014 | Leboeuf et al. |
| 8,676,284 B2 | 3/2014 | He |
| 8,730,047 B2 | 5/2014 | Ridder et al. |
| 8,868,149 B2 | 10/2014 | Eisen et al. |
| 8,888,701 B2 | 11/2014 | Leboeuf et al. |
| 8,906,693 B2 | 12/2014 | Schultz et al. |
| 8,923,918 B2 | 12/2014 | Kreger et al. |
| 8,961,932 B2 | 2/2015 | Silverman |
| 9,022,973 B2 | 5/2015 | Sexton et al. |
| 9,131,882 B2 | 9/2015 | Al-Ali et al. |
| 9,149,216 B2 | 10/2015 | Eisen et al. |
| 9,149,646 B2 | 10/2015 | Keswarpu et al. |
| 9,387,033 B2 | 7/2016 | Yodfat et al. |
| 9,442,092 B2 | 9/2016 | Lane |
| 9,521,970 B2 | 12/2016 | Hoppe et al. |
| 9,554,738 B1 | 1/2017 | Gulati et al. |
| 9,642,578 B2 | 5/2017 | Newberry |
| 9,668,701 B2 | 6/2017 | Maarek |
| 9,713,428 B2 | 7/2017 | Chon et al. |

(56) References Cited

U.S. PATENT DOCUMENTS

| | | |
|---|---|---|
| 9,739,663 B2 | 8/2017 | Halder et al. |
| 9,820,656 B2 | 11/2017 | Olivier |
| 9,839,381 B1 | 12/2017 | Weber et al. |
| 9,924,895 B2 | 3/2018 | Rawicz et al. |
| 9,949,675 B2 | 4/2018 | Miller |
| 9,999,355 B2 | 6/2018 | Kirenko |
| 10,028,682 B2 | 7/2018 | Thiele |
| D824,937 S | 8/2018 | Sparandara et al. |
| 10,099,554 B2 | 10/2018 | Steeg et al. |
| 10,130,285 B1 | 11/2018 | Singamsetty et al. |
| 10,153,796 B2 | 12/2018 | Fung et al. |
| 10,181,021 B2 | 1/2019 | Venkatraman et al. |
| 10,206,619 B1 | 2/2019 | Lee et al. |
| 10,215,698 B2 | 2/2019 | Han et al. |
| 10,227,063 B2 | 3/2019 | Abreu |
| 10,232,156 B2 | 3/2019 | Netzel et al. |
| 10,278,591 B2 | 5/2019 | Gil |
| D850,316 S | 6/2019 | Ennis et al. |
| 10,314,500 B2 | 6/2019 | Olivier |
| 10,322,728 B1 | 6/2019 | Porikli et al. |
| 10,342,495 B2 | 7/2019 | Melkoniemi et al. |
| 10,349,847 B2 | 7/2019 | Kwon et al. |
| 10,420,470 B2 | 9/2019 | Kwon et al. |
| 10,420,491 B2 | 9/2019 | Rajan et al. |
| 10,433,726 B2 | 10/2019 | Ramesh et al. |
| 10,433,738 B2 | 10/2019 | Thomas et al. |
| 10,433,739 B2 | 10/2019 | Weekly et al. |
| 10,463,283 B2 | 11/2019 | Ferber et al. |
| 2002/0049389 A1 | 4/2002 | Abreu |
| 2003/0229276 A1 | 12/2003 | Sarussi et al. |
| 2004/0078219 A1 | 4/2004 | Kaylor et al. |
| 2004/0100376 A1 | 5/2004 | Lye et al. |
| 2004/0157341 A1 | 8/2004 | Reynolds et al. |
| 2005/0101841 A9 | 5/2005 | Kaylor et al. |
| 2005/0209516 A1 | 9/2005 | Fraden |
| 2005/0228244 A1 | 10/2005 | Banet |
| 2005/0228299 A1 | 10/2005 | Banet |
| 2005/0245831 A1 | 11/2005 | Banet |
| 2006/0009698 A1 | 1/2006 | Banet |
| 2006/0094942 A1 | 5/2006 | Winther |
| 2006/0287589 A1 | 12/2006 | Wobermin et al. |
| 2007/0202605 A1 | 8/2007 | Doctor et al. |
| 2007/0203405 A1 | 8/2007 | Shimomura |
| 2007/0260132 A1 | 11/2007 | Sterling |
| 2008/0146890 A1 | 6/2008 | Leboeuf et al. |
| 2008/0165017 A1 | 7/2008 | Schwartz |
| 2008/0208019 A1 | 8/2008 | Nitzan |
| 2008/0241199 A1 | 10/2008 | Silverman |
| 2009/0043178 A1 | 2/2009 | Belotserkovsky |
| 2009/0156988 A1 | 6/2009 | Ferren et al. |
| 2009/0187167 A1 | 7/2009 | Sexton et al. |
| 2009/0287120 A1 | 11/2009 | Ferren et al. |
| 2010/0049020 A1 | 2/2010 | Dalke et al. |
| 2010/0191080 A1 | 7/2010 | Mills |
| 2010/0274101 A1 | 10/2010 | Lin et al. |
| 2010/0331631 A1 | 12/2010 | MacLaughlin |
| 2011/0082355 A1 | 4/2011 | Eisen et al. |
| 2011/0106050 A1 | 5/2011 | Yodfat et al. |
| 2011/0137141 A1 | 6/2011 | Razoumov et al. |
| 2011/0160697 A1 | 6/2011 | Yodfat et al. |
| 2011/0166553 A1 | 7/2011 | Holmes et al. |
| 2011/0224518 A1 | 9/2011 | Tindi et al. |
| 2011/0237464 A1 | 9/2011 | Cunningham et al. |
| 2011/0275978 A1 | 11/2011 | Hyde et al. |
| 2012/0010683 A1* | 1/2012 | Keswarpu ............... A61N 5/06 607/88 |
| 2012/0029363 A1 | 2/2012 | Lund |
| 2012/0095302 A1 | 4/2012 | Adhikari |
| 2012/0131507 A1 | 5/2012 | Sparandara et al. |
| 2012/0136054 A1 | 5/2012 | Schultz et al. |
| 2012/0156933 A1 | 6/2012 | Kreger et al. |
| 2012/0203077 A1 | 8/2012 | He et al. |
| 2012/0238844 A1 | 9/2012 | Grata et al. |
| 2012/0330126 A1 | 12/2012 | Hoppe et al. |
| 2013/0030259 A1 | 1/2013 | Thomsen et al. |
| 2013/0060098 A1 | 3/2013 | Thomsen et al. |
| 2013/0066176 A1 | 3/2013 | Addison et al. |
| 2013/0110311 A1 | 5/2013 | Ver Steeg et al. |
| 2013/0310669 A1 | 11/2013 | Nitzan |
| 2014/0046160 A1 | 2/2014 | Terashima et al. |
| 2014/0100432 A1 | 4/2014 | Golda et al. |
| 2014/0112940 A1 | 4/2014 | Lane |
| 2014/0194342 A1 | 7/2014 | Zhang et al. |
| 2014/0243648 A1 | 8/2014 | Dubielczyk |
| 2014/0253709 A1 | 9/2014 | Bresch et al. |
| 2014/0275852 A1 | 9/2014 | Hong et al. |
| 2014/0297313 A1 | 10/2014 | Condurso et al. |
| 2014/0316226 A1 | 10/2014 | Ferber et al. |
| 2015/0066238 A1 | 3/2015 | Todd et al. |
| 2015/0088007 A1 | 3/2015 | Bardy et al. |
| 2015/0094914 A1 | 4/2015 | Abreu |
| 2015/0105638 A1 | 4/2015 | Eisen et al. |
| 2015/0109617 A1 | 4/2015 | Gilbert et al. |
| 2015/0148622 A1 | 5/2015 | Moyer et al. |
| 2015/0148635 A1 | 5/2015 | Benaron |
| 2015/0150453 A1 | 6/2015 | Abreu |
| 2015/0182172 A1 | 7/2015 | Shelley et al. |
| 2015/0229341 A1 | 8/2015 | Fung et al. |
| 2015/0250404 A1 | 9/2015 | Maarek |
| 2015/0282747 A1 | 10/2015 | Thiele |
| 2015/0366471 A1 | 12/2015 | Leboeuf et al. |
| 2016/0018257 A1 | 1/2016 | Mirov et al. |
| 2016/0058308 A1 | 3/2016 | Robinson |
| 2016/0058347 A1 | 3/2016 | Reichgott et al. |
| 2016/0066863 A1 | 3/2016 | Thaveeprungsrporn et al. |
| 2016/0100781 A1 | 4/2016 | Bechtel et al. |
| 2016/0262707 A1 | 9/2016 | Devries |
| 2016/0367154 A1 | 12/2016 | Gladshtein et al. |
| 2017/0027521 A1 | 2/2017 | Geva et al. |
| 2017/0050518 A1 | 2/2017 | Steeg et al. |
| 2017/0071550 A1 | 3/2017 | Newberry |
| 2017/0091436 A1 | 3/2017 | Cao et al. |
| 2017/0172477 A1 | 6/2017 | Adusumilli et al. |
| 2017/0215811 A1 | 8/2017 | Newberry |
| 2017/0256110 A1 | 9/2017 | Divincent et al. |
| 2017/0347894 A1 | 12/2017 | Bhushan et al. |
| 2017/0347899 A1 | 12/2017 | Bhushan et al. |
| 2018/0117291 A1 | 5/2018 | Netzel et al. |
| 2018/0140210 A1 | 5/2018 | Jelfs et al. |
| 2018/0140237 A1 | 5/2018 | Rajan et al. |
| 2018/0177416 A1 | 6/2018 | Church et al. |
| 2018/0177440 A1 | 6/2018 | Jelfs et al. |
| 2018/0200433 A1 | 7/2018 | Cirit |
| 2018/0264242 A1 | 9/2018 | Hoffman et al. |
| 2018/0353137 A1 | 12/2018 | Balajadia et al. |
| 2018/0358119 A1 | 12/2018 | Bhushan et al. |
| 2019/0046039 A1 | 2/2019 | Ramesh et al. |
| 2019/0050622 A1 | 2/2019 | Cabibihan et al. |
| 2019/0086331 A1 | 3/2019 | Han |
| 2019/0099114 A1 | 4/2019 | Mouradian et al. |
| 2019/0110745 A1 | 4/2019 | Linnes et al. |
| 2019/0125963 A1 | 5/2019 | Mou et al. |
| 2019/0125964 A1 | 5/2019 | Mou et al. |
| 2019/0133471 A1 | 5/2019 | Olson et al. |
| 2019/0192085 A1 | 6/2019 | Krishna et al. |
| 2019/0192086 A1 | 6/2019 | Krishna et al. |
| 2019/0251238 A1 | 8/2019 | Venkatraman et al. |
| 2019/0358387 A1 | 11/2019 | Elbadry et al. |

FOREIGN PATENT DOCUMENTS

| | | |
|---|---|---|
| EP | 3488776 A1 | 5/2019 |
| WO | 2004047630 A1 | 6/2004 |
| WO | 2007013054 A1 | 2/2007 |
| WO | 2008006150 A1 | 1/2008 |
| WO | 2010128852 A3 | 11/2010 |
| WO | 2010147968 A1 | 12/2010 |
| WO | 2012108895 A1 | 8/2012 |
| WO | 2013052318 A1 | 4/2013 |
| WO | 2013127564 A1 | 9/2013 |
| WO | 2014163583 A1 | 10/2014 |
| WO | 2015143197 A1 | 9/2015 |
| WO | 2015200148 A1 | 12/2015 |
| WO | 2017001249 A1 | 1/2017 |

(56) References Cited

FOREIGN PATENT DOCUMENTS

| WO | 2018206875 A1 | 11/2018 |
|---|---|---|
| WO | 2019030700 A1 | 2/2019 |
| WO | 2019118053 A1 | 6/2019 |

OTHER PUBLICATIONS

Jacques. "Optical properties of biological tissues: a review." Phys. Med. Biol. 58 (Jun. 27, 2013).

Khalid et al. "Blood pressure estimation using photoplethysmography only: comparison between different machine learning approaches." Hindawi, J Healthc Eng. 1548647, doi:10.1155/2018/1548647 (Oct. 23, 2018).

Titheradge. "Nitric oxide in septic shock." Biochimica et Biophysica Acta 1411, 437-455 (1999).

Ferrer et al. "Empiric antibiotic treatment reduces mortality in severe sepsis and septic shock from the first hour: results from a guideline-based performance improvement program." Critical Care Medicine 42:1749-1755 (2014).

Giamarellos-Bourboulis et al. "Complex immune dysregulation in COVID-19 patients with severe respiratory failure." Cell Host Microbe. doi: 10.1016/j.chom.2020.04.009 (Jun. 10, 2020).

Ince et al. "The endothelium in sepsis." Shock 45(3): 259-270, doi:10.1097/SHK.0000000000000473 (Mar. 2016).

Kumar et al. "Duration of hypotension before initiation of effective antimicrobial therapy is the critical determinant of survival in human septic shock." Crit Care Med 34:6 1589-1596 (2006).

Mayor-Ibarguren et al. "Cutaneous small vessel vasculitis secondary to COVID-19 infection: A case report." J Eur Acad Dermatol Venereol, doi: 10.1111/jdv.16670 (2020).

Menter et al. "Post-mortem examination of COVID19 patients reveals diffuse alveolar damage with severe capillary congestion and variegated findings of lungs and other organs suggesting vascular dysfunction." Histopathology, doi: 10.1111/his.14134 (2020).

Pons et al. "Immune consequences of endothelial cells' activation and dysfunction during sepsis." Crit Care Clin. 36: 401-13 (2020).

Pruinelli et al. "Delay within the 3-hour surviving sepsis campaign guideline on mortality for patients with severe sepsis and septic shock." Crit Care Med 46: 500-5 (2018).

Rudd et al. "Global, regional, and national sepsis incidence and mortality, 1990-2017: analysis for the Global Burden of Disease Study." Lancet 395: 200-11 (2020).

Sinapidis et al. "Progression into sepsis: an individualized process varying by the interaction of comorbidities with the underlying infection." BMC Infect Dis.18: 242 (2018).

Singer et al. "The Third International Consensus Definitions for Sepsis and Septic Shock (Sepsis-3)." JAMA 315: 801-10 (2016).

* cited by examiner

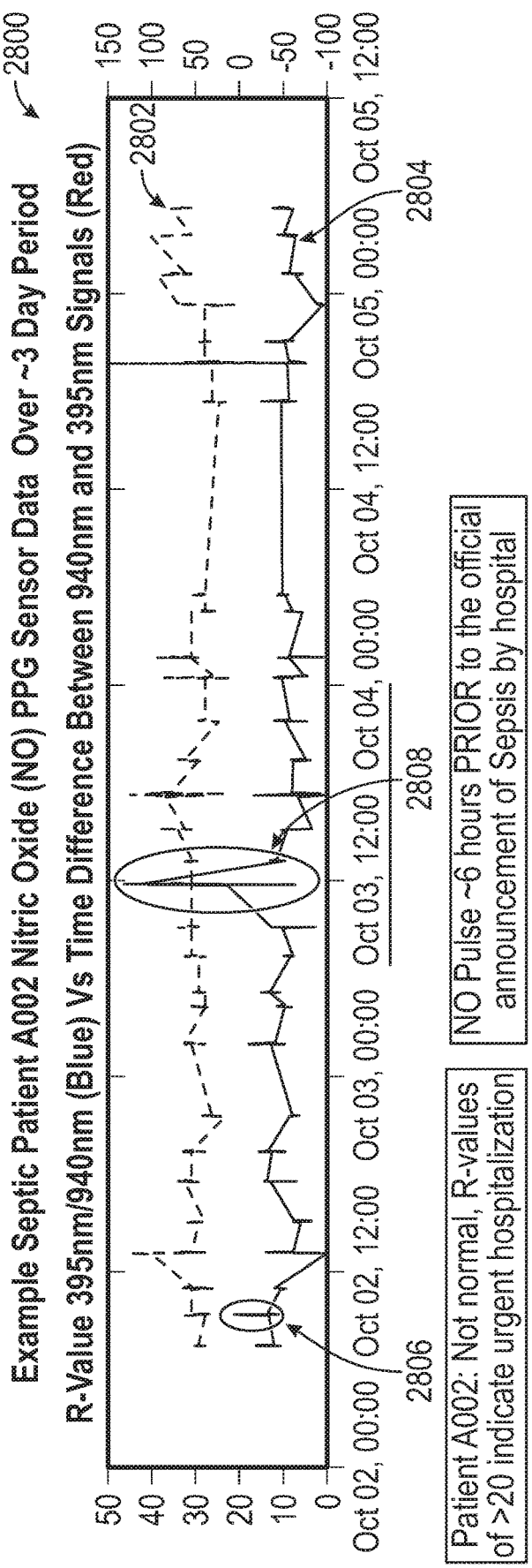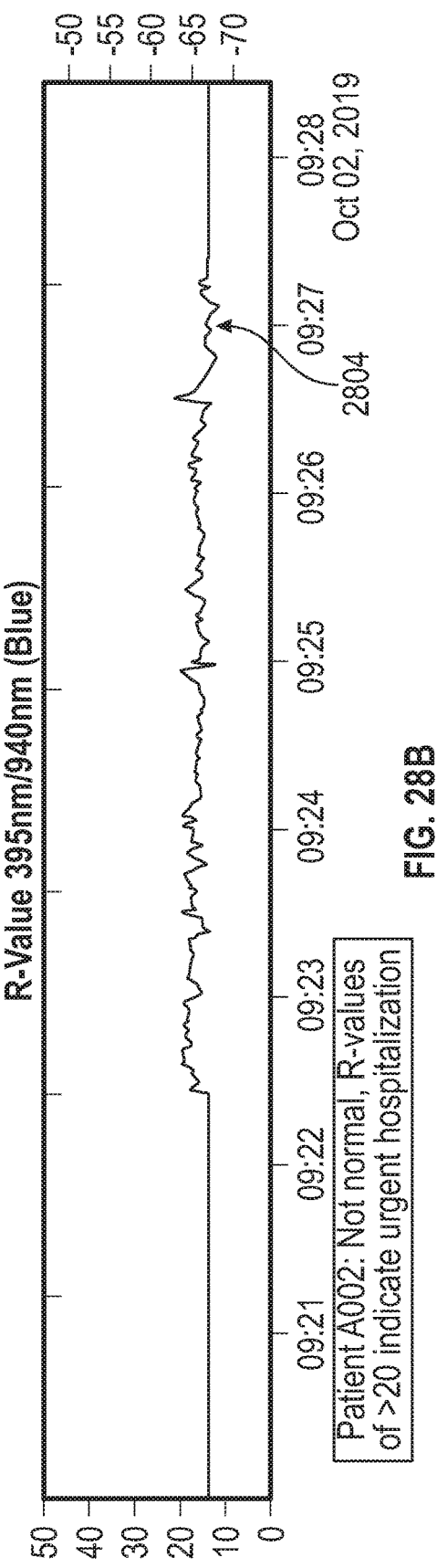
FIG. 28A
FIG. 28B

Immune Severity Scale for UV/IR R Values

- 1-10 Healthy
- 12 < 20 Sick
- >20 Acute/ICU

Blood NO Serum umol/L

~20
20 < 90
30 < 180

Sanmina Sensor

Blood Plasma

FIG. 38

| Use-Case | Current State | Method with Biosensor |
|---|---|---|
| COVID-19 Screening (Public and Health Care Workers) | Method: Nasopharyngeal swab AND oropharyngeal swab (either separately or combined), nasopharyngeal aspirate, endotracheal aspirate, BAL or sputum. Time To Result: 1-5 days dependent on health service capacity, work-load and prioritization | Method: Biosensor screens for COVID-19 in Patients Time To Result: 5 minutes |
| Hospital Patient Monitoring (PRE-ICU) | Method: Monitor worsening symptoms after presentation to hospital in patient and requirement for fever control medication and oxygen therapy Time to Result: Severity assessment is dependent on clinical progression of symptoms of the disease in patient over time from first presentation | Method: Biosensor monitors patient to assist in determining severity Time to Result: 5 minutes |
| Clinical assessment of severity of expression of immune system response to SARS-CoV-2 virus for hospitalisation | | |
| Nursing Homes | Method: Monitor patient for severe infection/sepsis according to hospital protocol on sepsis pathway and organ dysfunction / septic shock Time to Result: 2-8 hours after early onset of Sepsis | Method: Monitor patient for severe infection/sepsis according to hospital sepsis pathway protocol AND COVID-19 Finger Sensor Time to Result: 2-8 hours before standard clinical pathway determines early onset of Sepsis |

SYSTEM AND METHOD FOR SCREENING AND PREDICTION OF SEVERITY OF INFECTION

CROSS-REFERENCE TO RELATED APPLICATIONS

This application claims priority under 35 U.S.C. § 120 as a continuation-in-part of U.S. patent application Ser. No. 16/779,453 entitled "SYSTEM AND METHOD OF A BIOSENSOR FOR DETECTION OF HEALTH PARAMETERS," filed Jan. 31, 2020, and hereby expressly incorporated by reference herein, which claims priority under 35 U.S.C. § 119 to U.S. Provisional Application No. 62/935,589 entitled "SYSTEM AND METHOD OF A BIOSENSOR FOR DETECTION OF HEALTH PARAMETERS," filed Nov. 14, 2019, and hereby expressly incorporated by reference herein.

The present application claims priority under 35 U.S.C. § 120 as a continuation-in-part of U.S. patent application Ser. No. 16/433,947 entitled "SYSTEM AND METHOD OF A BIOSENSOR FOR DETECTION OF MICROVASCULAR RESPONSES," filed Jun. 6, 2019, and hereby expressly incorporated by reference herein.

The present application claims priority under 35 U.S.C. § 120 as a continuation-in-part of U.S. patent application Ser. No. 16/172,661 entitled "SYSTEM AND METHOD OF A BIOSENSOR FOR DETECTION OF VASODILATION," filed Oct. 26, 2018, and hereby expressly incorporated by reference herein, which claims priority under 35 U.S.C. § 119(e) to:

U.S. Provisional Application No. 62/675,151 entitled "SYSTEM AND METHOD OF A BIOSENSOR FOR DETECTION OF VASODILATION," filed May 22, 2018, and hereby expressly incorporated by reference herein;

U.S. Provisional Application No. 62/577,707 entitled "SYSTEM AND METHOD FOR HEALTH MONITORING OF AN ANIMAL USING A MULTI-BAND BIOSENSOR," filed Oct. 26, 2017, and hereby expressly incorporated by reference herein; and U.S. Provisional Application No. 62/613,388 entitled "SYSTEM AND METHOD FOR INFECTION DISCRIMINATION USING PPG TECHNOLOGY," filed Jan. 3, 2018, and hereby expressly incorporated by reference herein.

The present application claims priority under 35 U.S.C. § 120 as a continuation-in-part of U.S. patent application Ser. No. 15/898,580 entitled "SYSTEM AND METHOD FOR OBTAINING HEALTH DATA USING A NEURAL NETWORK," filed Feb. 17, 2018, and hereby expressly incorporated by reference herein.

The present application claims priority under 35 U.S.C. § 120 as a continuation-in-part of U.S. patent application Ser. No. 16/239,417 entitled "SYSTEM AND METHOD FOR MONITORING BLOOD CELL LEVELS IN BLOOD FLOW USING PPG TECHNOLOGY," filed Jan. 3, 2019, and hereby expressly incorporated by reference herein, which claims priority under 35 U.S.C. § 119(e) to U.S. Provisional Application No. 62/613,388 entitled "SYSTEM AND METHOD FOR INFECTION DISCRIMINATION USING PPG TECHNOLOGY," filed Jan. 3, 2018, and hereby expressly incorporated by reference herein.

The present application claims priority under 35 U.S.C. § 120 as a continuation-in-part of U.S. patent application Ser. No. 16/208,358 entitled "VEHICLULAR HEALTH MONITORING SYSTEM AND METHOD," filed Dec. 3, 2018 which claims priority as a continuation to U.S. patent application Ser. No. 15/859,147 entitled "VEHICLULAR HEALTH MONITORING SYSTEM AND METHOD," filed Dec. 29, 2017, now U.S. Pat. No. 10,194,871 issued Feb. 5, 2019 and both of which are hereby expressly incorporated by reference herein.

The present application claims priority under 35 U.S.C. § 120 as a continuation-in-part application to U.S. Utility application Ser. No. 15/958,620 entitled "SYSTEM AND METHOD FOR DETECTING A HEALTH CONDITION USING AN OPTICAL SENSOR," filed Apr. 20, 2018, now U.S. Pat. No. 10,524,720 issued Jan. 7, 2020 and hereby expressly incorporated by reference herein which claims priority under 35 U.S.C. § 120 as a continuation application to U.S. Utility application Ser. No. 15/680,991 entitled "SYSTEM AND METHOD FOR DETECTING A SEPSIS CONDITION," filed Aug. 18, 2017, now U.S. Pat. No. 9,968,289 issued May 15, 2018 and hereby expressly incorporated by reference herein.

The present application claims priority under 35 U.S.C. § 120 as a continuation-in-part application to U.S. patent application Ser. No. 16/711,038 entitled "SYSTEM AND METHOD FOR MONITORING NITRIC OXIDE LEVELS USING A NON-INVASIVE, MULTI-BAND BIOSENSOR," filed Dec. 11, 2019 and hereby expressly incorporated by reference herein, which claims priority under 35 U.S.C. § 120 as a continuation to U.S. patent application Ser. No. 15/718,721 entitled "SYSTEM AND METHOD FOR MONITORING NITRIC OXIDE LEVELS USING A NON-INVASIVE, MULTI-BAND BIOSENSOR," filed Sep. 28, 2017, now U.S. patent Ser. No. 10/517,515 issued Dec. 31, 2019 and hereby expressly incorporated by reference herein, which claims priority as a continuation application to U.S. Utility application Ser. No. 15/622,941 entitled "SYSTEM AND METHOD FOR MONITORING NITRIC OXIDE LEVELS USING A NON-INVASIVE, MULTI-BAND BIOSENSOR," filed Jun. 14, 2017, now U.S. Pat. No. 9,788,767 issued Oct. 17, 2017, and hereby expressly incorporated by reference herein, which claims priority under 35 U.S.C. § 119 to U.S. Provisional Application No. 62/463,104 entitled "SYSTEM AND METHOD FOR MONITORING NITRIC OXIDE LEVELS USING A NON-INVASIVE, MULTI-BAND BIOSENSOR," filed Feb. 24, 2017, and hereby expressly incorporated by reference herein.

The present application claims priority under 35 U.S.C. § 120 as a continuation-in-part application to U.S. patent application Ser. No. 15/404,117 entitled "SYSTEM AND METHOD FOR HEALTH MONITORING INCLUDING A USER DEVICE AND BIOSENSOR," filed Jan. 11, 2017 and hereby expressly incorporated by reference herein.

The present application claims priority under 35 U.S.C. § 120 as a continuation-in-part application to U.S. patent application Ser. No. 16/183,354 entitled "SYSTEM AND METHOD FOR HEALTH MONITORING BY AN EAR PIECE," filed Nov. 7, 2018 and hereby expressly incorporated by reference herein, which claims priority under 35 U.S.C. § 120 as a continuation application to U.S. patent application Ser. No. 15/485,816 entitled "SYSTEM AND METHOD FOR A DRUG DELIVERY AND BIOSENSOR PATCH," filed Apr. 12, 2017, now U.S. Pat. No. 10,155,087 issued Dec. 18, 2018 and hereby expressly incorporated by reference herein, which claims priority under 35 U.S.C. § 120 as a continuation application to U.S. Utility application Ser. No. 15/276,760, entitled "SYSTEM AND METHOD FOR A DRUG DELIVERY AND BIOSENSOR PATCH," filed Sep. 26, 2016, now U.S. Pat. No. 9,636,457 issued May 2, 2017, which is hereby expressly incorporated by reference herein, which claims priority under 35 U.S.C. § 119 to U.S. Provisional Application No. 62/383,313 entitled "SYSTEM AND METHOD FOR A DRUG DELIVERY AND BIOSENSOR PATCH," filed Sep. 2, 2016, and hereby expressly incorporated by reference herein.

The present application claims priority under 35 U.S.C. § 120 as a continuation-in-part of U.S. patent application Ser. No. 16/270,268 entitled "SYSTEM AND METHOD FOR A BIOSENSOR INTEGRATED IN A VEHICLE," filed Feb. 7, 2019, and hereby expressly incorporated by reference herein which claims priority under 35 U.S.C. § 120 as a continuation application to U.S. patent application Ser. No. 15/811,479 entitled "SYSTEM AND METHOD FOR A BIOSENSOR INTEGRATED IN A VEHICLE," filed Nov. 13, 2017, now U.S. Pat. No. 10,238,346 issued Mar. 26, 2019 and hereby expressly incorporated by reference herein, which claims priority under 35 U.S.C. § 120 as a continuation-in-part application to U.S. patent application Ser. No. 15/490,813 entitled "SYSTEM AND METHOD FOR HEALTH MONITORING USING A NON-INVASIVE, MULTI-BAND BIOSENSOR," filed Apr. 18, 2017, now U.S. Pat. No. 9,980,676 issued May 29, 2018 which claims priority under 35 U.S.C. § 120 as a continuation application to U.S. patent application Ser. No. 15/275,388 entitled "SYSTEM AND METHOD FOR HEALTH MONITORING USING A NON-INVASIVE, MULTI-BAND BIOSENSOR," filed Sep. 24, 2016, now U.S. Pat. No. 9,642,578 issued May 9, 2017, which claimed priority under 35 U.S.C. § 119 to:

- U.S. Provisional Application No. 62/307,375 entitled "SYSTEM AND METHOD FOR HEALTH MONITORING USING A NON-INVASIVE, MULTI-BAND BIOSENSOR," filed Mar. 11, 2016, and hereby expressly incorporated by reference herein; and
- U.S. Provisional Application No. 62/312,614 entitled "SYSTEM AND METHOD FOR DETERMINING BIOSENSOR DATA USING A BROAD SPECTRUM LIGHT SOURCE," filed Mar. 24, 2016, and hereby expressly incorporated by reference herein.

The present application claims priority under 35 U.S.C. § 120 as a continuation-in-part application to U.S. patent application Ser. No. 15/400,916 entitled "SYSTEM AND METHOD FOR HEALTH MONITORING INCLUDING A REMOTE DEVICE," filed Jan. 6, 2017 and hereby expressly incorporated by reference herein.

The present application claims priority under 35 U.S.C. § 120 as a continuation-in-part of U.S. patent application Ser. No. 16/391,175 entitled "SYSTEM AND METHOD FOR GLUCOSE MONITORING," filed Apr. 22, 2019 which claims priority under 35 U.S.C. § 120 as a continuation application to U.S. patent application Ser. No. 14/866,500 entitled "SYSTEM AND METHOD FOR GLUCOSE MONITORING," filed Sep. 25, 2015, now U.S. patent Ser. No. 10/321,860 on Jun. 18, 2019, and hereby expressly incorporated by reference herein, which claims priority under 35 U.S.C. § 119(e) to U.S. Provisional Application No. 62/194,264 entitled "SYSTEM AND METHOD FOR GLUCOSE MONITORING," filed Jul. 19, 2015, and both of which are hereby expressly incorporated by reference herein.

FIELD

This application relates to a system and methods of non-invasive, autonomous health monitoring, and in particular, a system and method for health monitoring to detect a sepsis condition in a patient.

BACKGROUND

Various invasive methods have been developed for measurement of nitric oxide (NO) levels using one or more types of techniques to remove cells from various types of bodily fluids. The methods usually require drawing blood from a blood vessel using a needle and syringe. The blood sample is then transported to a lab for analysis to determine NO levels using physical or chemical measurements. For example, in one current method, a blood sample is inserted into a semi-permeable vessel including an NO reacting substance that traps NO diffusing thereinto. A physical or chemical detection method is then used to measure the levels of NO in the blood sample.

These known in vitro measurements of NO levels have disadvantages. The process of obtaining blood samples is time consuming, inconvenient and painful to a patient. It may also disrupt sleep of the patient. The measurements of the NO levels are not continuous and may only be updated by taking another blood sample.

One current non-invasive method is known for measuring oxygen saturation in blood vessels using pulse oximeters. Pulse oximeters detect oxygen saturation of hemoglobin by using, e.g., spectrophotometry to determine spectral absorbencies and determining concentration levels of oxygen based on Beer-Lambert law principles. In addition, pulse oximetry may use photoplethysmography (PPG) methods for the assessment of oxygen saturation in pulsatile arterial blood flow. The subject's skin at a 'measurement location' is illuminated with two distinct wavelengths of light and the relative absorbance at each of the wavelengths is determined. For example, a wavelength in the visible red spectrum (for example, at 660 nm) has an extinction coefficient of hemoglobin that exceeds the extinction coefficient of oxihemoglobin. At a wavelength in the near infrared spectrum (for example, at 940 nm), the extinction coefficient of oxihemoglobin exceeds the extinction coefficient of hemoglobin. The pulse oximeter filters the absorbance of the pulsatile fraction of the blood, i.e. that due to arterial blood (AC components), from the constant absorbance by nonpulsatile venous or capillary blood and other tissue pigments (DC components), to eliminate the effect of tissue absorbance to measure the oxygen saturation of arterial blood.

A practical application of this technique is pulse oximetry, which utilizes a noninvasive sensor to measure oxygen saturation ($SpO_2$) and pulse rate and can output representative photoplethysmographic waveforms. Such PPG techniques are heretofore been limited to determining oxygen saturation using wavelengths in the infrared spectrum.

As such, there is a need for a patient monitoring system and method that includes a non-invasive biosensor configured to monitor concentration levels of nitric oxide (NO) in blood flow in vivo for screening and predicting severity of an infection, such as sepsis or viral infections.

SUMMARY

In one aspect, a biosensor includes a photoplethysmography (PPG) circuit configured to obtain at least a first PPG signal from light reflected from skin tissue of a patient, wherein the light includes a first wavelength in an ultraviolet (UV) range, and a processing circuit configured to obtain a measurement of nitric oxide (NO) using the first PPG signal and generate an indication of infection in the patient using the measurement of NO.

In another aspect, a biosensor includes an optical circuit configured to obtain at least a first PPG signal from light reflected from skin tissue of a patient, wherein the light includes a first wavelength in an ultraviolet (UV) range and at least a second PPG signal from light reflected from skin tissue of the patient, wherein the light includes a second wavelength in an infrared (IR) range. The biosensor further includes a processing circuit configured to obtain a measurement of nitric oxide (NO) levels in blood flow using the first PPG signal and the second PPG signal, wherein the measurement of NO levels is an R value determined using the first PPG signal and the second PPG signal; generate an indication of infection in the patient using at least the measurement of NO levels; and generate a severity level of the infection using at least the measurement of NO levels.

In one or more of the above aspects, the processing circuit is further configured to generate a severity level of the infection in the patient.

In one or more of the above aspects, the processing circuit is further configured to determine a heart rate and respiration of the patient using the first PPG signal and generate the indication of the risk of infection in the patient using the measurement of NO and the heart rate and the respiration rate.

In one or more of the above aspects, the biosensor further includes a temperature sensor configured to measure a skin temperature of the patient. The processing circuit is further configured to generate the indication of the risk of infection in the patient using the measurement of NO and the skin temperature of the patient.

In one or more of the above aspects, the optical circuit is configured to obtain a plurality of additional PPG signals at a plurality of different wavelengths reflected from tissue of a user, wherein the plurality of different wavelengths have varying penetration depths of tissue.

In one or more of the above aspects, the processing circuit is further configured to determine a plurality of L values using the first PPG signal and the plurality of additional PPG signals; determine a plurality of R values using the plurality of L values; and generate the indication of the infection in the patient using the plurality of L values and the plurality of R values.

In one or more of the above aspects, the processing circuit is further configured to determine one or more other PPG parameters using the first PPG signal and the plurality of additional PPG signals and generate the indication of the risk of infection in the patient using the plurality of L values, the plurality of R values and the one or more other PPG parameters.

In one or more of the above aspects, the processing circuit is the one or more other PPG parameters include at least one of: a phase delay between the first PPG signal and a second PPG signal of the plurality of additional PPG signals, a correlation of phase shape between the first PPG signal and the second PPG signal or a periodicity of first PPG signal or the second PPG signal, a pulse pressure (amplitude of the cardiac cycle).

In one or more of the above aspects, the processing circuit is configured to determine a confidence level in the indication of infection in the patient using the plurality of L values, the plurality of R values and the one or more other PPG parameters.

In one or more of the above aspects, the processing circuit is further configured to determine a type of the infection using the plurality of L values, the plurality of R values and the one or more other PPG parameters, wherein the type of infection includes at least one of: sepsis, COVID-19, pneumonia, or influenza.

In one or more of the above aspects, the plurality of L values includes: a first L value determined using the first PPG signal obtained at the first wavelength in a range of 380 nm -410 nm; and a second L value determined using a second PPG signal of the plurality of additional PPG signals, wherein the second PPG signal is obtained at a second wavelength equal to or above 660 nm.

In one or more of the above aspects, the plurality of R values includes an R value determined using the first PPG signal obtained at the first wavelength in a range of 380 nm -410 nm and the second PPG signal obtained at the second wavelength equal to or above 660 nm; an R value determined using the first PPG signal obtained at the first wavelength in the range of 380 nm-410 nm and a third PPG signal of the plurality of additional PPG signals, wherein the third PPG signal is obtained at a third wavelength in a range of 510 nm-550 nm; or an R value determined using the third PPG signal obtained at the third wavelength in the range of 510 nm -550 nm and the second PPG signal obtained at the second wavelength equal to or above 660 nm.

In one or more of the above aspects, the processing circuit includes a neural network processing circuit, wherein the neural network processing device is pre-configured with a learning vector generated from a training set, wherein the training set includes the plurality of L values, the plurality of R values and the one or more other PPG parameters from a plurality of patients with the infection.

In one or more of the above aspects, the processing circuit is further configured to determine a respiratory rate from the first or second PPG signals; determine an estimation of blood pressure from the first or second PPG signals; and determine a hybrid quick Sequential Organ Failure Assessment (qSOFA) score using the respiratory rate, the measurement of NO levels and the estimation of blood pressure.

In one or more of the above aspects, the processing circuit is further configured to determine a heart rate and respiration of the patient using one or more of the first PPG signal or the second PPG signal and generate the indication of the risk of infection in the patient using the measurement of NO, the heart rate and the respiration rate.

In one or more of the above aspects, the biosensor includes a temperature sensor configured to measure a skin temperature of the patient and wherein the processing circuit is further configured to generate the indication of the risk of infection in the patient using the measurement of NO, the heart rate, the respiration rate and the skin temperature of the patient.

In one or more of the above aspects, the processing circuit is further configured to determine the R value using the first PPG signal obtained at the first wavelength in a range of 380 nm-400 nm and the second PPG signal obtained at the second wavelength equal to or above 660 nm and generate the indication of the infection in the patient using the R value.

In one or more of the above aspects, the processing circuit is further configured to determine a second R value using a third PPG signal obtained at a third wavelength in the range of 510 nm and 550 nm and the second PPG signal obtained at the second wavelength equal to or above 660 nm, wherein the second R value is a measurement of creatinine in blood flow and generate the indication of the infection in the patient using the first R value for the measurement of NO levels in blood flow and the second R value for the measurement of creatinine in blood flow.

In one or more of the above aspects, the processing circuit is further configured to determine a third R value using a fourth PPG signal obtained at a fourth wavelength in the range of 448 nm and 488 nm and the second PPG signal obtained at the second wavelength equal to or above 660 nm, wherein the third R value is a measurement of a liver enzyme P450 in blood flow and generate the indication of the infection in the patient using the first R value for the measurement of NO levels in blood flow, the second R value for the measurement of creatinine in blood flow and the third R value for the measurement of the liver enzyme P450 in blood flow.

In one or more of the above aspects, the processing circuit is further configured to determine a heart rate and respiratory rate from the first or second PPG signals; determine an estimation of blood pressure from the first or second PPG signals; and determine a hybrid quick Sequential Organ Failure Assessment (qSOFA) score using the respiratory rate, the heart rate, the estimation of blood pressure and the R value.

BRIEF DESCRIPTION OF THE DRAWINGS

FIG. 28A illustrates a graphical representation of clinical data of a sample patient over a four day time period.

FIG. 28B illustrates a graphical representation of clinical data of the sample patient showing an expansion of a first period in FIG. 28A.

FIG. 38 illustrates a graphical representation of embodiments of methods of the biosensor 100 for screening and monitoring COVID-19 patients.

DETAILED DESCRIPTION

Figure 1:
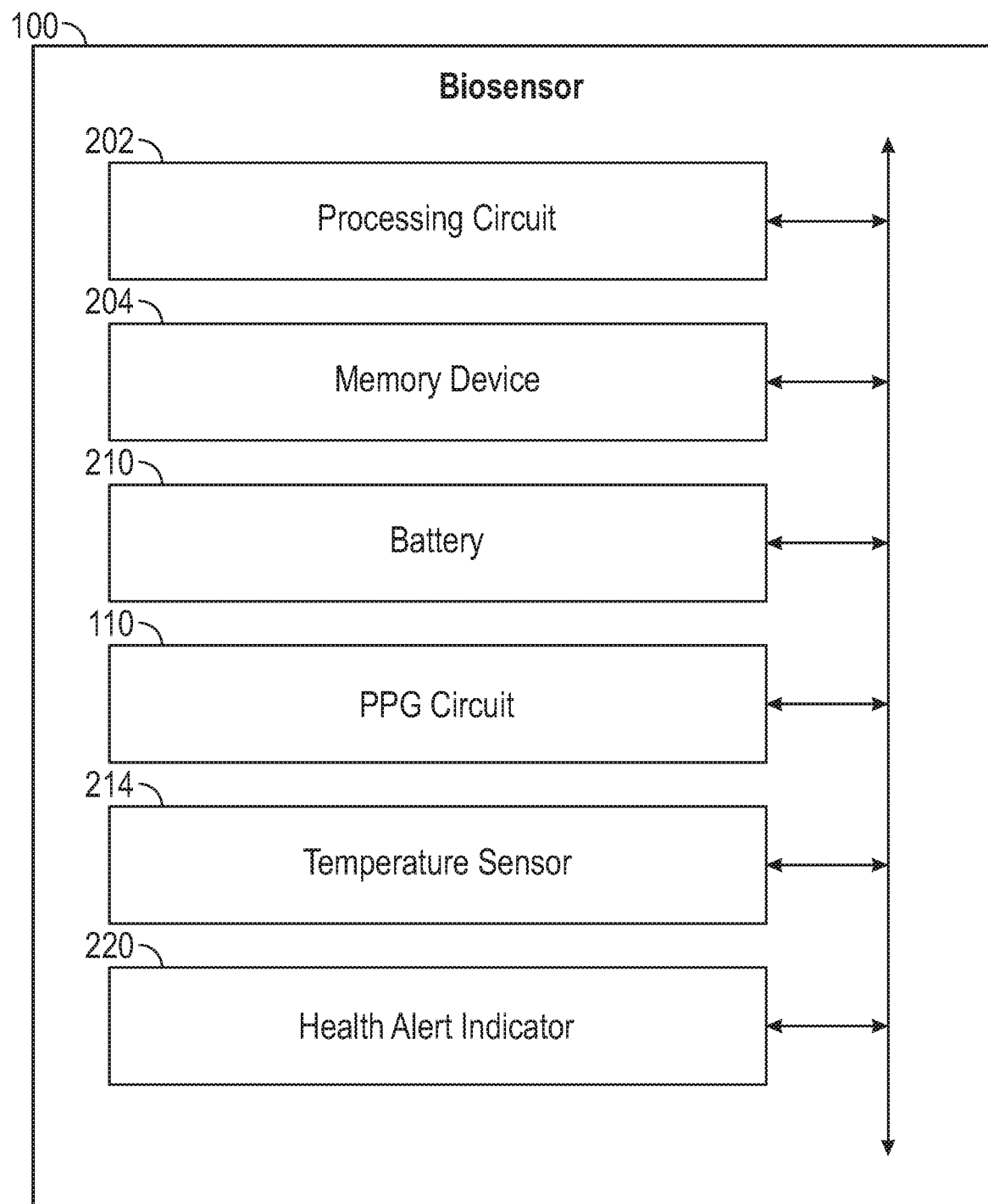
FIG. 1 illustrates a schematic block diagram of exemplary components in an embodiment of the biosensor.

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Nitric oxide (NO) is produced by a group of enzymes called nitric oxide synthases. These enzymes convert arginine into citrulline, producing NO in the process. Oxygen and NADPH are necessary co-factors. There are three isoforms of nitric oxide synthase (NOS) named according to their activity or the tissue type in which they were first described. The isoforms of NOS are neural NOS (or nNOS, type 1), inducible NOS (or iNOS, type 2), and endothelial NOS (or eNOS, type 3). These enzymes are also sometimes referred to by number, so that nNOS is known as NOS1, iNOS is known as NOS2, and eNOS is NOS3. Despite the names of the enzymes, all three isoforms can be found in variety of tissues and cell types. Two of the enzymes (nNOS and eNOS) are constitutively expressed in mammalian cells and synthesize NO in response to increases in intracellular calcium levels. In some cases, however, they are able to increase NO production independently of calcium levels in response to stimuli such as shear stress.

In most cases NO production increases in proportion to the number of calories or food consumed. Normally this is derived from the eNOS type NO production, and the body uses the NO first as a vasodilator and also as a protective oxidation layer to prevent undesired oxides from passing thru the cells in the blood vessels walls. The amount of NO released in this case is measured in small pulses and builds up as part of the normal digestion process. In the case of type 1 or type 2 diabetics, the normal levels of eNOS are abnormally low as found in recent clinical studies.

However, iNOS activity is independent of the level of calcium in the cell, and all forms of the NOS isoforms are dependent on the binding of calmodulin. Increases in cellular calcium lead to increase in levels of calmodulin and the increased binding of calmodulin to eNOS and nNOS leads to a transient increase in NO production by these enzymes. By contrast iNOS is able to bind tightly to calmodulin even at extremely low concentrations of calcium. Therefore, iNOS activity does not respond to changes in calcium levels in the cell. As a result of the production of NO by iNOS, it lasts much longer than other forms of isoforms of NOS and tends to produce much higher concentrations of NO in the body. This is likely the reason that iNOS levels are known to be elevated in dementia & Alzheimer's patents and have increased calcium deposits in their brain tissue.

Inducible iNOS levels are highly connected with infections, such as sepsis, which typically leads to large levels of NO in the blood stream, which in turns leads to organ failure. Lastly abnormal amounts of nNOS levels are typically associated with issues with blood pressure regulation, neurotransmission issues and penal erection. Thus, the overproduction or underproduction of NO levels may be associated with many different health conditions. These health conditions may be detected by measuring NO levels in tissue and/or in the blood stream of a patient. The NO levels include levels of one or more of: gaseous NO, nNOS levels and/or other NO compounds, either measured as a relative level, concentration in mmol/liter, percentage, etc.

Overview of Detection of Sepsis

The signs and symptoms of sepsis may be subtle. The unacceptably low survival rate of severe sepsis indicates that current patient diagnosis strategies are lacking in timeliness and accuracy. SIRS (systemic inflammatory response syndrome) refers to the systemic activation of the body's immune response. SIRS is manifested by, for example, the presence of more than one of a temperature greater than 38° C. or less than 36° C.; a heart rate greater than 90 beats/min.; a respiration rate greater than 20 breaths/min. or white blood count over 12,000 or less than 4,000. Prior definitions of sepsis included that two or more of the SIRS symptoms are present with a confirmed or suspected infection. Severe sepsis was defined as signs of end organ damage, hypotension or blood tests confirming an elevated lactate level. For example, factors in diagnosis of severe sepsis include elevated lactate, creatinine greater than 2 mg/dL, Bilirubin greater than 2 mg/dL, platelet count less than 100,000 and urine output less than 0.5 mL/kg/hr or more than 2 hours despite fluid resuscitation. Septic shock ensues from severe sepsis and persistent low blood pressure despite fluid resuscitation.

Other definitions of sepsis include a Sequential [Sepsis-Related] Organ Failure Assessment (SOFA) score and a quick SOFA (qSOFA) score. Under the qSOFA score, sepsis is diagnosed with systolic blood pressure of less than 100 mmHg, an altered mental status, and respiration rate greater than 22 breaths/min. The SOFA score provides a score of 0-4 using, e.g., the following factors: respiration/oxygen levels, coagulation platelets, liver bilirubin, cardiovascular, CNS GCS score, renal creatinine level and urine output. There is no definition for severe sepsis, and septic shock is a subset of sepsis wherein needing vasopressors for a mean arterial blood pressure (MAP) greater or equal to 65 mmHg or an increase in lactate greater than 2 mmol/L despite adequate fluid resuscitation. A table summarizing the SOFA score is shown below.

TABLE 1

| | Score | | | | |
|---|---|---|---|---|---|
| | 0 | 1 | 2 | 3 | 4 |
| Respiratory system | | | | | |
| PaO$_2$/FiO$_2$ (mmHg) | ≥400 | <400 | <300 | <200 with respiratory support | <100 with respiratory support |
| Hepatic system | | | | | |
| Bilirubin (mg/dL) | <1.2 | 1.2-1.9 | 2.0-5.9 | 6.0-11.9 | >12.0 |
| Cardiovascular system | | | | | |
| | MAP ≥70 mmHg | MAP <70 mmHg | Dopamine <5 or dobutamine (any dose)* | Dopamine 5.1 to 15 or epinephrine ≤0.1 or norepi-nephrine ≤0.1* | Dopamine >15 or epinephrine >0.1 or norepi-nephrine >0.1* |
| Coagulation | | | | | |
| Placelets × 10$^3$/μL | ≥150 | <150 | <100 | <50 | <20 |
| Central Nervous System | | | | | |
| Glasgow coma scale | 15 | 13-14 | 10-12 | 6-9 | <6 |
| Renal system | | | | | |
| Creatinine (mg/dL) | <1.2 | 1.2-1.9 | 2.0-3.4 | 3.5-4.9 | >5.0 |
| Urine Output (mL/d) | | | | <500 | <200 |

Notes:
*All catecholamine doses represent μg/kg/min. Organ dysfunction is identified as an increase in the SOFA score of ≥2 points. In patients with not known preexisting organ dysfunction, the baseline SOFA score is assumed to be zero. Intensive Care Med. The SOFA (Sepsis-related Organ Failure Assesment) score to describe organ dysfunction/failure. On behalf of the Working Group on Sepsis-Related Problems of the European Society of Intensive Care Medicine. 22(7), 1996, 707-710, Vincent JL, Moreno R, Takala J, et. al. Abbreviations: PaO2—partial pressure of oxogen; FiO2—fraction of inspired oxogen; MAP—mean arterial pressure.

However, many of the parameters in the SOFA score and prior definitions require blood samples and laboratory tests that may take hours. Thus, the diagnosis and treatment of sepsis may be delayed. Since sepsis has an 8% mortality rate compounded per hour left untreated, the delay in diagnosis and treatment of sepsis may affect a patient's outcome.

Moreover, conventional tests for sepsis give insufficient advance warning of deteriorating patient health, e.g. from SIRS to sepsis to septic shock. Many of the various parameters in Table 1 require blood tests, such as bilirubin levels and platelet levels. For example, blood tests may include a complete blood count (CBC), C-reactive protein (CRP), endotoxin, procalcitonin (PCT), blood culture (to identify type of bacterial virus, or fungal infection) and serum lactate levels. Urinalysis and urine cultures may also be performed. A physician may also want to test for specific infections, such as a chest x-ray for pneumonia, sputum test for an infection in the throat or lungs, CT or MRI for meningitis, RT-PRC for COVID-19, influenza tests, strep throat, etc. These types of tests are invasive, non-continuous, costly, and time consuming. Since sepsis is very dangerous and may escalate to life threatening conditions quickly, this diagnosis process is not sufficient for early warning of sepsis.

It has been shown that sepsis causes an increased amount of nitric oxide (NO) to be released into the blood stream. The role of nitric oxide in sepsis is described in the article entitled "Nitric oxide in septic shock," by Michael A. Tiitheradge, Biochimica et Biophysica Acta 1411 (1999) 437-455, which is hereby incorporated by reference herein. As described in the article, a patient in septic shock has hepatic glucose production that causes extreme levels of lactate and amino acids. This in turn accelerates production of Nitric Oxide or related Nitrate compounds to critical levels within the body. The overproduction of NO during sepsis induces excessive vascular relaxation and a profound hypotension that is also a characteristic feature of sepsis.

In one or more embodiments herein, an early warning system and method is described for early detection or prediction of sepsis. A biosensor detects NO levels in vivo in the blood stream of a patient. The biosensor includes an optical sensor circuit configured to determine NO levels in blood vessels and/or surrounding tissue of a patient. The biosensor may also detect temperature as well as other vital signs indicative of sepsis, such as pulse rate and respiration rate. The biosensor includes a visible or audible indicator that signals detection of sepsis or a risk of sepsis. The biosensor thus provides a noninvasive and continuous monitoring tool for early warning of a patient's condition and allows for more immediate medical intervention. The patient may include any type of user, either animal or human. The patient may or may not be under medical care or in a medical facility. For example, the patient may be a user at home or at work.

Embodiment of the Biosensor

In an embodiment, the biosensor includes an optical sensor photoplethysmography (PPG) circuit configured to transmit light at a plurality of wavelengths directed at skin tissue of a patient. The patient may include any living organism, human or non-human. The PPG circuit detects the light reflected from the skin tissue and generates spectral responses at the plurality of wavelengths. The processing circuit is configured to obtain a measurement of NO levels from the spectral responses at the plurality of wavelengths using one or more measurement techniques described herein.

FIG. 1 illustrates a schematic block diagram of exemplary components in an embodiment of the biosensor 100. The biosensor 100 includes an optical or PPG circuit 110 as described in more detail herein. The PPG circuit 110 may be configured to detect oxygen saturation (SaO2 or SpO2) levels in blood flow, as well as heart rate and respiration rate. In addition, the PPG circuit 110 is configured to detect levels of NO in blood vessels and/or surrounding tissue of a user as described in more detail herein.

The biosensor 100 also includes one or more processing circuits 202 communicatively coupled to a memory device 204. In one aspect, the memory device 204 may include one or more non-transitory processor readable memories that store instructions which when executed by the one or more processing circuits 202 or other components of the biosensor 100, causes the one or more processing circuits 202 or other components to perform one or more functions described herein. The processing circuit 202 may be co-located with one or more of the other circuits of the biosensor 100 in a same physical circuit board or located separately in a different circuit board or encasement. The biosensor 100 may be battery operated and include a battery 210, such as a lithium ion battery. In an embodiment, the battery 210 is disposable and designed to include a short lifespan of 24-48 hours.

The biosensor 100 may also include a temperature sensor 214 configured to detect a temperature of a patient. For example, the temperature sensor 214 may include an array of sensors (e.g., 16×16 pixels) positioned on the biosensor 100 such that the array of sensors are adjacent to the skin of the patient. The array of sensors is configured to detect a temperature of the patient from the skin. The temperature sensor 214 may also be used to calibrate the PPG circuit 110, e.g. such as the LEDs in the PPG circuit 110.

The biosensor 100 may also include a health alert indicator 220. The health alert indicator 220 may include one or more LEDs or a display. When symptoms of sepsis are detected, the health alert indicator may illuminate to provide a warning. For example, a first LED may illuminate a first color (e.g. green) to indicate no or little risk of sepsis has been detected while a second LED may illuminate a second color (e.g. red) to indicate a risk of sepsis.

Figure 2:
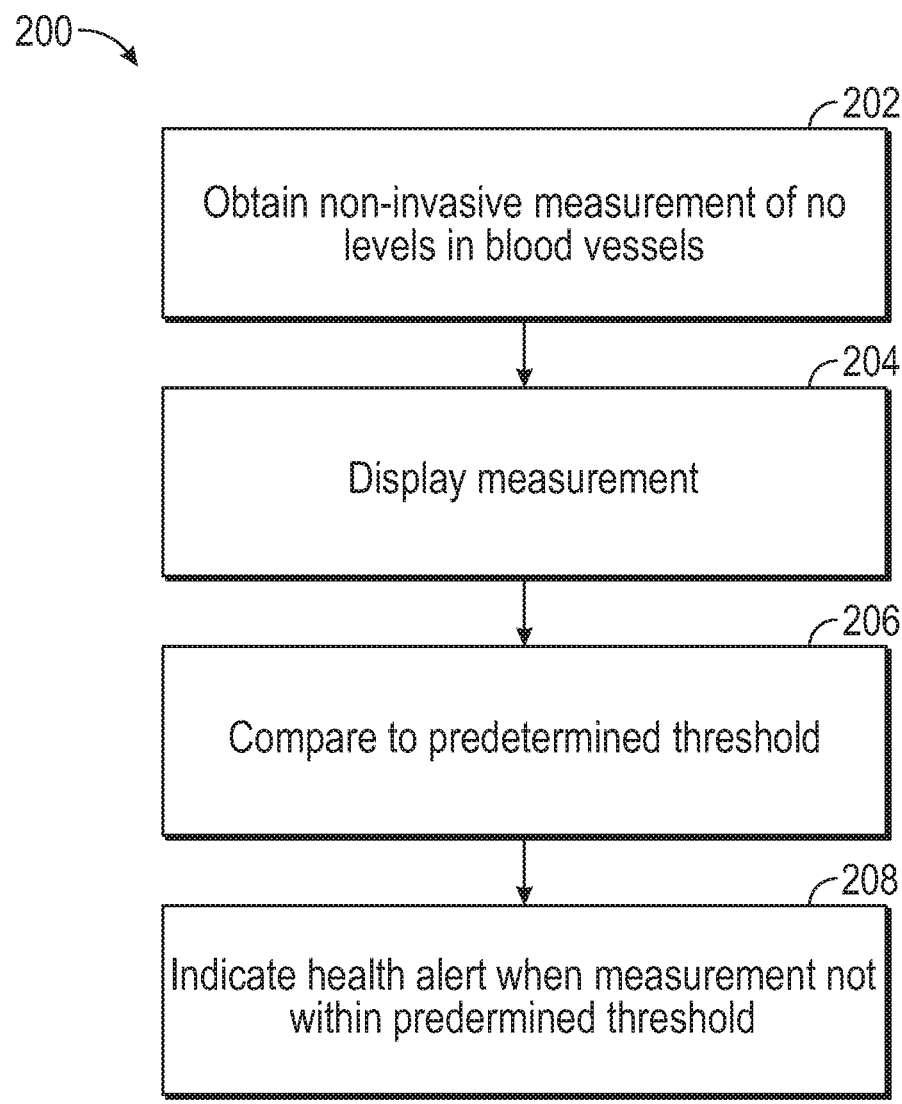
FIG. 2 illustrates a logical flow diagram of an exemplary embodiment of a method for detecting a risk of sepsis by the biosensor.

FIG. 2 illustrates a logical flow diagram of an exemplary embodiment of a method 300 for detecting sepsis by the biosensor 100. The biosensor 100 non-invasively obtains an NO measurement related to the level of NO in blood vessels and/or surrounding tissue at 202. An indication of the NO measurement may be displayed at 204. For example, the patch 102 may include a row of LEDs that are illuminated to indicate the level of the NO. Alternatively, the patch 102 may include an LED configured to illuminate one or more colors or hues to indicate the level of NO. In another aspect, a display may display a concentration (mmol/liter) or relative level of measured NO.

The NO measurement of the patient is compared to predetermined levels at 306. For example, the predetermined threshold may be based on a range of average or mean NO measurements of a sample healthy population without a sepsis condition. The NO measurement of an individual patient may then be compared to the normal range derived from the sample healthy population. Depending on the comparison, the NO measurement may be determined within normal ranges. Alternatively, the NO measurement may be determined to be higher than the predetermined normal ranges. An indication of a health alert may then be displayed when the NO measurement is indicative of a risk of sepsis at 308.

Figure 3:
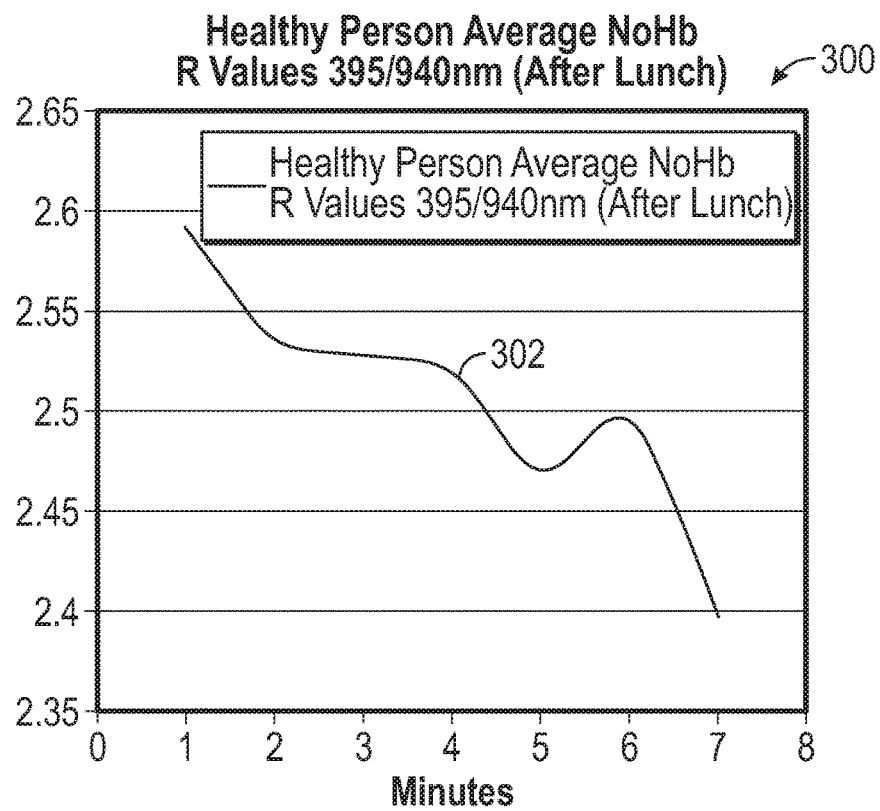
FIG. 3 illustrates a graph of a measurement of NO levels for a normal healthy patient without an infection.
Figure 4:
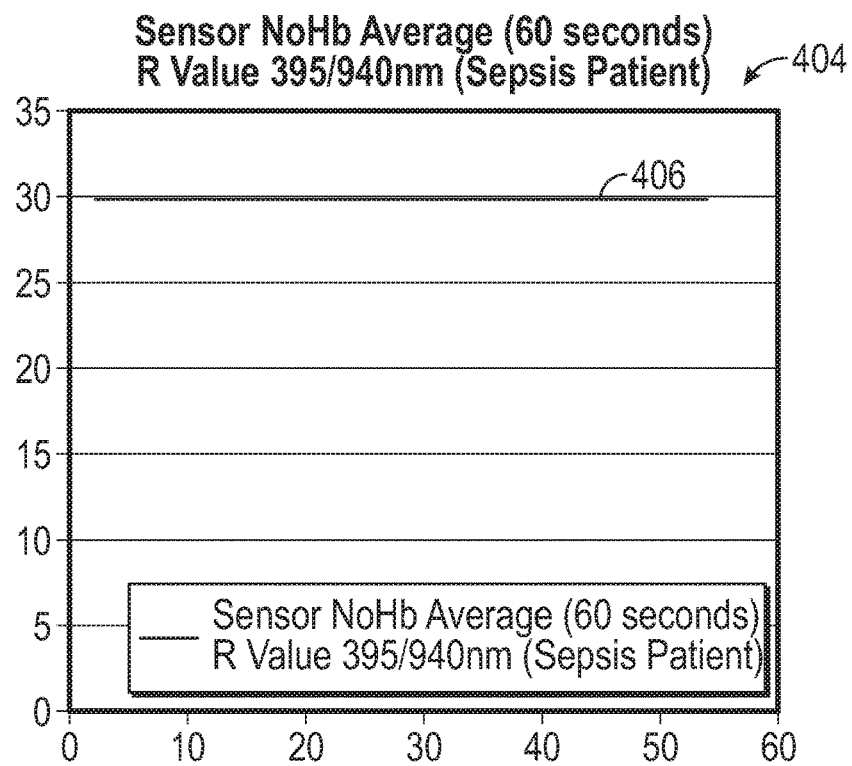
FIG. 4 illustrates a schematic diagram of a graph of actual clinical data obtained using an embodiment of the biosensor from a patient with a diagnosis of sepsis.

FIGS. 3 and 4 illustrate schematic diagrams of graphs of actual clinical data obtained using an embodiment of the biosensor 100. FIG. 3 illustrates a graph 300 of a measurement of NO levels for a normal healthy patient without an infection. The NO measurement is obtained from a ratio R or R value 302. The R value 302 is obtained from a spectral response in the ultraviolet (UV) range at 395 nm and a spectral response in the infrared (IR) range at 940 nm.

In unexpected results, the UV range from 380 nm to 410 nm, and in particular at 390 nm, has been determined to have a high absorption coefficient for NO or NO compounds. The NO levels in vivo in blood vessels may thus be measured without a need for a blood sample or lab analytics. In this graph 400, the average R value 402 for the healthy patient ranges from 2.6 to 2.4.

FIG. 4 illustrates a schematic diagram of a graph 404 of actual clinical data obtained using an embodiment of the biosensor 100 from a patient with a diagnosis of sepsis. The graph 404 illustrates a measurement of NO levels for the patient with sepsis. The NO measurement is obtained from a ratio R or R value 406. The R value 406 is obtained from a spectral response in the UV range and a spectral response in the IR range. In one aspect, the first wavelength in the UV range is from 380-410 nm and in this example, is from an LED with a wavelength of 395 nm. As seen in the graph, R value 406 is around 30 for the patient with sepsis.

Nitric oxide (NO) is found in the blood stream in a gaseous form and also bonded to a plurality of types of hemoglobin species. The measured NO levels obtained using the UV range from 380-410 include measurements of NO in gaseous form as well as the NO bonded to the plurality of types of hemoglobin species in the blood vessels. The measured NO concentration levels may thus include NO in various isoforms, in gaseous form or bonded to a plurality of types of hemoglobin species. The NO measurement levels obtained as described herein are thus more sensitive and have a greater dynamic range than other methods for measuring NO levels based on a single species of hemoglobin, such as methemoglobin (HbMet). The NO measurements herein may also provide an earlier detection of increases in NO in blood vessels than measurements based on HbMet alone. In addition, the NO measurements may also extend to ranges beyond hemoglobin saturation levels.

In one clinical trial, it was determined that the average R value may range from 0.1 to 8 for a patient without a sepsis condition. In addition, it was determined that an average R value of 30 or higher is indicative of a patient with a sepsis condition and that an average R value of 8-30 was indicative of a risk of sepsis in the patient. In general, an R value of 2-3 times a baseline R value was indicative of a risk of sepsis in the patient.

Figure 5:
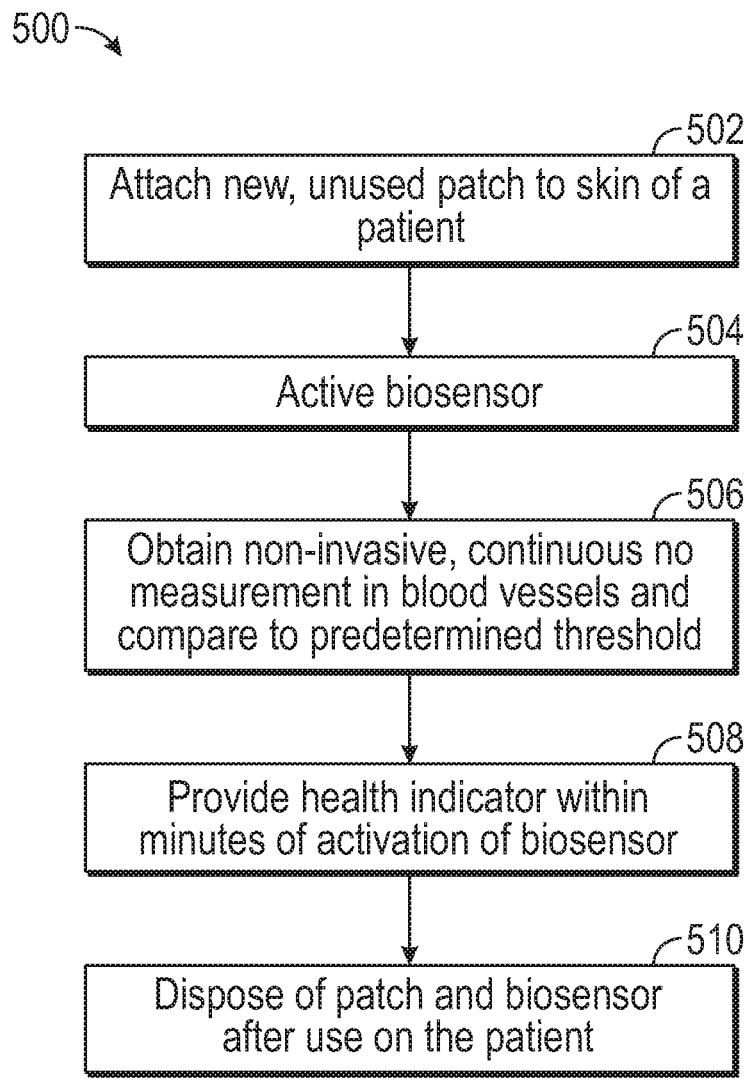
FIG. 5 illustrates a logical flow diagram of an embodiment of a method for use of the biosensor.

FIG. 5 illustrates a logical flow diagram of an embodiment of a method 500 for use of the biosensor 100. In this embodiment, the biosensor 100 may include a disposable finger attachment or be located in a disposable patch form factor. A new, unused patch 102 is attached to skin tissue of a patient at 502 or a finger of the patient positioned in the disposable finger attachment. The disposable patch may include an adhesive backing such that it may adhere to a patient's skin. The patch may additionally or alternatively be secured through other means, such as tape, band, etc.

The biosensor 100 is activated at 504. The biosensor 100 non-invasively monitors an NO measurement related to the concentration of NO in blood vessels at 506. The NO measurement of the patient is compared to one or more predetermined thresholds. For example, the predetermined thresholds may be derived based on measurements of a sample healthy general population. A mean or range of average values for the NO measurement from the sample healthy population may then be used to set the predetermined thresholds. The NO measurement of the patient may then be compared to the predetermined thresholds derived from the sample healthy population. In an embodiment, the mean or range of values of NO levels in patients with sepsis may be obtained. For example, patients diagnosed with sepsis using traditional methods may be tested over days and weeks to determine a range of NO levels indicating sepsis.

Within minutes of activation, the patch 102 may determine the NO measurement and provide a health indicator at 508. Depending on the comparison of the NO measurement to the one or more predetermined thresholds, the health indicator may signal that the NO measurement is within predetermined normal ranges. Alternatively, the health indicator may signal that the NO measurement is not within than the predetermined thresholds, e.g. outside normal ranges or in a range indicative of sepsis. The health indicator then provides a warning or alert of a risk of sepsis.

To lower costs, the health indicator may include one or more LEDs on the patch 102. For example, the patch 102 may include a row of LEDs that are illuminated to indicate the level of the NO concentration. Alternatively, the patch 102 may include an LED configured to illuminate in one or more colors or hues to indicate the level of NO concentration, a first color to indicate normal ranges and a second color to indicate not within normal ranges. In another embodiment, the patch 102 may include a display that provides a visual indication of the NO measurement.

When monitoring of the single patient is complete, the disposable finger attachment is removed and disposed. A new disposable finger attachment is then obtained and used with a next patient. The disposable finger attachment is thus designed for use with a single patient.

In an embodiment with a disposable patch, the disposable patch including the biosensor 100 is disposed of. The disposable patch is thus designed and manufactured for a single use on a single patient for a short duration of time, e.g. 24-48 hours. The disposable patch form factor 102 has several advantages including a low cost (such as under $10). The patch 102 is easy to use with a simple visible indicator. The patch may be sold for hospital or home use to provide a health indicator within minutes. For example, the patch 102 may be used in triage at hospitals or clinics, or the patch 102 may be used at home to monitor an at risk patient to determine a possible infection or risk of sepsis.

Embodiment—Circuit

Figure 6:
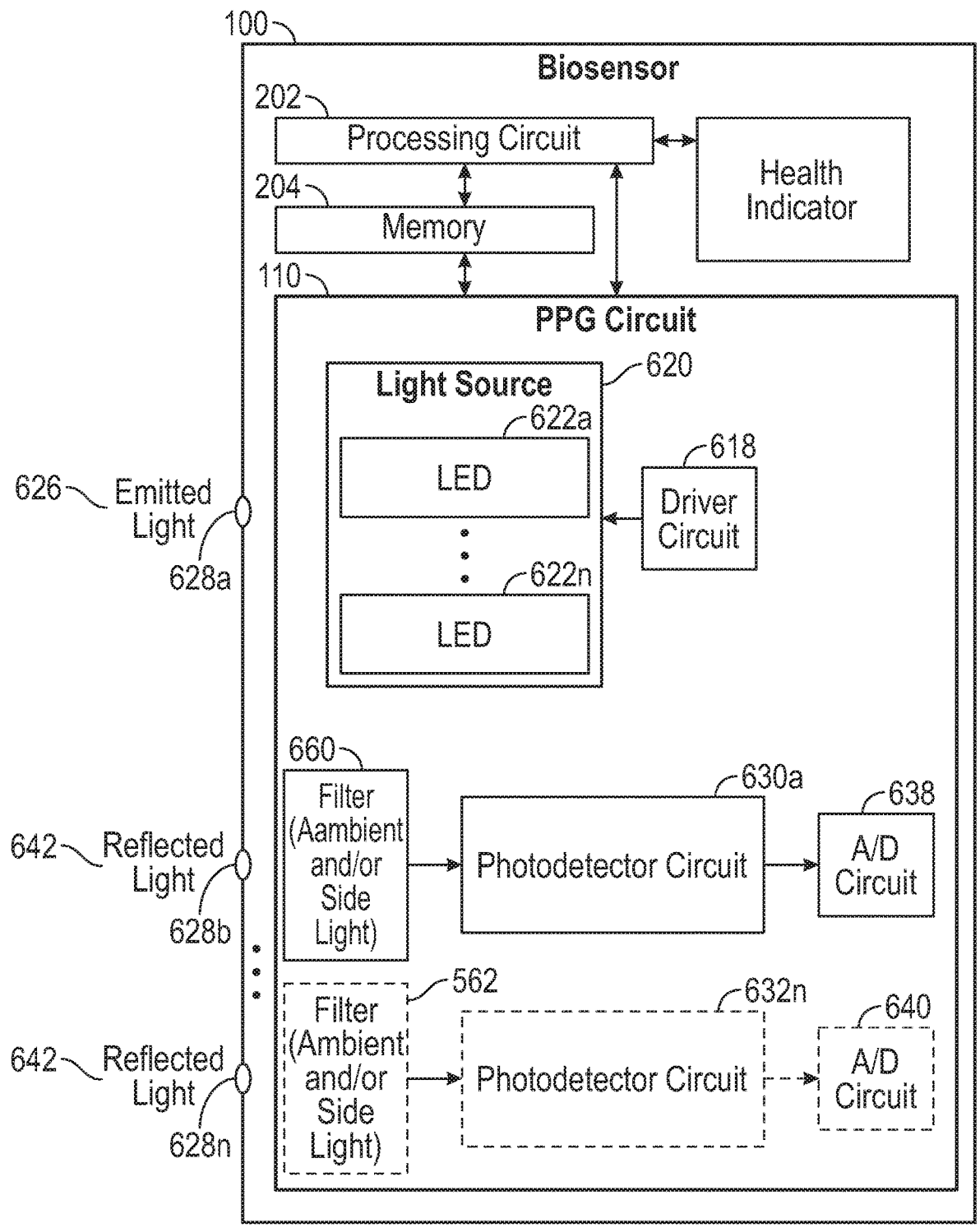
FIG. 6 illustrates a schematic block diagram illustrating an embodiment of the PPG circuit in more detail.

FIG. 6 illustrates a schematic block diagram illustrating an embodiment of the PPG circuit 110 in more detail. The PPG circuit 110 includes a light source 620 configured to emit a plurality of wavelengths of light across various spectrums. For example, the light source 620 mat include a plurality of LEDs 622a-n. The PPG circuit 110 is configured to direct the emitted light at an outer or epidermal layer of skin tissue of a patient through at least one aperture 628a. The plurality of LEDs 622a-n are configured to emit light in one or more spectrums, including infrared (IR) light, ultraviolet (UV) light, near IR light or visible light, in response to driver circuit 618. For example, the biosensor 100 may include a first LED 622a that emits visible light and a second LED 622b that emits infrared light and a third LED 622c that emits UV light, etc. In another embodiment, one or more of the light sources 622a-n may include tunable LEDs or lasers operable to emit light over one or more frequencies or ranges of frequencies or spectrums in response to driver circuit 618.

In an embodiment, the driver circuit 618 is configured to control the one or more LEDs 622a-n to generate light at one or more frequencies for predetermined periods of time. The driver circuit 618 may control the LEDs 622a-n to operate concurrently or consecutively. The driver circuit 618 is configured to control a power level, emission period and frequency of emission of the LEDs 622a-n. The biosensor 100 is thus configured to emit one or more wavelengths of light in one or more spectrums that is directed at the surface or epidermal layer of the skin tissue of a patient.

The PPG circuit 110 further includes one or more photodetector circuits 630a-n. For example, a first photodetector circuit 630 may be configured to detect visible light and the second photodetector circuit 630 may be configured to detect IR light. Alternatively, both photodetectors 630a-n may be configured to detect light across multiple spectrums and the signals obtained from the photodetectors are added or averaged. The first photodetector circuit 630 and the second photodetector circuit 630 may also include a first filter 660 and a second filter 662 configured to filter ambient light and/or scattered light. For example, in some embodiments, only light reflected at an approximately perpendicular angle to the skin surface of the patient is desired to pass through the filters. The first photodetector circuit 630 and the second photodetector circuit 632 are coupled to a first A/D circuit 638 and a second A/D circuit 640. Alternatively, a single A/D circuit may be coupled to each of the photodetector circuits 630a-n.

In another embodiment, a single photodetector circuit 630 may be implemented operable to detect light over multiple spectrums or frequency ranges. The one or more photodetector circuits 630 include one or more types of spectrometers or photodiodes or other type of circuit configured to detect an intensity of light as a function of wavelength to obtain a spectral response. In use, the one or more photodetector circuits 630 detect the intensity of light reflected from skin tissue of a patient that enters one or more apertures 628b-n of the biosensor 100. In another example, the one or more photodetector circuits 630 detect the intensity of light due to transmissive absorption (e.g., light transmitted through tissues such as a fingertip or ear lobe). The one or more photodetector circuits 630a-n then obtain a spectral response of the reflected or transmissive light by measuring an intensity of the light at one or more wavelengths.

In another embodiment, the light source 620 may include a broad spectrum light source, such as a white light to infrared (IR) or near IR LED 622, that emits light with wavelengths from e.g. 350 nm to 2500 nm. Broad spectrum light sources 620 with different ranges may be implemented. In an aspect, a broad spectrum light source 620 is implemented with a range across 100 nm wavelengths to 2000 nm range of wavelengths in the visible, IR and/or UV frequencies. For example, a broadband tungsten light source 620 for spectroscopy may be used. The spectral response of the reflected light is then measured across the wavelengths in the broad spectrum, e.g. from 350 nm to 2500 nm, concurrently. In an aspect, a charge coupled device (CCD) spectrometer may be configured in the photodetector circuit 630 to measure the spectral response of the detected light over the broad spectrum.

Embodiment—Measurement of NO Levels

One or more of the embodiments of the biosensor 100 described herein is configured to detect a level of NO within blood flow and/or surrounding tissue using photoplethysmography (PPG) techniques. The biosensor 100 may detect NO levels as well as peripheral oxygen ($SpO_2$ or $SaO_2$) saturation, concentration of one or more other substances as well as patient vitals, such as pulse rate and respiration rate.

In use, the biosensor 100 performs PPG techniques using the PPG circuit 110 to detect the levels of one or more substances in blood flow and/or surrounding tissue. In one aspect, the biosensor 100 receives reflected light from skin tissue to obtain a spectral response. The spectral response includes a spectral curve that illustrates an intensity or power or energy at a frequency or wavelength in a spectral region of the detected light. The ratio of the resonance absorption peaks from two different frequencies is calculated and based on the Beer-Lambert law used to obtain the levels of substances in the blood flow.

First, the spectral response of a substance or substances in the blood flow is determined in a controlled environment, so that an absorption coefficient $\alpha_{g1}$ can be obtained at a first light wavelength $\lambda 1$ and at a second wavelength $\lambda 2$. According to the Beer-Lambert law, light intensity will decrease logarithmically with path length l (such as through an artery of length l). Assuming then an initial intensity $I_{in}$ of light is passed through a path length l, a concentration $C_g$ of a substance may be determined using the following equations:

At the first wavelength $\lambda_1$, $I_1 = I_{in1} * 10^{-(\alpha_{g1} C_{gw} + \alpha_{w1} C_w) * l}$ At the second wavelength $\lambda_2$, $I_2 = I_{in2} * 10^{-(\alpha_{g2} C_{gw} + \alpha_{w2} C_w) * l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{log10\left(\frac{I_1}{I_{in1}}\right)}{log10\left(\frac{I_2}{I_{in2}}\right)}$$

The concentration of the substance Cg may then be equal to:

$$Cg = \frac{Cgw}{Cgw + Cw} = \frac{\alpha_{w2} R - \alpha_{w1}}{(\alpha_{w2} - \alpha_{gw2}) * R - (\alpha_{w1} - \alpha_{gw1})}$$

The biosensor 100 may thus determine the concentration of various substances in arterial blood flow from the Beer-Lambert principles using the spectral responses of at least two different wavelengths. These calculations may be modified to determine concentration in venous blood flow as well as arterial blood flow and/or surrounding tissue.

Figure 7:
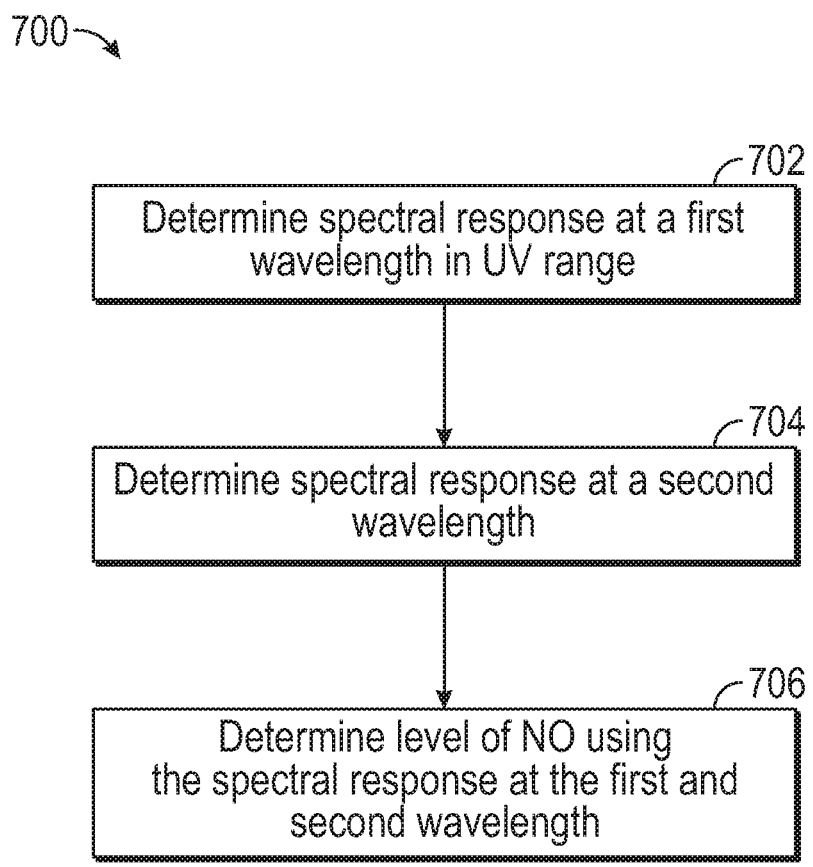
FIG. 7 illustrates a logical flow diagram of an embodiment of a method for determining a level of NO using Beer-Lambert principles.

FIG. 7 illustrates a logical flow diagram of an embodiment of a method 700 for determining level of NO using Beer-Lambert principles. The biosensor 100 transmits light at least at a first predetermined wavelength and at a second predetermined wavelength. The biosensor 100 detects the light (reflected from the skin tissue or transmitted through the skin tissue) and determines the spectral response at the first wavelength at 702 and at the second wavelength at 704. The biosensor 100 then determines an indicator or level of NO using the spectral responses of the first and second wavelength at 706. In general, the first predetermined wavelength is selected that has a high absorption coefficient for NO and/or NO compounds in blood flow while the second predetermined wavelength is selected that has a lower absorption coefficient for NO and/or NO compounds in blood flow. Thus, it is generally desired that the spectral response for the first predetermined wavelength have a higher intensity level in response to NO and/or NO compounds in blood flow than the spectral response for the second predetermined wavelength. In an embodiment, the first predetermined wavelength is in a range of 380-410 nm and in particular at 390 nm or 395 nm.

In another aspect, the biosensor 100 may transmit light in a range of approximately 1 nm to 50 nm around the first predetermined wavelength. Similarly, the biosensor 100 may transmit light in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted by NO may spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated at 702 and 704. The biosensor 100 analyzes the first and second spectral responses to detect an indicator or level of NO in the blood flow and/or surrounding tissue at 706.

Figure 8A:
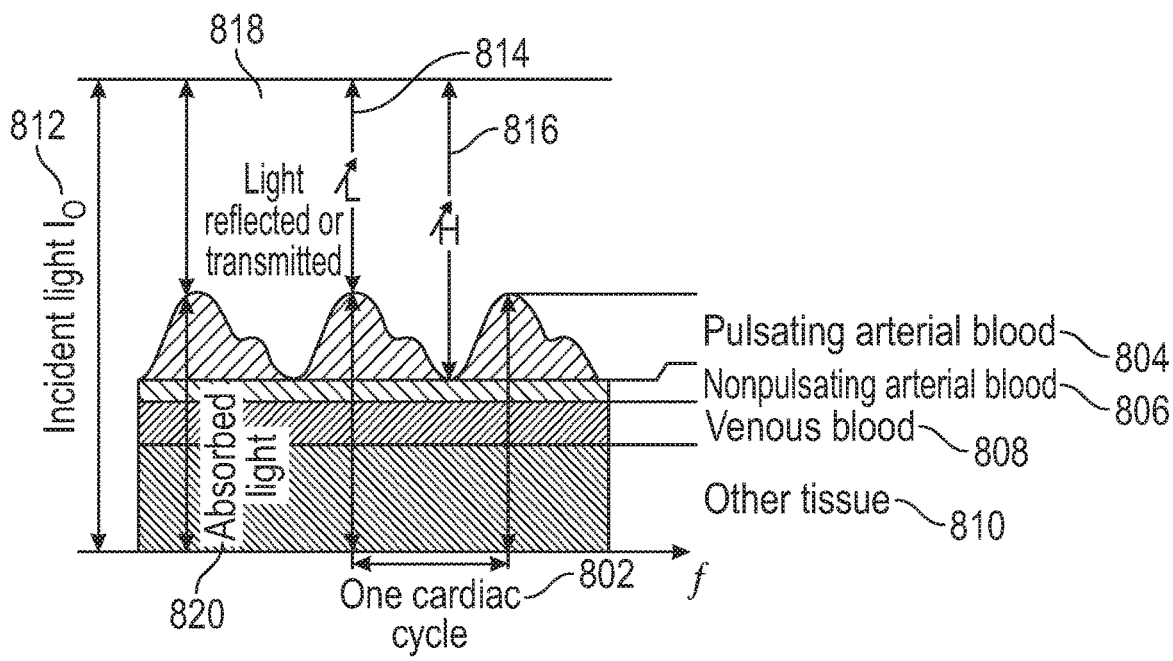
FIG. 8A illustrates a schematic block diagram of an embodiment of a method for PPG techniques in more detail
Figure 8B:
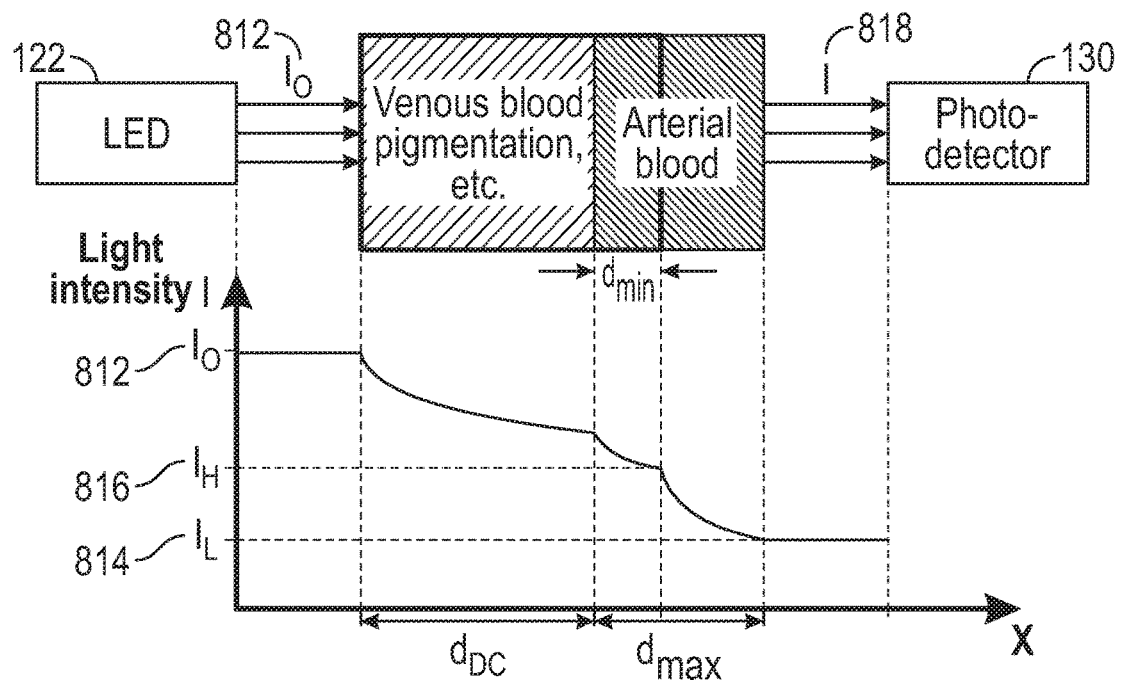
FIG. 8B illustrates a schematic block diagram of an embodiment of a method for PPG techniques in more detail.

FIG. 8A and FIG. 8B illustrate schematic block diagrams of an embodiment of a method for photoplethysmography (PPG) techniques in more detail. PPG is used to measure time-dependent volumetric properties of blood in blood vessels due to the cardiac cycle. For example, the heartbeat affects the volume of arterial blood flow and the concentration or absorption levels of substances being measured in the arterial blood flow. As shown in FIG. 8A, over a cardiac cycle 802, pulsating arterial blood 804 changes the volume of blood flow in an artery.

Incident light $I_O$ 812 is directed at a tissue site and a certain amount of light is reflected or transmitted 818 and a certain amount of light is absorbed 820. At a peak of arterial blood flow or arterial volume, the reflected/transmitted light $I_L$ 814 is at a minimum due to absorption by the venous blood 808, nonpulsating arterial blood 806, pulsating arterial blood 804, other tissue 810, etc. At a minimum of arterial blood flow or arterial volume during the cardiac cycle, the transmitted/reflected light $I_H$ 816 is at a maximum due to lack of absorption from the pulsating arterial blood 804.

The biosensor 100 is configured to filter the reflected/transmitted light $I_L$ 814 of the pulsating arterial blood 804 from the transmitted/reflected light $I_H$ 816. This filtering isolates the light due to reflection/transmission of substances in the pulsating arterial blood 804 from the light due to reflection/transmission from venous (or capillary) blood 808, other tissues 810, etc. The biosensor 100 may then measure the levels of one or more substances from the reflected/transmitted light $I_L$ 814 in the pulsating arterial blood flow 804.

For example, as shown in FIG. 8B, incident light $I_O$ 812 is directed at a tissue site by an LED 122 at one or more wavelengths. The reflected/transmitted light I 818 is detected by photodetector 130. At a peak of arterial blood flow or arterial volume, the reflected light $I_L$ 814 is at a minimum due to absorption by venous blood 808, nonpulsating arterial blood 806, pulsating arterial blood 804, other tissue 810, etc. At a minimum of arterial blood flow or arterial volume during the cardiac cycle, the Incident or reflected light $I_H$ 816 is at a maximum due to lack of absorption from the pulsating arterial blood 804. Since the light I 818 is reflected or traverses through a different volume of blood at the two measurement times, the measurement provided by a PPG sensor is said to be a 'volumetric measurement' descriptive of the differential volumes of blood present at a certain location within the patient's arteriolar bed at different times. Though the above has been described with respect to arterial blood flow, the same principles described herein may be applied to venous blood flow.

In general, the relative magnitudes of the AC and DC contributions to the reflected/transmitted light signal I 818 may be used to substantially determine the differences between the diastolic points and the systolic points. In this case, the difference between the reflected light $I_L$ 814 and reflected light $I_H$ 816 corresponds to the AC contribution of the reflected light 818 e.g. due to the pulsating arterial blood flow). A difference function may thus be computed to determine the relative magnitudes of the AC and DC components of the reflected light I 818 to determine the magnitude of the reflected light $I_L$ 814 due to the pulsating arterial blood 804. The described techniques herein for determining the relative magnitudes of the AC and DC contributions is not intended as limiting. It will be appreciated that other methods may be employed to isolate or otherwise determine the relative magnitude of the light $I_L$ 814 due to pulsating arterial blood flow.

Figure 9:
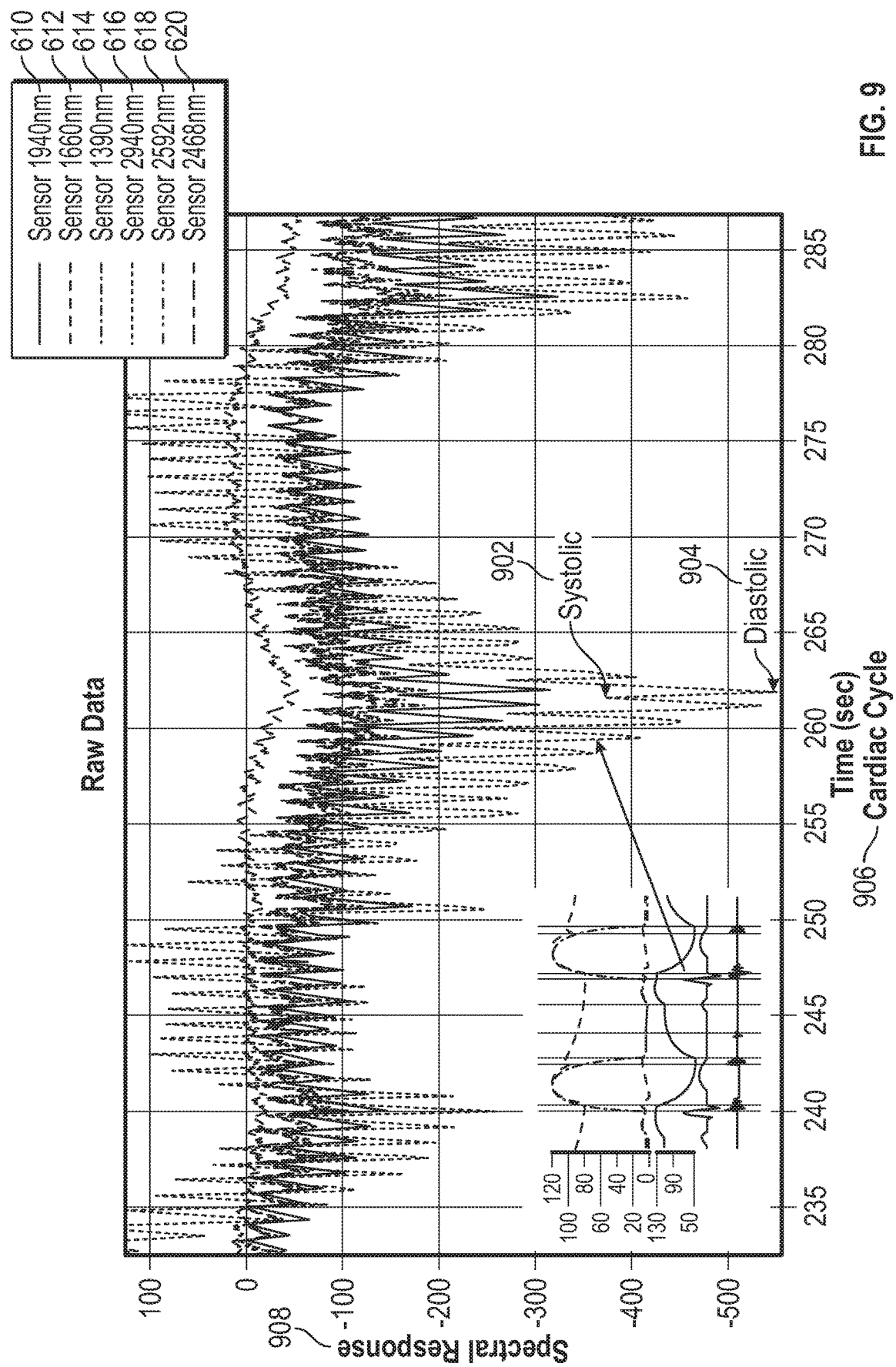
FIG. 9 illustrates a schematic diagram of a graph of actual clinical data obtained using an embodiment of the biosensor 100 and PPG techniques at a plurality of wavelengths.

FIG. 9 illustrates a schematic diagram of a graph of actual clinical data obtained using an embodiment of the biosensor 100 and PPG techniques at a plurality of wavelengths. In one aspect, the biosensor 100 is configured to emit light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral response 908 for the plurality of wavelengths obtained using an embodiment of the biosensor in clinical trials is shown in FIG. 9. In this clinical trial, two biosensors 100 attached to two separate fingertips of a patient were used to obtain the spectral responses 908. The first biosensor 100 obtained the spectral response for a wavelength at 940 nm 610, a wavelength at 660 nm 612 and a wavelength at 390 nm 614. The second biosensor 100 obtained the spectral response for a wavelength at 940 nm 616, a wavelength at 592 nm 618 and a wavelength at 468 nm 620.

In one aspect, the spectral response of each wavelength may be aligned based on the systolic 602 and diastolic 604 points in their spectral responses. This alignment is useful to associate each spectral response with a particular stage or phase of the pulse-induced local pressure wave within the blood vessel (which may mimic the cardiac cycle 906 and thus include systolic and diastolic stages and sub-stages thereof). This temporal alignment helps to determine the absorption measurements acquired near a systolic point in time of the cardiac cycle and near the diastolic point in time of the cardiac cycle 906 associated with the local pressure wave within the patient's blood vessels. This measured local pulse timing information may be useful for properly interpreting the absorption measurements in order to determine the relative contributions of the AC and DC components measured by the biosensor 100. So, for one or more wavelengths, the systolic points 902 and diastolic points 904 in the spectral response are determined. These systolic points 902 and diastolic points 904 for the one or more wavelengths may then be aligned as a method to discern concurrent responses across the one or more wavelengths.

In another embodiment, the systolic points 902 and diastolic points 904 in the absorbance measurements are temporally correlated to the pulse-driven pressure wave within the arterial blood vessels—which may differ from the cardiac cycle. In another embodiment, the biosensor 100 may concurrently measure the intensity reflected at each the plurality of wavelengths. Since the measurements are concurrent, no alignment of the spectral responses of the plurality of wavelengths may be necessary. FIG. 9 illustrates the spectral response of the plurality of wavelengths with the systolic points 902 and diastolic points 904 aligned.

Figure 10:
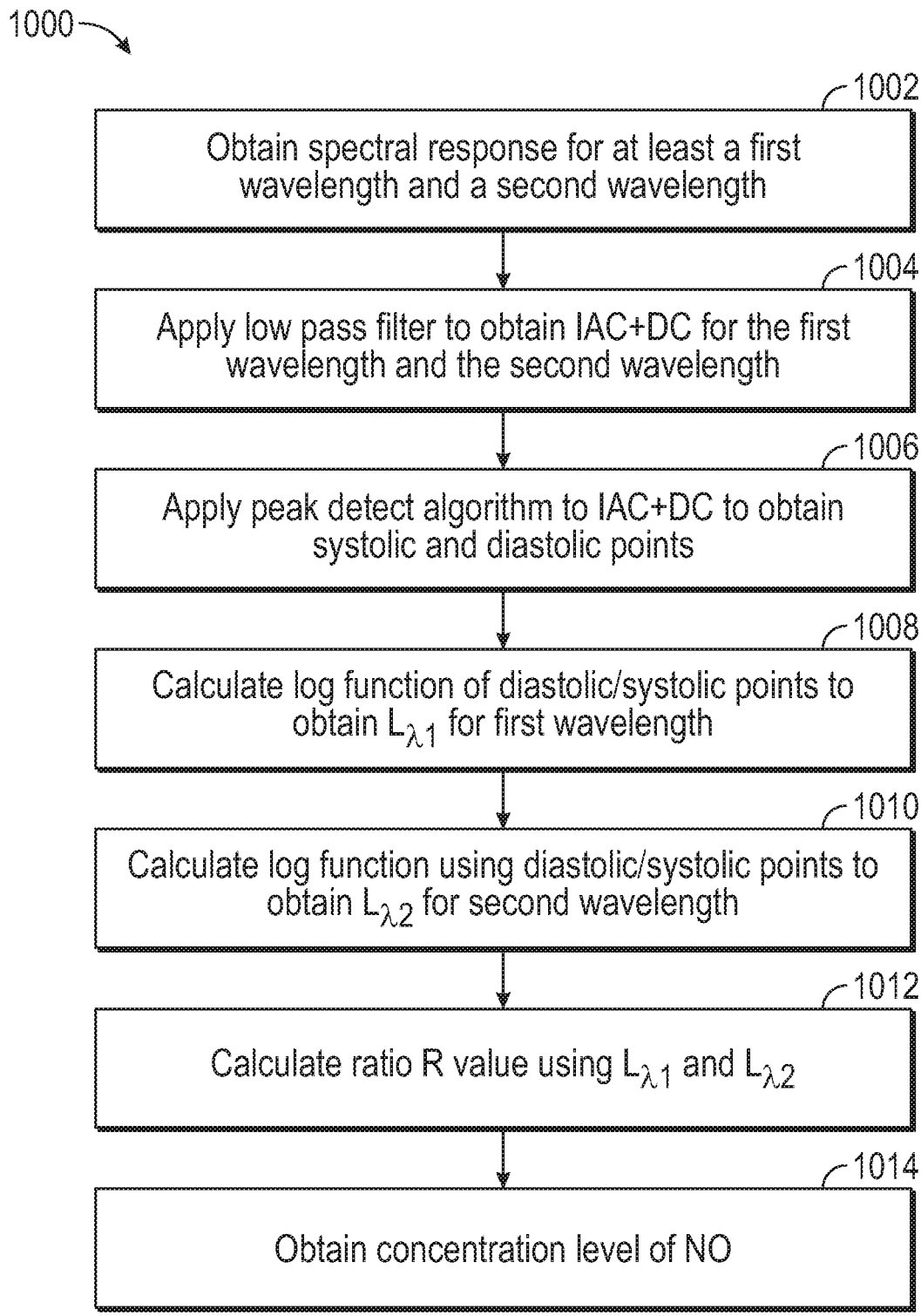
FIG. 10 illustrates a logical flow diagram of an embodiment of a method of the biosensor.

FIG. 10 illustrates a logical flow diagram of an embodiment of a method 1000 of the biosensor 100. In one aspect, the biosensor 100 emits and detects light at a plurality of predetermined frequencies or wavelengths, such as approximately 940 nm, 660 nm, 390 nm, 592 nm, and 468 nm. The light is pulsed for a predetermined period of time (such as 100 usec or 200 Hz) sequentially or simultaneously at each predetermined wavelength. In another aspect, light may be pulsed in a wavelength range of 1 nm to 50 nm around each of the predetermined wavelengths. For example, for the predetermined wavelength 390 nm, the biosensor 100 may transmit light directed at skin tissue of the patient in a range of 360 nm to 410 nm including the predetermined wavelength 390 nm. For the predetermined wavelength of 940 nm, the biosensor 100 may transmit light directed at the skin tissue of the patient in a range of 920 nm to 975 nm. In another embodiment, the light is pulsed simultaneously at least at each of the predetermined wavelengths (and in a range around the wavelengths).

The spectral responses are obtained around the plurality of wavelengths, including at least a first wavelength and a second wavelength at 1002. The spectral responses may be measured over a predetermined period (such as 300 usec.). This measurement process is repeated continuously, e.g., pulsing the light at 10-100 Hz and obtaining spectral responses over a desired measurement period, e.g. from 1-2 seconds to 1-2 minutes or from 2-3 hours to continuously over days or weeks. The absorption levels are measured over one or more cardiac cycles and systolic and diastolic points of the spectral response are determined. Because the human pulse is typically on the order of magnitude of one 1 Hz, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period. The spectral responses are obtained over one or more cardiac cycles and systolic and diastolic points of the spectral responses are determined.

A low pass filter (such as a 5 Hz low pass filter) is applied to the spectral response signal at 1004. The relative contributions of the AC and DC components are obtained $I_{AC+DC}$ and $I_{AC}$. A peak detection algorithm is applied to determine the systolic and diastolic points at 1006. The systolic and diastolic points of the spectral response for each of the wavelengths may be aligned and may also be aligned with systolic and diastolic points of an arterial pulse waveform or cardiac cycle.

Beer Lambert equations are then applied as described herein at 1008. For example, the $L_\lambda$ values are then calculated for the wavelengths λ, wherein the $L_\lambda$ values for a wavelength equals:

$$L_\lambda = \text{Log10}\left(\frac{IAC+DC}{IDC}\right)$$

wherein $I_{AC+DC}$ is the intensity of the detected light with AC and DC components and $I_{DC}$ is the intensity of the detected light with the AC filtered by the low pass filter. The value $L_\lambda$ isolates the spectral response due to pulsating arterial blood flow, e.g. the AC component of the spectral response. Though the $L_\lambda$ value is described in one embodiment by this equation, the L value includes alternate computations that represents the value of the AC component of the spectral response. For example, the L value may be represented alternatively by one or more of:

$$L_\lambda = \frac{IAC}{IDC} \text{ or } L_\lambda = \frac{IAC+DC}{IDC}$$

A ratio R of the $L_\lambda$ values at two wavelengths may then be determined. For example, the ratio R may be obtained from the following:

$$\text{Ratio } R = \frac{L\lambda 1}{L\lambda 2}$$

The R value is thus a ratio of AC components of spectral responses at different wavelengths. The L values and R values may be determined continuously, e.g. every 1-2 seconds, and the obtained $L_\lambda$ values and/or R values averaged or meaned over a predetermined time period, such as over 1-2 minutes. The level of a substance may then be obtained from the R value. The biosensor 100 may substantially continuously monitor a user over 2-3 hours or over days or weeks.

The $R_{390,940}$ value with $L_{\lambda 1=390\ nm}$ and $L_{\lambda 2=940}$ may be non-invasively and quickly and easily obtained using the biosensor 100 in a physician's office or other clinical setting or at home. In particular, in unexpected results, it is believed that nitric oxide NO levels in the arterial blood flow is being measured at least in part by the biosensor 100 at wavelengths in the range of 380-410 and in particular at $\lambda_1=390$ nm. Thus, the biosensor 100 measurements to determine the $L_{390\ nm}$ values are the first time NO levels in arterial blood flow have been measured directly in vivo. These and other aspects of the biosensor 100 are described in more detail herein with clinical trial results.

Embodiment—Determination of NO Levels at a Plurality of Wavelengths

Figure 11:
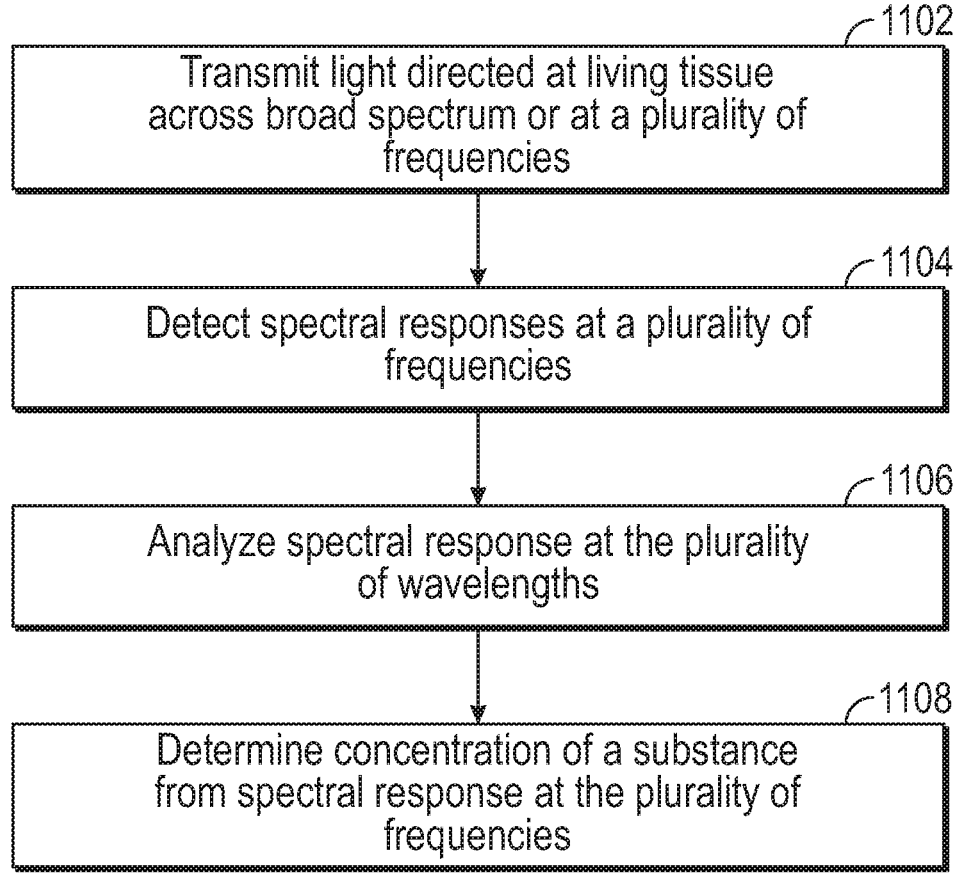
FIG. 11 illustrates a logical flow diagram of an exemplary method to determine levels of nitric oxide (NO) using the spectral response at a plurality of wavelengths.

FIG. 11 illustrates a logical flow diagram of an exemplary method 1100 to determine levels of NO using the spectral response at a plurality of wavelengths. The absorption coefficient may be higher at other wavelengths due to NO or NO isoforms or NO compounds. For example, the increased intensity of light at a plurality of wavelengths may be due to reflectance by NO or NO isoforms or other NO compounds in the arterial blood flow. Another method for determining NO levels may then be used by measuring the spectral response and determining L and R values at a plurality of different wavelengths of light. In this example then, NO level is determined over multiple wavelengths. An example for calculating the concentration of one or more substances over multiple wavelengths may be performed using a linear function, such as is illustrated herein below.

$$LN(I_{1-n}) = \Sigma_{i=0}^{n} \mu i * Ci$$

wherein, $I_{1-n}$=intensity of light at wavelengths $\lambda_{1-n}$ $\mu_n$=absorption coefficient of substance 1, 2, ... n at wavelengths $\lambda_{1-n}$ $C_n$=Concentration level of substance 1, 2, ... n When the absorption coefficients $\mu_{1-n}$ of NO or NOS isoforms or other NO compounds are known at the wavelengths $\lambda_{1-n}$, then the concentration level C of the substances may be determined from the spectral responses at the wavelengths $\lambda_{1-n}$ (and e.g., including a range of 1 nm to 50 nm around each of the wavelengths). The concentration level of NO may be isolated from the NOS isoforms or other NO compounds by compensating for the concentration of the hemoglobin compounds. Thus, using the spectral responses at multiple frequencies provides a more robust determination of the concentration level of NO.

In use, the biosensor 100 transmits light directed at skin tissue at a plurality of wavelengths or over a broad spectrum at 1102. The spectral response of light from the skin tissue is detected at 1104, and the spectral response is analyzed for a plurality of wavelengths (and in one aspect including a range of +/−10 to 50 nm around each of the wavelengths) at 1106. Then, the concentration level C of the substance may be determined using the spectral response at the plurality of wavelengths at 1108.

Figure 12:
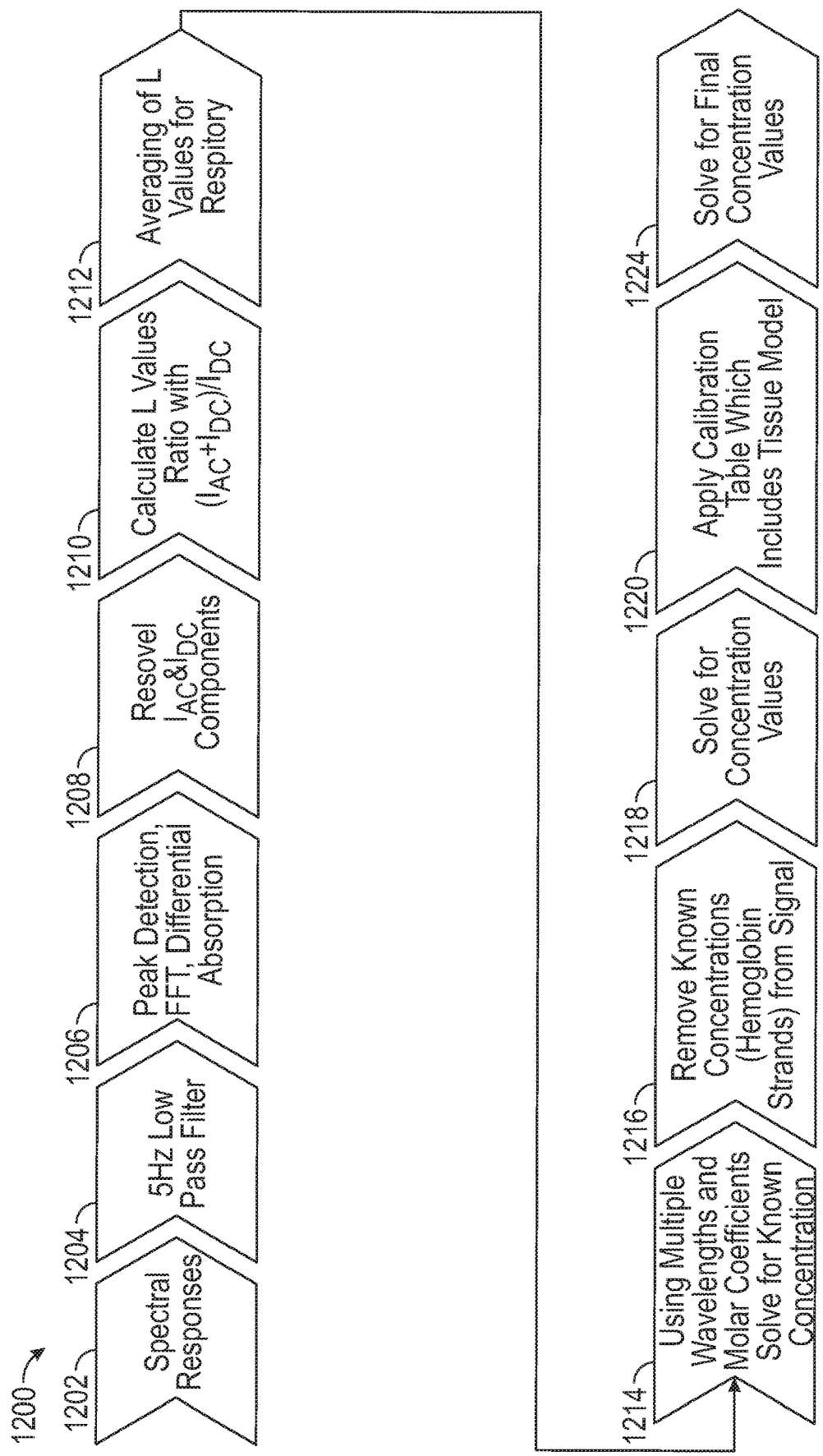
FIG. 12 illustrates a logical flow diagram of an exemplary method to determine levels of NO using the spectral response at a plurality of wavelengths in more detail.

FIG. 12 illustrates a logical flow diagram of an exemplary method 1200 to determine levels of NO using the spectral response at a plurality of wavelengths in more detail. The spectral responses are obtained at 1202. The spectral response signals include AC and DC components $I_{AC+DC}$. A low pass filter (such as a 5 Hz low pass filter) is applied to each of the spectral response signals $I_{AC+DC}$ to isolate the DC component of each of the spectral response signals $I_{DC}$ at 1204. The AC fluctuation is due to the pulsatile expansion of the arteriolar bed due to the volume increase in arterial blood. In order to measure the AC fluctuation, measurements are taken at different times and a peak detection algorithm is used to determine the diastolic point and the systolic point of the spectral responses at 1206. Fast Fourier transform (FFT) or differential absorption techniques may also be used to isolate the DC component of each spectral response signal. The various methods include one or more of: Peak & Valley (e.g., peak detection), FFT, and differential absorption. Each of the methods require different amounts of computational time which affects overall embedded computing time for each signal, and therefore can be optimized and selectively validated with empirical data through large clinical sample studies.

The $I_{AC+DC}$ and $I_{DC}$ components are then used to compute the L values at 1210. For example, a logarithmic function may be applied to the ratio of $I_{AC+DC}$ and $I_{DC}$ to obtain an L value for each of the wavelengths $L_{\lambda 1-n}$. Since the respiratory cycle affects the PPG signals, the L values may be averaged over a respiratory cycle and/or over another predetermined time period (such as over a 1-2 minute time period).

In an embodiment, NO isoforms may be attached in the blood stream to one or more types of hemoglobin compounds. The concentration level of the hemoglobin compounds may then need to be accounted for to isolate the concentration level of NO from the hemoglobin compounds. For example, nitric oxide (NO) is found in the blood stream in a gaseous form and also attached to hemoglobin compounds as described herein. Thus, the spectral responses obtained around 390 nm may include a level of the hemoglobin compounds as well as nitric oxide. The hemoglobin compound levels must thus be compensated for to isolate the nitric oxide levels. Multiple wavelengths and absorption coefficients for hemoglobin are used to determine a concentration of the hemoglobin compounds at 1214. This process is discussed in more detail herein below. Other methods may also be used to obtain a level of hemoglobin in the arterial blood flow as explained herein. The concentration of the hemoglobin compounds is then adjusted from the measurements to determine the level of NO at 1216. The R values are then determined at 1218.

To determine a level of NO, a calibration database is used that associates R values to levels of NO at 1220. The calibration database correlates the R value with an NO level. The calibration database may be generated for a specific patient or may be generated from clinical data of a large sample population. It is determined that the R values should correlate to similar NO levels across a large sample population. Thus, the calibration database may be generated from testing of a large sample of a general population.

In addition, the R values may vary depending on various factors, such as underlying skin tissue. For example, the R values may vary for spectral responses obtained from an abdominal area versus measurements from a wrist or finger due to the varying tissue characteristics. The calibration database may thus provide different correlations between the R values and NO levels depending on the underlying skin tissue characteristics.

The NO level is then obtained at 1224. The NO level may be expressed as mmol/liter, as a saturation level percentage, as a relative level on a scale, etc. In order to remove the hemoglobin concentration(s) from the original PPG signals, a mapping function may be created which is constructed through clinical data and tissue modeling. For example, known $SpO_2$ values in the infrared region and the same signals at the UV side of the spectrum are obtained. Then a linear inversion map can be constructed where the R values are input into a function and the desired concentration(s) can be determined. For example, a curve that correlates R values to levels may be tabulated. A polynomial equation with multiple factors can also be used to account for different R values to represent the linear inversion map. This correlation may be derived from validated clinical data.

For example, a regression curve that correlates R values and NO levels may be generated based on clinical data from a large general population. A polynomial may be derived from the curve and used to solve for an NO level from the R value. The polynomial is stored in the calibration database and may be used rather than using a calibration look-up table or curve.

Embodiment—Determination of a Concentration of Hemoglobin Compounds

The Beer-Lambert theory may be generalized for a multi-wavelength system to determine a concentration of known hemoglobin species using the following matrix notation:

$$\begin{bmatrix} dA_{\lambda 1}^{LB} \\ \vdots \\ dA_{\lambda n}^{LB} \end{bmatrix} = \begin{bmatrix} \Delta l_{\lambda 1} & \cdots & 0 \\ \vdots & \ddots & \vdots \\ 0 & \cdots & \Delta l_{\lambda n} \end{bmatrix} \begin{bmatrix} \varepsilon_{\lambda 1, HbX_1} & \cdots & \varepsilon_{\lambda 1, HbX_m} \\ \vdots & \ddots & \vdots \\ \varepsilon_{\lambda n, HbX_1} & \cdots & \varepsilon_{\lambda n, HbX_m} \end{bmatrix} \cdot \begin{bmatrix} HbX_1 \\ \vdots \\ HbX_m \end{bmatrix} \cdot c(Hb),$$

wherein $dA_\lambda^{LB}$ is a differential absorption within the Beer-Lambert model $\varepsilon_{\lambda n1, HbX1}$ is an extinction coefficient HbX are hemoglobin fractions $\Delta l\lambda$ is the optical path-length for wavelength $\lambda$ c(Hb) is the hemoglobin concentration This Beer-Lambert matrix equation for determining hemoglobin levels may be solved when m is equal or greater than n, e.g., which means that at least four wavelengths are needed to solve for four hemoglobin species. The spectral responses at these four wavelengths may be analyzed to determine the concentration of the plurality of hemoglobin species.

Figure 13:
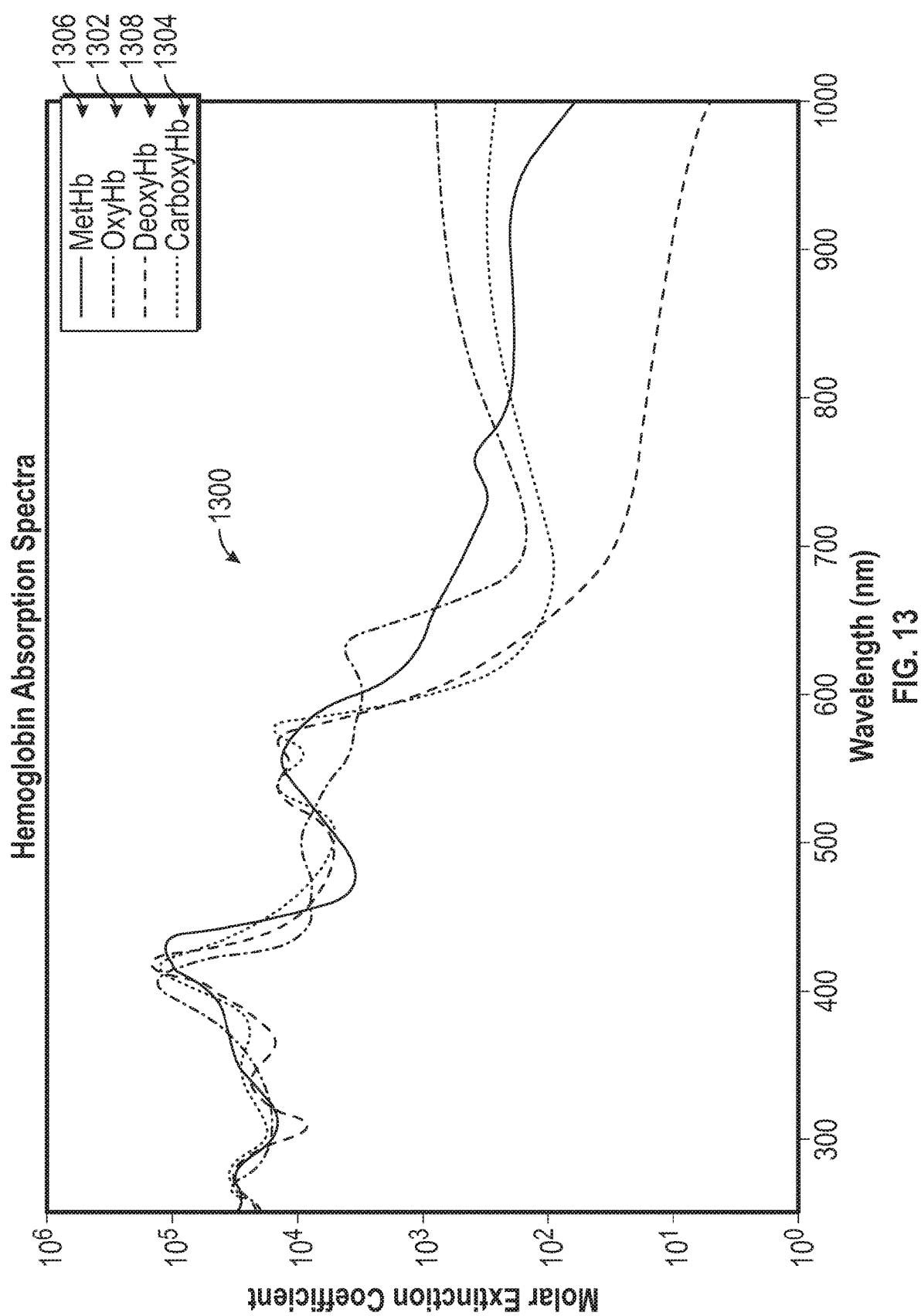
FIG. 13 illustrates a schematic block diagram of an exemplary embodiment of a graph illustrating the extinction coefficients over a range of frequencies for a plurality of hemoglobin species.

FIG. 13 illustrates a schematic block diagram of an exemplary embodiment of a graph 1300 illustrating the extinction coefficients over a range of frequencies for a plurality of hemoglobin species. The hemoglobin species include, e.g., Oxyhemoglobin [HbO₂ or OxyHb] 1302, Carboxyhemoglobin [HbCO or CarboxyHb] 1304, Methemoglobin [HbMet or MetHb] 1306, and deoxygenated hemoglobin (DeoxyHb or RHb) 1308. A method for determining the relative concentration or composition of hemoglobin species included in blood is described in more detail in U.S. Pat. No. 6,104,938 issued on Aug. 15, 2000, which is hereby incorporated by reference herein.

A direct calibration method for calculating hemoglobin species may be implemented by the biosensor 100. Using four wavelengths and applying a direct model for four hemoglobin species in the blood, the following equation results:

wherein $$HbX = \frac{a_1 * dA_1 + a_2 * dA_2 + a_3 * dA_3 + a_4 * dA_4}{b_1 * dA_1 + b_2 * dA_2 + b_3 * dA_3 + b_4 * dA_4}$$

$dA_\lambda$ is the differential absorption signal $a_n$ and $b_n$ are calibration coefficients The calibration coefficients $a_n$ and $b_n$ may be experimentally determined over a large population average. The biosensor 100 may include a calibration database to account for variances in the calibration coefficients $a_1$ and $b_1$ (or extinction coefficients) for the hemoglobin species for various underlying tissue characteristics.

A two-stage statistical calibration and measurement method for performing PPG measurement of blood analyte concentrations may also be implemented by the biosensor 100. Concentrations of MetHb, HbO₂, RHb and HbCO are estimated by first estimating a concentration of MetHb (in a first stage) and subsequently, if the concentration of MetHb is within a predetermined range, then the estimated concentration of MetHb is assumed to be accurate and this estimated concentration of MetHb is utilized as a "known value" in determining the concentrations of the remaining analytes HbO₂, RHb and HbCO (in a second stage). This method for determining a concentration of hemoglobin species using a two stage calibration and analyte measurement method is described in more detail in U.S. Pat. No. 5,891,024 issued on Apr. 6, 1999, which is hereby incorporated by reference herein.

The concentration of the hemoglobin compounds may thus be determined. The biosensor 100 compensates for the hemoglobin concentration in determinations to obtain the level of NO by the biosensor 100. Though several methods are described herein for obtaining a concentration of hemoglobin analytes, other methods or processes may be used by the biosensor 100 to determine the concentration of hemoglobin analytes or otherwise adjusting or compensating the obtained measurements to account for a hemoglobin concentration when determining the levels of NO in a blood stream.

Embodiment—Determination of NO Levels Using Shifts in Absorbance Peaks

In another embodiment, a level of NO may be obtained from measuring a characteristic shift in an absorbance peak of hemoglobin. For example, the absorbance peak for methemoglobin shifts from around 433 nm to 406 nm in the presence of NO. The advantage of the measurement of NO by monitoring methemoglobin production includes the wide availability of spectrophotometers, avoidance of sample acidification, and the relative stability of methemoglobin. Furthermore, as the reduced hemoglobin is present from the beginning of an experiment, NO synthesis can be measured continuously, removing the uncertainty as to when to sample for NO.

Figure 14:
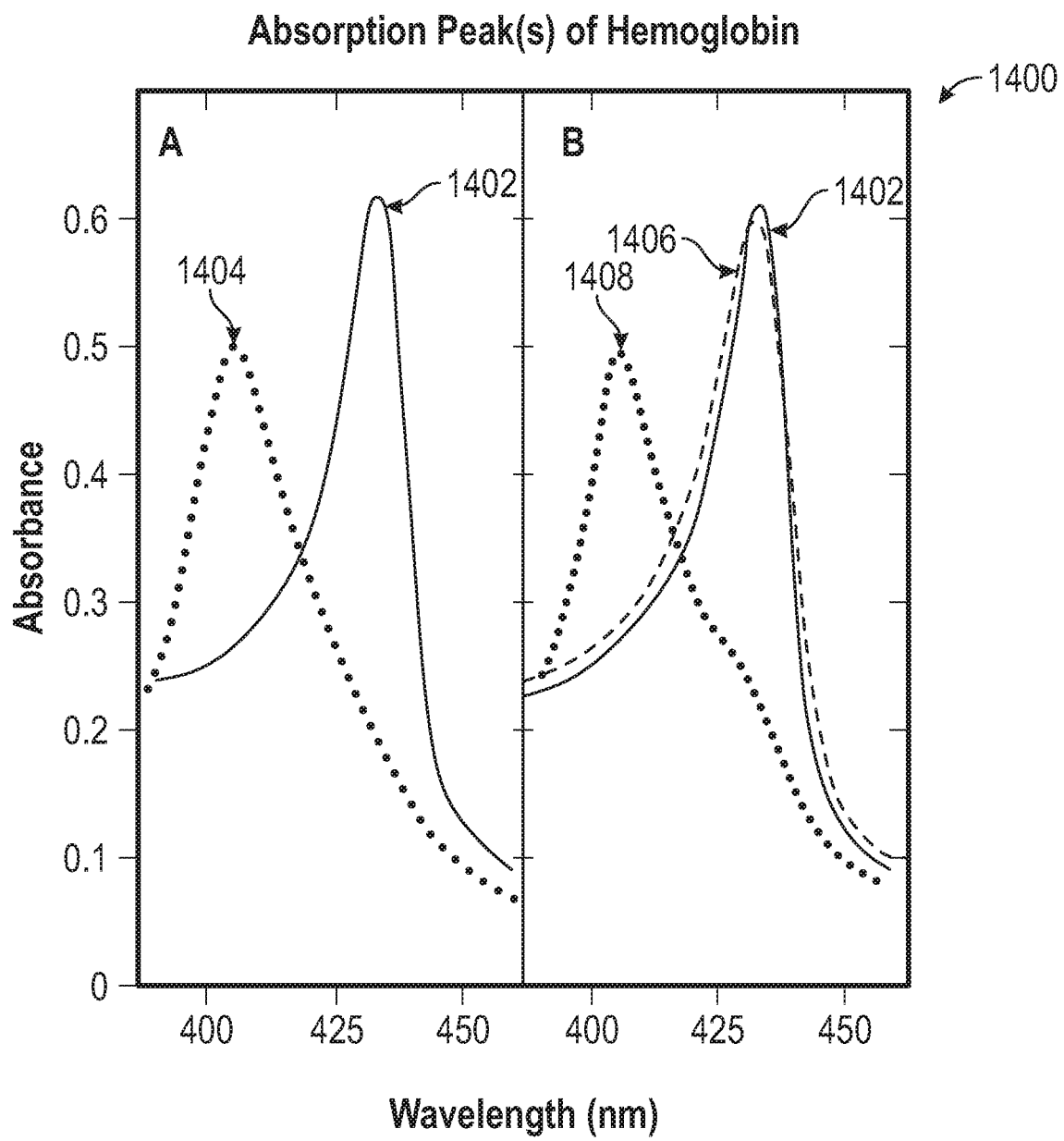
FIG. 14 illustrates a schematic block diagram of an exemplary embodiment of a graph illustrating a shift in absorbance peaks of hemoglobin in the presence of NO.

FIG. 14 illustrates a schematic block diagram of an exemplary embodiment of a graph 1400 illustrating a shift in absorbance peaks of hemoglobin in the presence of NO. In graph A, the curve 1402 illustrates the absorbance spectra of reduced hemoglobin. The addition of nitric oxide (NO) shifts the absorbance spectra curve 1402 to a lower wavelength curve 1404 due to the production of methemoglobin. In graph B, the absorbance spectra curve of reduced hemoglobin 1402 is again illustrated. Endothelial cells are then added and the absorbance spectra measured again. The curve 1406 illustrates that little change occurs in the absorbance spectra curve 1402 of reduced hemoglobin in the presence of unstimulated endothelial cells. The curve 1408 illustrates the production of methemoglobin when the same dose of endothelial cells was given after stimulation of EDRF synthesis by the ionophore.

Though the absorbance spectrums shown in the graph 1400 were measured using in vitro assays, the biosensor 100 may detect nitric oxide in vivo using PPG techniques by measuring the shift in the absorbance spectra curve of reduced hemoglobin 1402 in tissue and/or arterial blood flow. The absorbance spectra curve 1402 shifts with a peak from around 430 nm to a peak around 411 nm depending on the production of methemoglobin. The greater the degree of the shift of the peak of the curve 1402, the higher the production of methemoglobin and NO level. Correlations may be determined between the degree of the measured shift in the absorbance spectra curve 1402 of reduced hemoglobin to an NO level. The correlations may be determined from a large sample population or for a particular patient and stored in a calibration database. The biosensor 100 may thus obtain an NO level by measuring the shift of the absorbance spectra curve 1402 of reduced hemoglobin.

Figure 15:
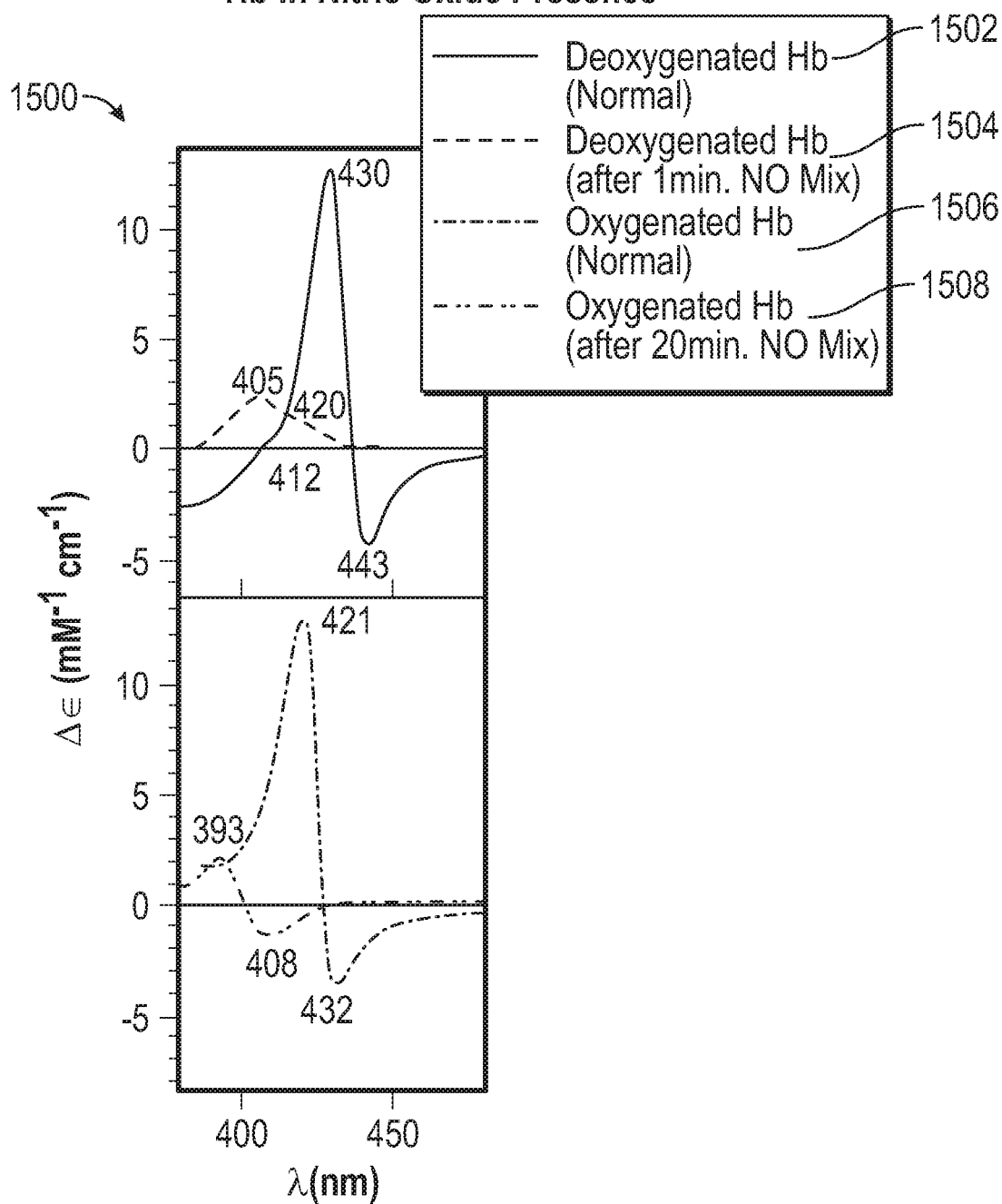
FIG. 15 illustrates a schematic block diagram of an exemplary embodiment of a graph illustrating a shift in absorbance peaks of oxygenated and deoxygenated hemoglobin (HB) in the presence of nitric oxide NO.

FIG. 15 illustrates a schematic block diagram of an exemplary embodiment of a graph 1500 illustrating a shift in absorbance peaks of oxygenated and deoxygenated hemoglobin (HB) in the presence of nitric oxide NO. The absorbance spectra curve 1502 of deoxygenated HB has a peak of around 430 nm. After a one minute time period of exposure to a nitric oxide mixture, the absorbance spectra curve 1504 of deoxygenated HB shifted to a peak of around 405 nm. In addition, the absorbance spectra curve 1506 of oxygenated HB has a peak around 421 nm. After a twenty minute time period of exposure to a nitric oxide mixture, the absorbance spectra curve 1508 of oxygenated HB shifted to a peak of around 393 nm. The Deoxygenated Hb has an absorption peak at 430 nm (curve 1502) and in the presence of NO has a peak shift to 405 nm (curve 1504). The Oxygenated Hb has absorption peak at 421 nm (curve 1506) in presence of NO has peak shift to 393 nm (curve 1508).

Though the absorbance spectrums shown in the graph 1500 were measured using in vitro assays, the biosensor 100 may obtain an NO level by measuring the shift of the absorbance spectra curve 1502 of deoxygenated hemoglobin and/or by measuring the shift of the absorbance spectra curve 1506 of oxygenated hemoglobin in vivo. The biosensor 100 may then access a calibration database that correlates the measured shift in the absorbance spectra curve 1502 of deoxygenated hemoglobin to an NO level. Similarly, the biosensor may access a calibration database that correlates the measured shift in the absorbance spectra curve 1506 of oxygenated hemoglobin to an NO level.

Figure 16:
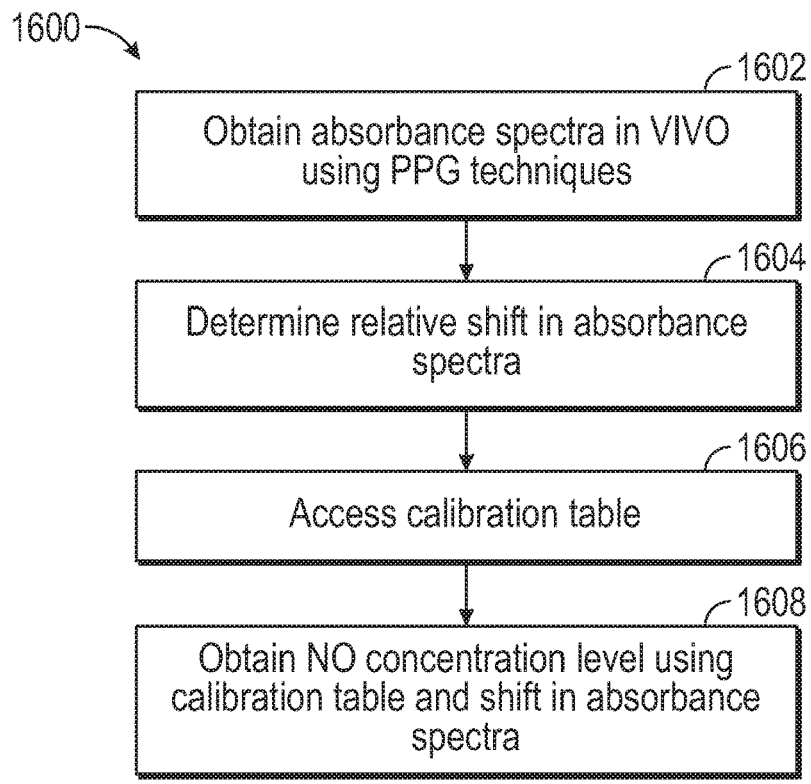
FIG. 16 illustrates a logical flow diagram of an exemplary embodiment of a method for measuring NO concentration levels in vivo using shifts in absorbance spectra.

FIG. 16 illustrates a logical flow diagram of an exemplary embodiment of a method 1600 for measuring NO levels in vivo using shifts in absorbance spectra. The biosensor 100 may obtain a concentration of NO by measuring shifts in absorbance spectra of one or more substances that interact with NO. For example, the one or more substances may include oxygenated and deoxygenated hemoglobin (HB). The PPG circuit 110 detects a spectral response at a plurality of wavelengths of the one or more substances that interact with NO at 1602. The biosensor 100 determines the relative shift in the absorbance spectra for the substance at 1604. For example, the biosensor 100 may measure the absorbance spectra curve 1502 of deoxygenated HB and determine its relative shift or peak between the range of approximately 430 nm and 405 nm. In another example, the biosensor 100 may measure the absorbance spectra curve of oxygenated HB and determine its relative shift or peak between 421 nm and 393 nm.

The biosensor 100 accesses a calibration database that correlates the relative shift in the absorbance spectra of the substance with a level of NO at 1606. The biosensor 100 may thus obtain an NO level using calibration database and the measured relative shift in absorbance spectra of the spectrum at 1608.

Figure 17:
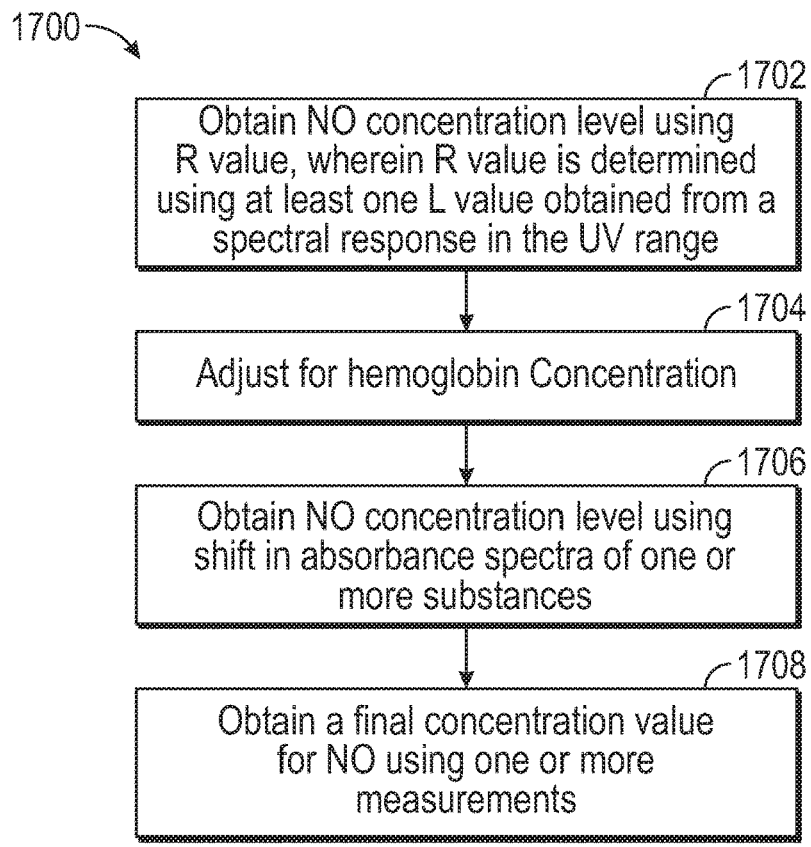
FIG. 17 illustrates a logical flow diagram of an exemplary embodiment of a method for measuring NO concentration levels using one or more measurement techniques.

FIG. 17 illustrates a logical flow diagram of an exemplary embodiment of a method 1700 for measuring NO levels using one or more measurement techniques. In an embodiment, the biosensor 100 is configured to determine a level of NO in vivo using PPG technology and one or more measurement techniques described herein. For example, the biosensor 100 may determine an R value using at least one L value obtained from a spectral response in the UV range at 1702. For example, the R value may be obtained using, e.g. an L Value in the range from 380-410 such as 390 nm or 395 nm. at $L_{390}/L_{940}$, at 1702 and accessing a calibration database that maps the R value to an NO level. In another example, the biosensor may determine NO level using absorption spectrum over a plurality of wavelengths and adjusting or compensating for hemoglobin concentrations at 1704. In another example, the biosensor 100 may determine the relative shift in the absorbance spectra for a substance (such as hemoglobin) and access a calibration database that correlates the relative shift in the absorbance spectra of the substance with a level of NO at 1706.

The biosensor 100 may use a plurality of these methods to determine a plurality of values for the level of NO at 1708. The biosensor 100 may determine a final concentration value using the plurality of values. For example, the biosensor 100 may average the values, obtain a mean of the values, etc.

Figure 18:
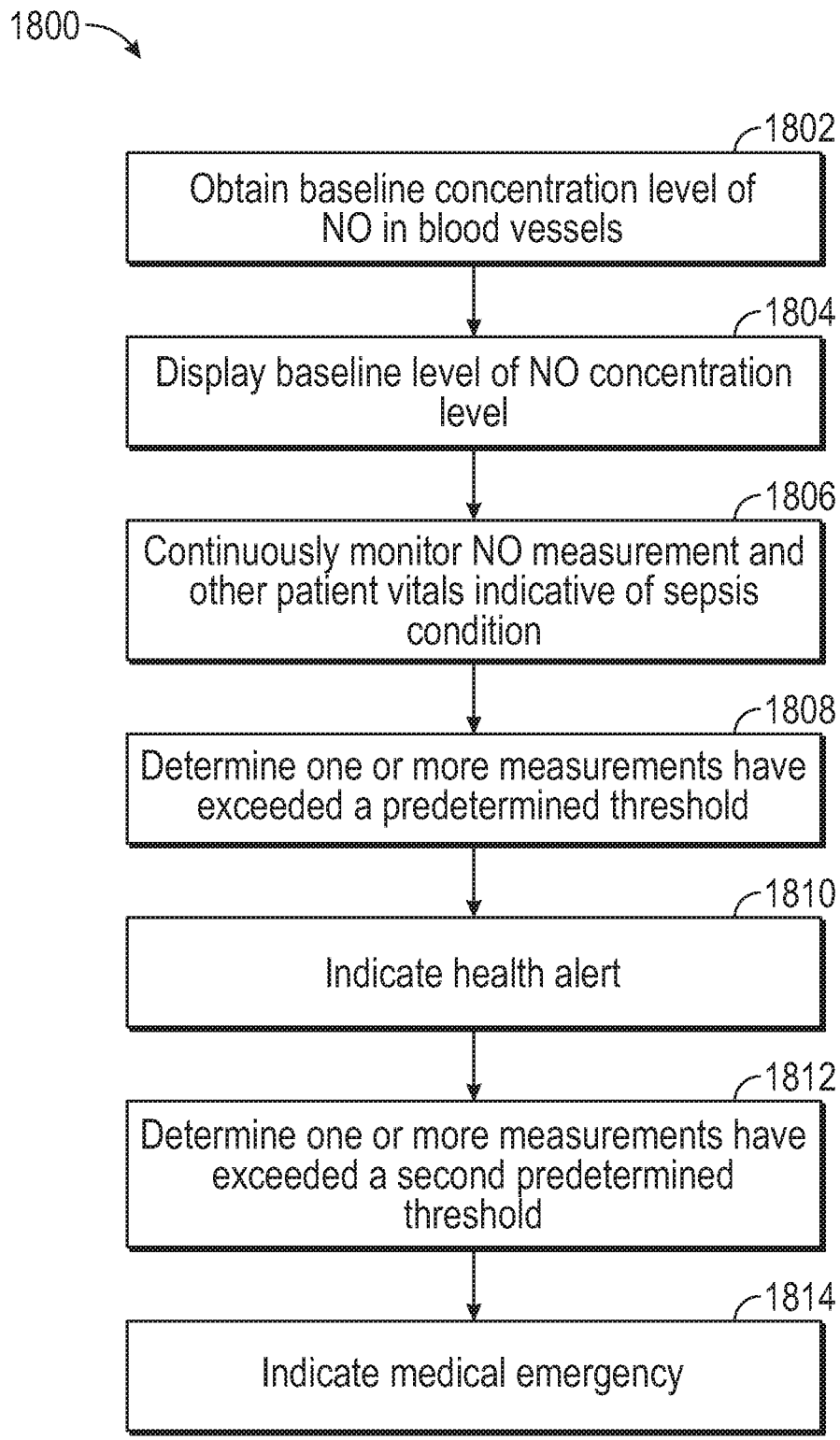
FIG. 18 illustrates a logical flow diagram of an embodiment of a method for providing a health alert for sepsis by monitoring NO measurements.

FIG. 18 illustrates a logical flow diagram of an embodiment of a method 1800 for providing a health alert for sepsis by monitoring NO measurements. In 1802, a baseline of an NO level in blood vessels is obtained. For example, the NO level may be obtained from an R value using $L_{\lambda 1}$=390 nm and $L_{\lambda 2}$=940 nm or an R value at $L_{\lambda 1}$=395 nm and $L_{\lambda 2}$=660 nm. In another embodiment, the NO measurement may be obtained using a value of $L_{\lambda 1}$=380 nm -400 nm and $L_{\lambda 2}$≥660 nm. The spectral response used to determine the value of $L_{\lambda 1}$=380 nm -400 nm may also be measuring other NO compounds, such as NO bonded to a plurality of hemoglobin species. The concentration of the plurality of hemoglobin species may be adjusted from the NO measurements and a calibration database used to obtain an NO level. In another example, the biosensor 100 may determine the relative shift in the absorbance spectra for a substance (such as hemoglobin) and access a calibration database that correlates the relative shift in the absorbance spectra of the substance with a level of NO.

In 1804, the biosensor 100 displays the baseline NO measurement and then non-invasively and continuously monitors the NO measurement in blood vessels at 1806. For example, the biosensor 100 may obtain the NO measurement at least once per minute or more frequently, such as every 10 seconds or 30 seconds, and continues to display the NO measurement. The biosensor 100 may also monitor other patient vitals indicative of sepsis condition, such as temperature, pulse, and respiration rate.

The NO measurement of the nitric oxide is compared to a first predetermined threshold. For example, normal ranges of the NO measurement from the baseline measurement are determined. Patient vitals may also be compared to predetermined thresholds. Depending on the comparison, one or more warnings are displayed. For example, the first predetermined threshold may be when the NO measurement has exceeded at least 10% of the baseline level of the NO measurement. A warning is displayed to indicate a health alert at 1810. A caregiver may then perform other tests to determine the cause of the elevated NO measurement, such as lactic acid blood test for sepsis.

The biosensor continues to monitor the NO measurement in blood vessels and compare the NO measurement to one or more predetermined thresholds. In 1812, it is determined that the NO measurement has exceeded a second predetermined threshold. For example, the NO measurement equals or exceeds at least 30% of a baseline level of the NO measurement. A warning to indicate a medical emergency is displayed at 1814. Due to the immediate danger of such high levels of NO measurement and dangers of septic shock, a request for immediate emergency treatment may be indicated. Though 10% and 30% are illustrated in this example, other percentages over the baseline level may also trigger warnings or alerts.

TABLE 2

| SpNO % | Interpretation (Nitric Oxide Levels) |
| --- | --- |
| 0-1.5% | Diabetic patients |
| 1.5-2% | Pre-Diabetic |
| 2-8% | Normal Patient |
| >10% | Clinically significant, consult medical control for direction |
| >30% | Assess for septic shock, provide high flow O2, and transport Consider emergency treatment |

Embodiment—Adjustments in Response to Positioning of the Biosensor

Figure 19:
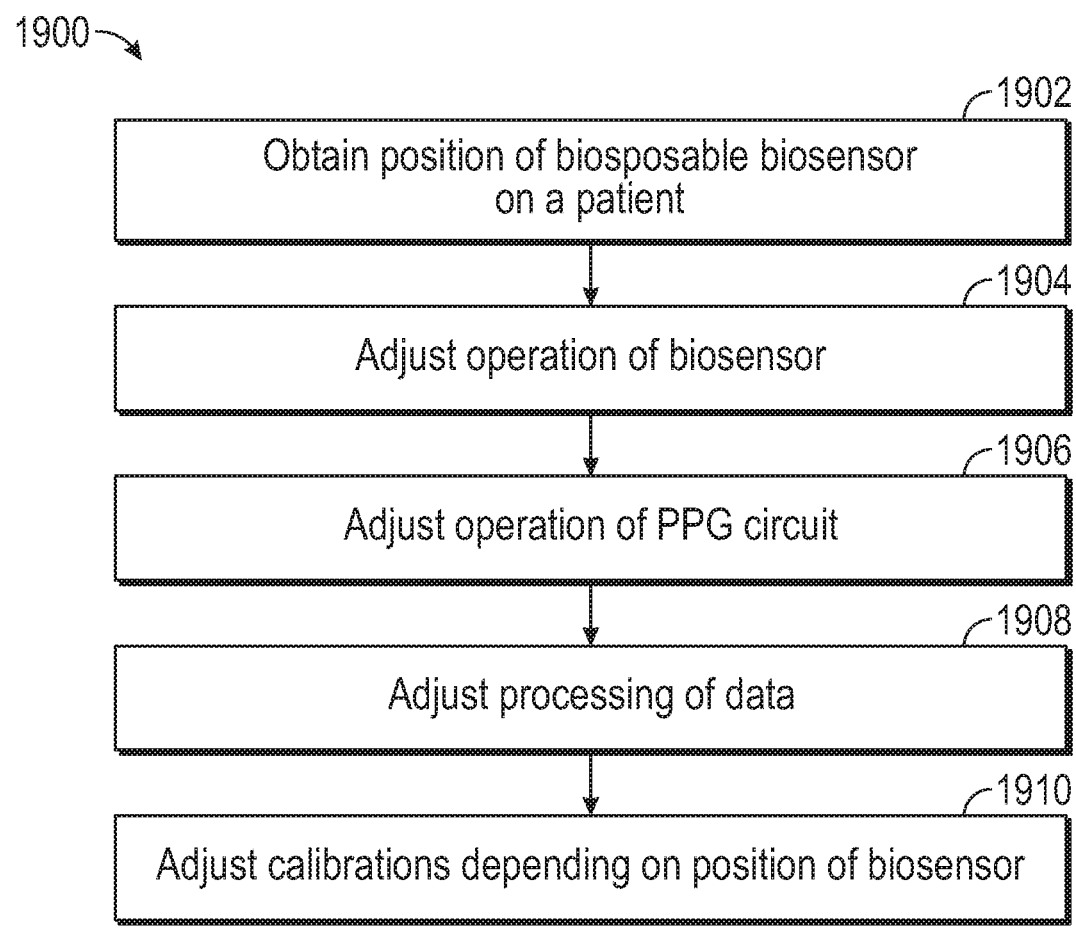
FIG. 19 illustrates a logical flow diagram of an embodiment of a method for adjusting operation of the biosensor in response to a position of the biosensor.

FIG. 19 illustrates a logical flow diagram of an embodiment of a method 1900 for adjusting operation of the biosensor 100 in response to a position of the biosensor 100. When the biosensor 100 is implemented in the patch 102 form factor, the biosensor 100 may be positioned over different areas of a patient. The skin tissue exhibits different underlying characteristics depending on the area of the body.

For example, the biosensor 100 may be positioned on or attached to, e.g. a hand, a wrist, an arm, forehead, chest, abdominal area, ear lobe, fingertip or other area of the skin or body or living tissue. The characteristics of underlying tissue vary depending on the area of the body, e.g. the underlying tissue of an abdominal area has different characteristics than the underlying tissue at a wrist. The operation of the biosensor 100 may need to be adjusted in response to its positioning due to such varying characteristics of the underlying tissue.

The biosensor 100 is configured to obtain position information on a patient at 1902. The position information may be input from a user interface. In another aspect, the biosensor 100 may determine its own positioning. For example, the PPG circuit 110 may be configured to detect characteristics of underlying tissue. The biosensor 100 then correlates the detected characteristics of the underlying tissue with known or predetermined characteristics of underlying tissue (e.g. measured from an abdominal area, wrist, forearm, leg, forehead, etc.) to determine its positioning. Information of amount and types of movement from an activity monitoring circuit implemented within the biosensor 100 may also be used in the determination of position.

In response to the determined position and/or detected characteristics of the underlying tissue, the operation of the biosensor 100 is adjusted at 1904. For example, the biosensor 100 may adjust operation of the PPG circuit 110 at 1906. The article, "Optical Properties of Biological Tissues: A Review," by Steven L. Jacques, Phys. Med. Biol. 58 (2013), which is hereby incorporated by reference herein, describes wavelength-dependent behavior of scattering and absorption of different tissues. The PPG circuit 110 may adjust a power of the LEDs or a frequency or wavelength of the LEDs based on the underlying tissue. The biosensor 100 may adjust processing of the data at 1908. For example, an absorption coefficient may be adjusted when determining a level of a substance based on Beer-Lambert principles due to the characteristics of the underlying tissue.

In addition, the calibrations utilized by the biosensor 100 may vary depending on the positioning of the biosensor at 1908. For example, the calibration database may include different table or other correlations between R values and NO level depending on position of the biosensor. Due to the different density of tissue and vessels, the R value obtained from measurements over an abdominal area may be different than measurements over a wrist or forehead. The calibration database may thus include different correlations of the R value and NO level depending on the underlying tissue. Other adjustments may also be implemented by the biosensor 100 depending on predetermined or measured characteristics of the underlying tissue.

The biosensor 100 is thus configured to obtain position information and perform adjustments to its operation in response to the position information.

Figure 20:
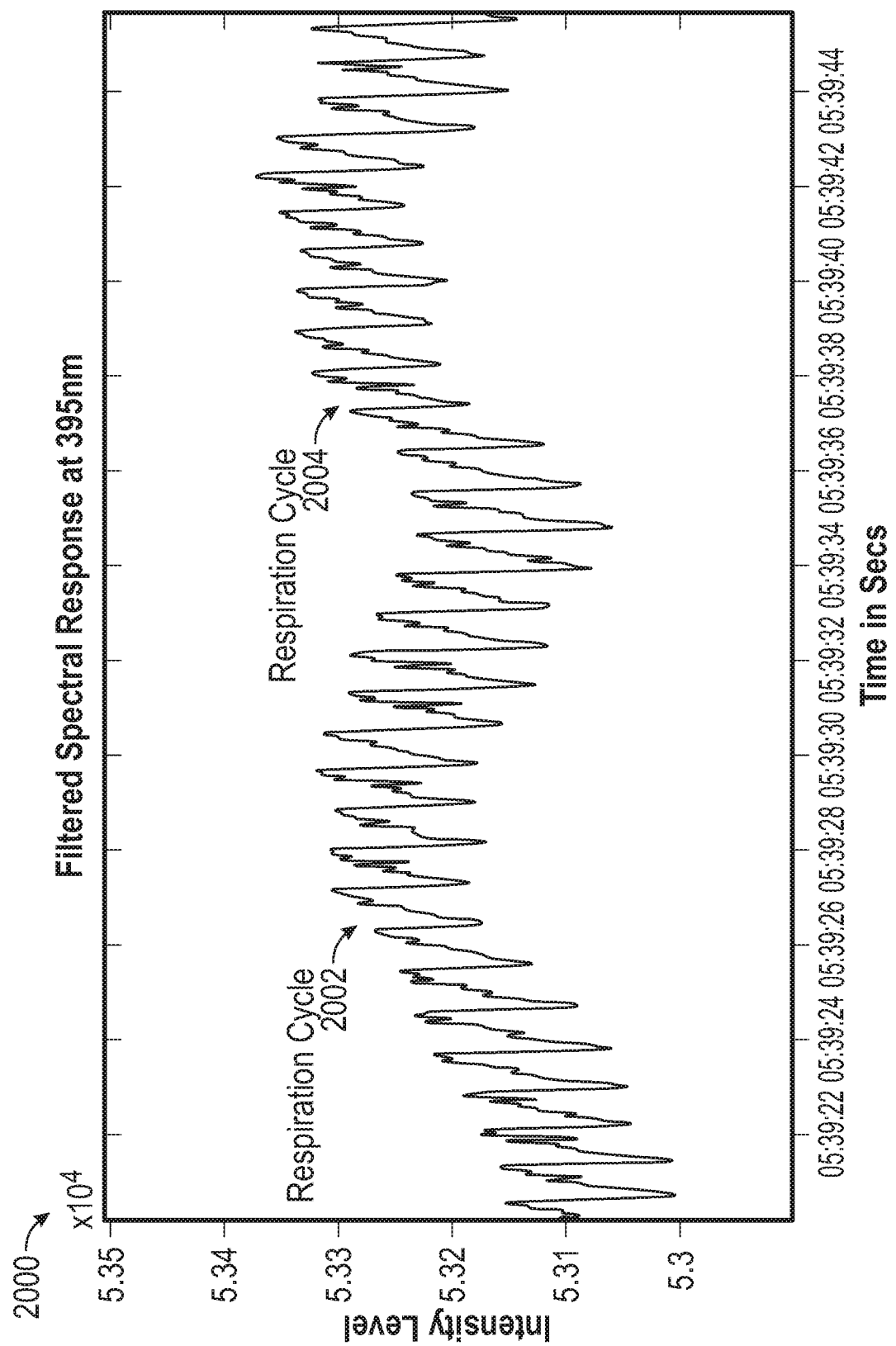
FIG. 20 illustrates a schematic drawing of an exemplary embodiment of results of a filtered spectral response obtained using an embodiment of the biosensor from a patient.

FIG. 20 illustrates a schematic drawing of an exemplary embodiment of results of a filtered spectral response 2000 obtained using an embodiment of the biosensor 100 from a patient. The spectral response 2000 was obtained at a wavelength of around 395 nm and is filtered by the biosensor 100 using digital signal processing techniques to eliminate noise and background interference to obtain the filtered spectral response 2000. A first respiration cycle 2002 and a second respiration cycle 2004 may be seen in the low frequency intensity fluctuation of the filtered spectral response 2100. Due to this fluctuation in intensity during respiratory cycles, the obtained L values may be averaged over a plurality of respiratory cycles or over a predetermined time period including a plurality of respiratory cycles, such as 1-2 minutes. In addition, the respiration rate of the patient may be obtained from measuring the periodicity of the low frequency cycles.

A low pass filter (such as a 5 Hz low pass filter) is applied to the filtered spectral response 2100 ($I_{AC+DC}$) to obtain the DC component of the spectral response $I_{DC}$. Rather than using a low pass filter, fast Fourier transform or other functions may also be used to isolate the DC component of the filtered spectral response 2000. The $I_{AC}$ signal is generated from the filtered spectral response and the signal $I_{DC}$. The AC component is the fluctuation due to the pulsatile expansion and contraction of the arteriolar bed as the volume of arterial blood increases and decreases due to the pulse rate. In order to measure the AC fluctuation, measurements are taken at different times and a peak detection algorithm is used to determine the diastolic point and the systolic point of the filtered spectral response. Rather than using a low pass filter, fast Fourier transform or other functions may also be used to isolate the DC component of the filtered spectral response to obtain $I_{AC}$. A pulse rate may also be obtained from the $I_{AC}$ signal.

Figure 21:
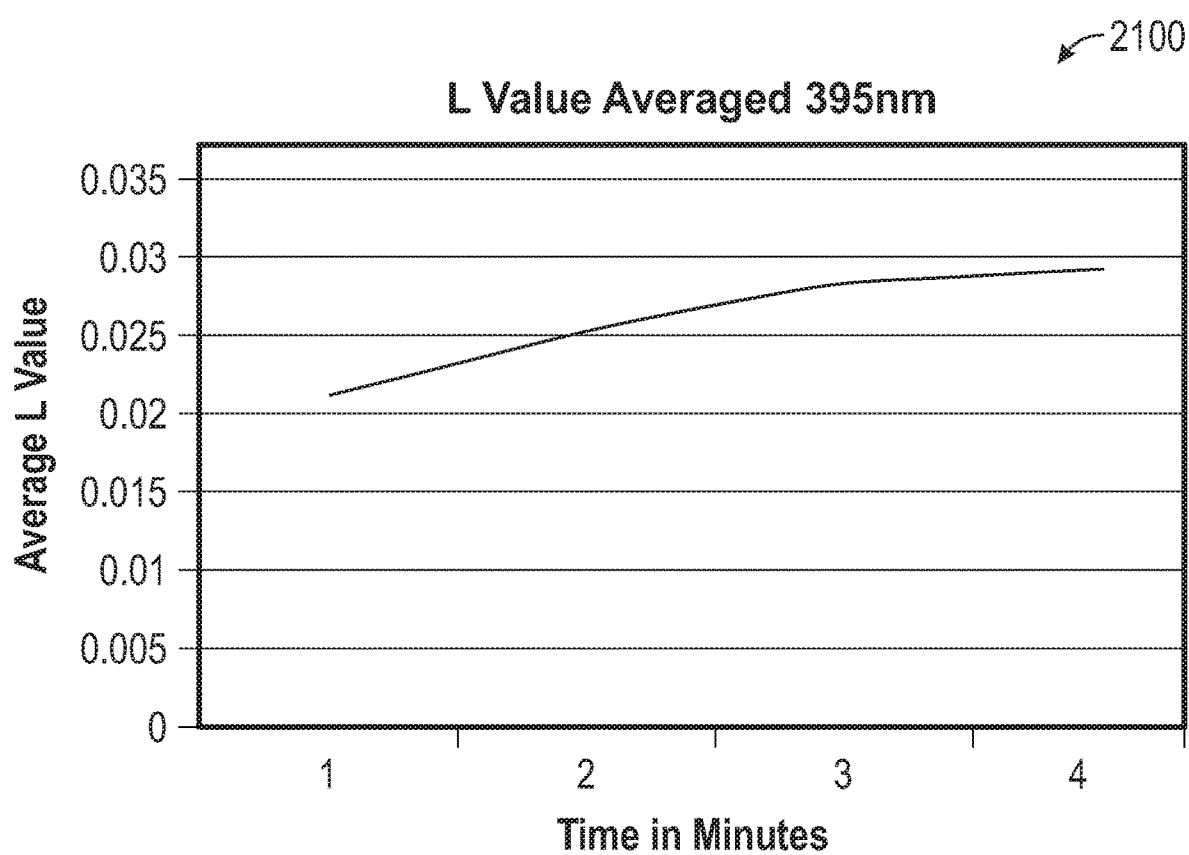
FIG. 21 illustrates a schematic drawing of an exemplary embodiment of results of L values obtained over a time period.

FIG. 21 illustrates a schematic drawing of an exemplary embodiment of results of averaged L values 2100. In this embodiment, the L values are obtained using spectral response from an LED at 395 nm in the UV range. Other wavelengths may be implemented in a UV range, such as from 380-410 nm. This range of wavelengths has a high absorption coefficient for NO compounds. The filtered spectral response $I_{AC}$ and $I_{DC}$ signal components are used to compute L values 2400. The L values are affected by the respiratory cycle as previously described. Thus, the L values 2100 shown in FIG. 21 are averaged over two or more respiratory cycles. Alternatively, the L values 2100 may be averaged over a predetermined time period (such as a 1-2 minute time period) that includes a plurality of respiratory cycles. As shown in FIG. 21, the averaged L values 2100 fluctuate between 0.2 and 0.3 over a three minute time period.

The averaged L values may be used as an NO measurement for baseline measurements of NO or to provide alerts based on NO measurements as well. For example, when the averaged $L_{395}$ exceeds 10% of the baseline value, e.g. such as exceeds 0.3 by over 10%, then an alert may be provided by the biosensor 100. When the averaged $L_{395}$ exceed 30% of the baseline value, e.g. such as exceeds 0.3 by 30% or more, then another alert of a medical emergency may be provided by the biosensor 100. Alternatively, the baseline value of the averaged L value for an individual may be based on observations of a healthy general population over a period of hours or days.

Figure 22:
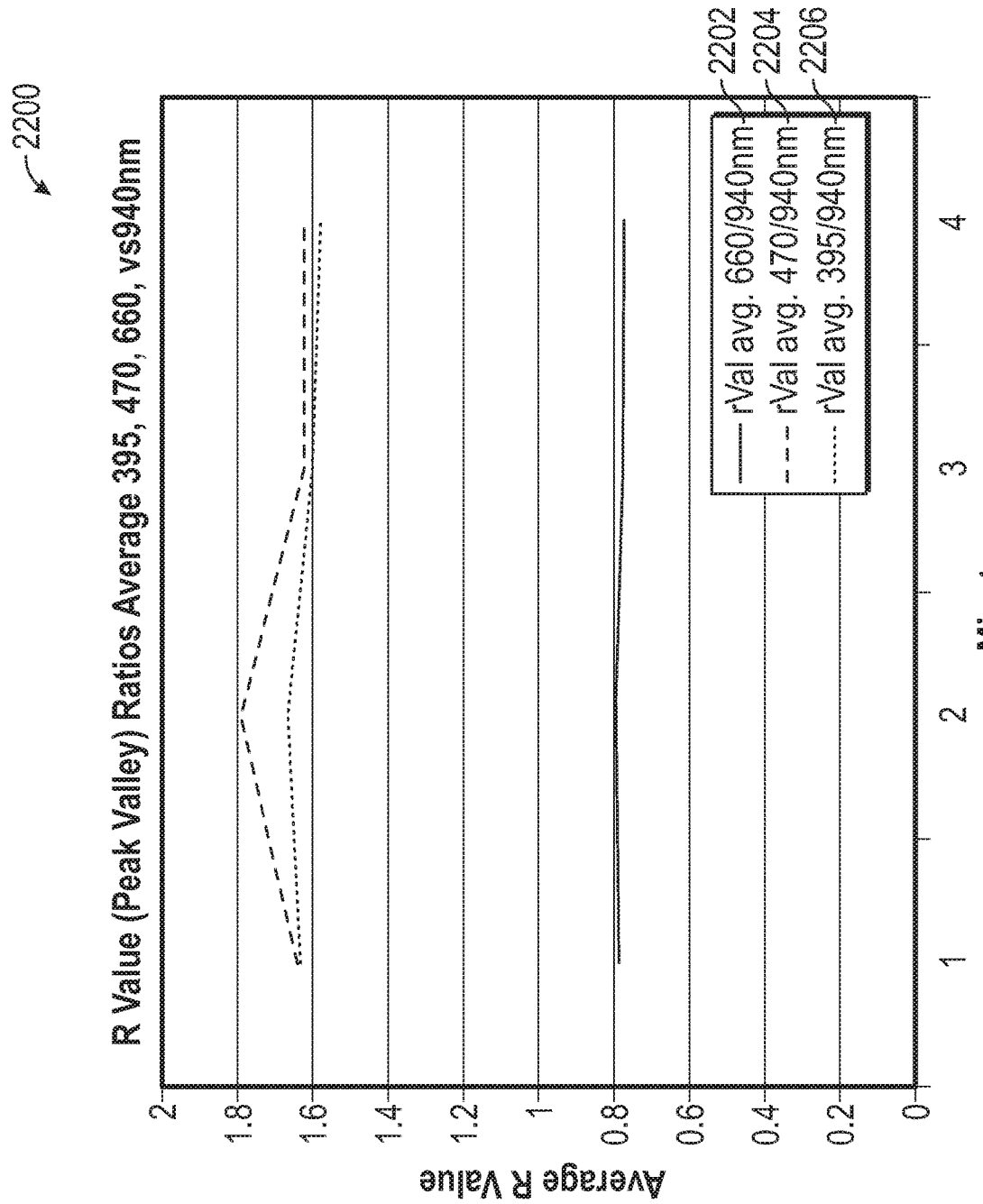
FIG. 22 illustrates a schematic drawing of an exemplary embodiment of results of averaged R values.

FIG. 22 illustrates a schematic drawing of an exemplary embodiment of results of averaged R values 2200. In this embodiment, the R value is a ratio of the averaged $L_{395\ nm}$ values and $L_{940\ nm}$ values:

$$\text{Ratio } R = \frac{L395}{L940}$$

The averaged R values 2200 may be obtained from averaging the Ratio R over a predetermined time period or may be calculated from the averaged L values. As shown in FIG. 22, the averaged R values 2206 at 395/940 nm wavelengths fluctuate between 1.68 and 1.58 over a three minute time period. The averaged R values 2204 at 479/940 nm wavelengths fluctuate between 1.68 and 1.8 over a three minute time period. The averaged R values 2202 at 660/940 nm wavelengths fluctuate between 0.8 and 0.78 over a three minute time period.

The averaged R values may be used as an NO measurement for baseline measurements of NO or to provide alerts based on NO measurements as well. For example, when the averaged R value exceeds 10% of the baseline value, e.g. such as exceeds 1.68 by over 10%, then an alert may be provided by the biosensor 100. When the averaged R value exceed 30% of the baseline value, e.g. such as exceeds 1.68 by 30% or more, then another alert of a medical emergency may be provided by the biosensor 100. Alternatively, the baseline value of the averaged R value for an individual may be based on observations of a healthy general population over a period of hours or days. A mean or average of the R values may be calculated to obtain a final R value or one of the methods may be preferred depending on the positioning of the biosensor or underlying tissue characteristics.

Figure 23A:
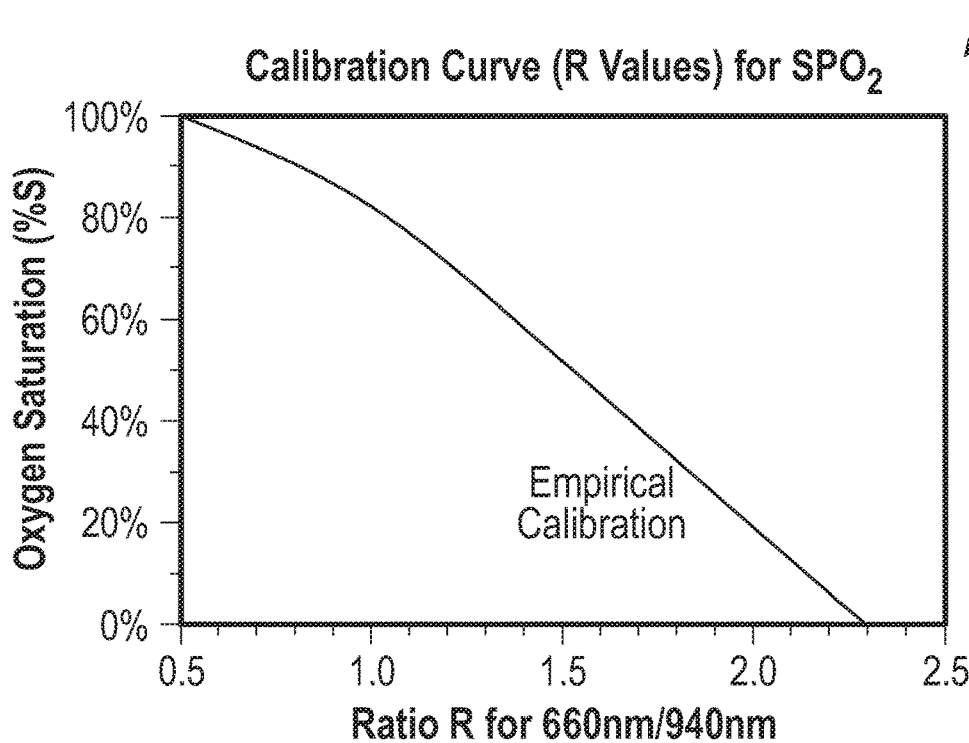
FIG. 23A illustrates a schematic drawing of an exemplary embodiment of a calibration curve for correlating oxygen saturation levels (SpO2) with R values.

FIG. 23A illustrates a schematic drawing of an exemplary embodiment of an empirical calibration curve 2300 for correlating oxygen saturation levels ($SpO_2$) with R values. The calibration curve 2300 may be included as part of the calibration database for the biosensor 100. For example, the R values may be obtained for $L_{660\ nm}/L_{940\ nm}$. In an embodiment, the biosensor 100 may use the 660 nm wavelength to determine $SpO_2$ levels, e.g. rather than IR wavelength range. The 660 nm wavelength has been determined in unexpected results to have good results in measuring oxygenated hemoglobin, especially in skin tissue with fatty deposits, such as around the abdominal area.

Figure 23B:
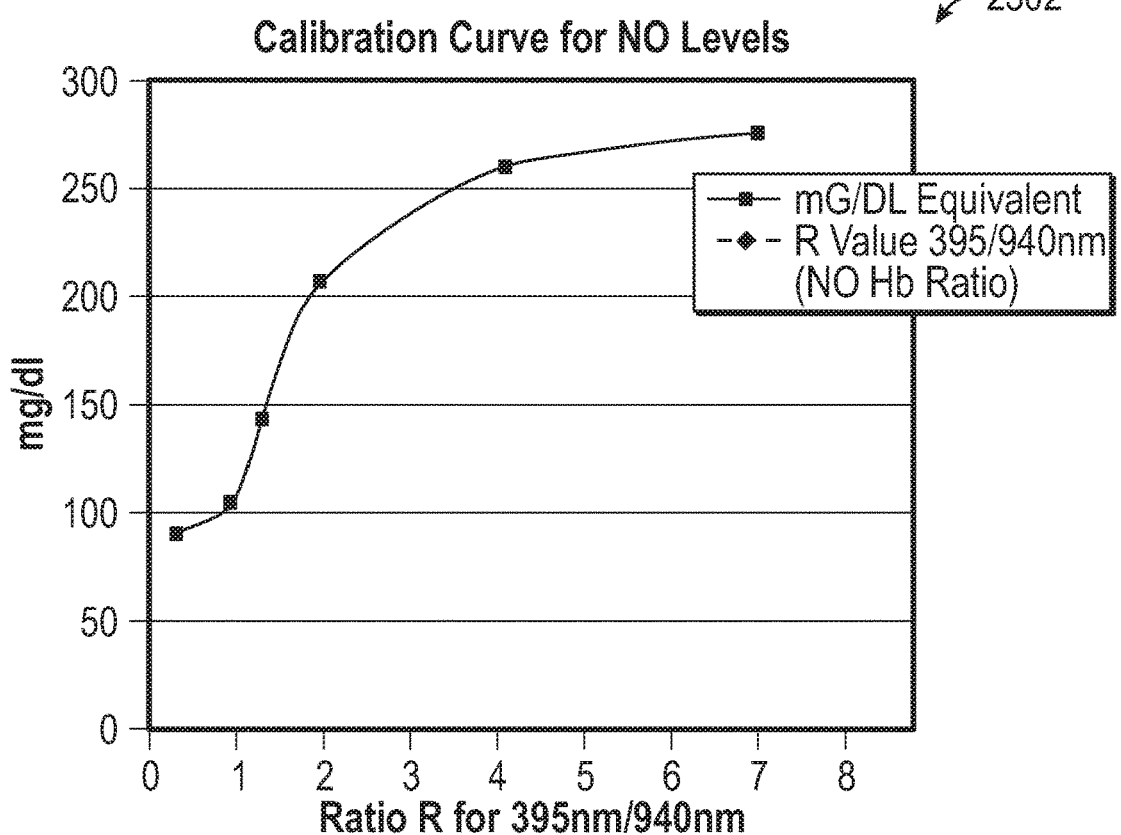
FIG. 23B illustrates a schematic drawing of an exemplary embodiment of a calibration curve for correlating for correlating NO levels (mg/dl) with R values.

FIG. 23B illustrates a schematic drawing of an exemplary embodiment of an empirical calibration curve 2302 for correlating NO levels (mg/dl) with R values. The calibration curve 3002 may be included as part of the calibration database for the biosensor 100. For example, the R values may be obtained from measurements of $L_{395\ nm}/L_{940\ nm}$ for a general population and the NO levels also measured using one or more other techniques for verification to generate such a calibration curve 2302. This calibration curve 2302 is based on limited clinical data and is for example only. Additional calibration curves 2302 may also be derived from measurements of a general population of patients at one or more different positions of the biosensor 100. For example, a first calibration curve may be obtained at a forehead, another for an abdominal area, another for a fingertip, etc.

From the clinical trials, the L values obtained at wavelengths around 390 nm (e.g. 380-410) are measuring NO levels in the blood flow and surrounding tissue. The R value for $L_{390}/L_{940\ nm}$ may thus be used to obtain NO levels in the pulsating blood flow. From the clinical trials, it seems that the NO levels are reflected in the R values obtained from $L_{390\ nm}/L_{940\ nm}$ and wavelengths around 390 nm such as $L_{395}/L_{940}$. The NO levels may thus be obtained from the R values, e.g. using a calibration database that correlates the R value with known level of NO for the patient or for a large general population or using neural network techniques described herein.

In other embodiments, rather than $L_{\lambda1}$=390 nm, the L value may be measured at wavelengths in a range from 410 nm to 380 nm, e.g., as seen in the graphs wherein $L_{\lambda1}$=395 nm is used to obtain a level of NO. In addition, $L_{\lambda2}$ may be obtained at any wavelength at approximately 660 nm or above. Thus, R obtained at approximately $L\lambda1$=380 nm-400 nm and $L\lambda2 \geq 660$ nm may also be obtained to determine levels of NO.

Figure 24:
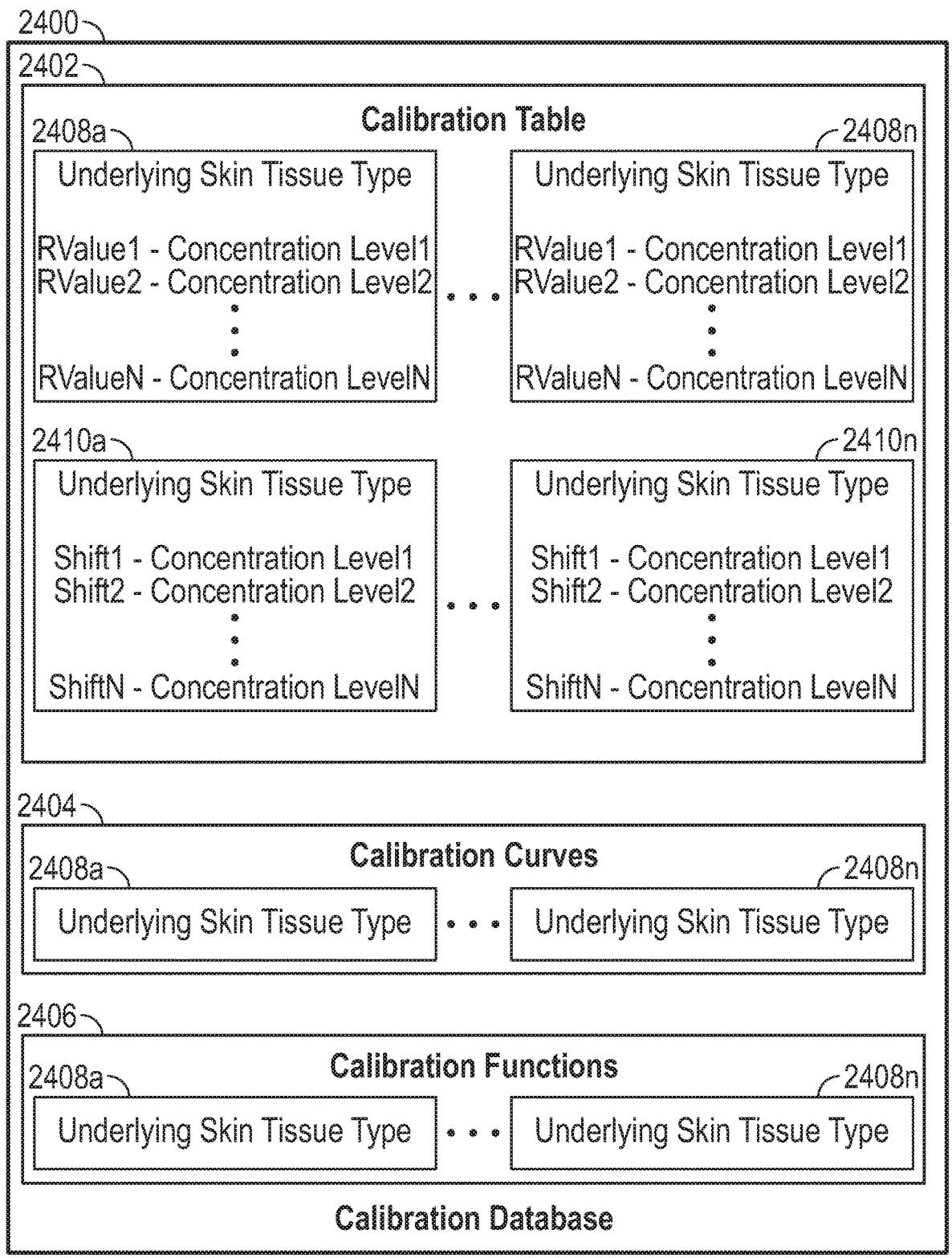
FIG. 24 illustrates a schematic block diagram of an embodiment of a calibration database.

FIG. 24 illustrates a schematic block diagram of an embodiment of a calibration database 2400. The calibration database 2400 includes one or more calibration tables 2402, calibration curves 2404 or calibration functions 2406 for correlating obtained values to levels of NO. The level of NO may be expressed in the calibration tables 2402 as units of mmol/liter, as a saturation level percentage (SpNO %), as a relative level on a scale (e.g., 0-10), etc.

The calibration tables 2402 include one or more calibration tables for one or more underlying skin tissue type 2408*a-n*. In one aspect, the calibration tables 2408 correlate an R value to a level of NO for a plurality of underlying skin tissue types. For example, a first set of tables 2408*a-n* may correlate R values to NO levels for a wrist area, a second table for an abdominal area, a third table for a forehead area, etc.

In another aspect, a set of calibration tables 2410*a-n* correlate an absorption spectra shift to a level of NO for a plurality of underlying skin tissue types. For example, a first table 2410 may correlate a degree of absorption spectra shift of oxygenated hemoglobin to NO levels for a wrist area, a second table 2410 for an abdominal area, a third table 2410 for a forehead area, etc. The degree of shift may be for the peak of the absorbance spectra curve of oxygenated hemoglobin from around 421 nm. In another example, the set of tables 2410 may correlate a degree of absorption spectra shift of deoxygenated hemoglobin to NO levels for a wrist area, a second table for an abdominal area, a third table for a forehead area, etc. The degree of shift may be for the peak of the absorbance spectra curve of deoxygenated hemoglobin from around 430 nm.

The calibration database 2402 may alternatively or additionally include a set of calibration curves 2404 for a plurality of underlying skin tissue types. The calibration curves may correlate L values or R values or degree of shifts to levels of NO.

The calibration database 2402 may also include calibration functions 2406. The calibration functions 2406 may be derived (e.g., using regressive functions) from the correlation data from the calibration curves 2404 or the calibration tables 2402. The calibration functions 2406 may correlate L values or R values or degree of shifts to levels of NO for a plurality of underlying skin tissue types.

Embodiment—Screening and Prediction of Sepsis

Figure 25:
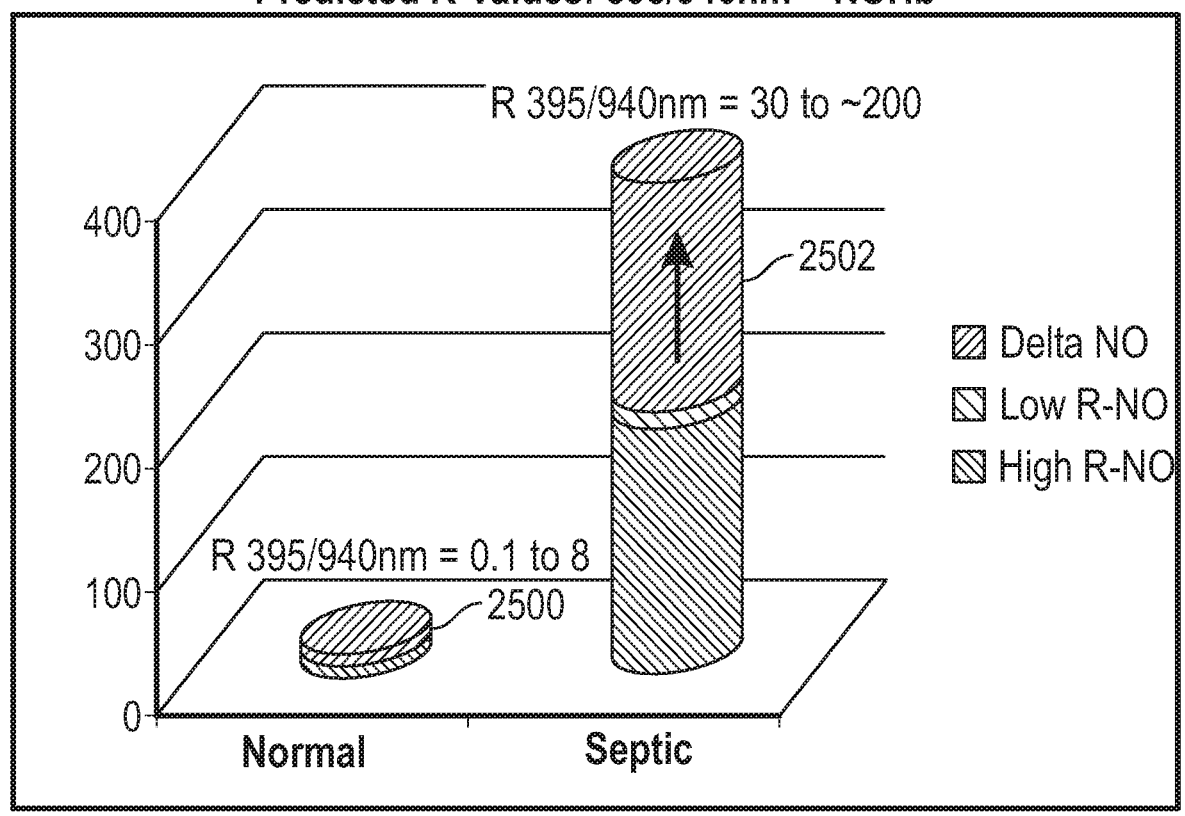
FIG. 25 illustrates a schematic block diagram of an embodiment of predetermined thresholds of NO measurements for detecting a risk of sepsis.

FIG. 25 illustrates a schematic block diagram of an embodiment of predetermined thresholds of NO measurements for detecting a risk of sepsis. In one initial clinical trial, R values were obtained from patients without sepsis and from patients diagnosed with sepsis using a lactic acid blood test. In this clinical trial, the $R_{395/940}$ value for a person without a septic condition was in a range of 0.1-8. In addition, it was determined that an R value of 30 or higher was indicative of a septic condition and that an R value of 8-30 was indicative of a risk of sepsis in a patient. In general, an R value of 2-3 times a baseline R value was indicative of a risk of sepsis in a patient.

For example, in the example shown in FIG. 25, a range of the R value 2500 is from 0.1 to 8 for a person without a septic condition. The range 2502 of the R value for a person with a sepsis condition is from 30 to 200 or above. These ranges are based on preliminary clinical data and may vary as described hereinbelow with additional clinical data. In addition, a position of the biosensor, pre-existing conditions of a patient or other factors may alter the numerical values of the ranges of the R values described herein.

The R values are determined by measuring an NO level directly using a wavelength in the UV range with high absorption coefficient for NO or NO compounds, e.g. in a range of 380 nm-410 nm. These R values have a large dynamic range from 0.1 to 300 and above. The percentage variance of R values in these measurements is from 0% to over 3,000%. The R values obtained by the biosensor 100 are thus more sensitive and may provide an earlier detection of septic conditions than blood tests for serum lactate or measurements based on MetHb.

For example, an optical measurement of MetHb in blood vessels is in a range of 0.8-2. This range has a difference of 1.1 to 1.2 between a normal value and a value indicating a septic risk. So, these measurements based on MetHb have less than a 1% percentage variance. In addition, during a septic condition, MetHb may become saturated due to the large amount of NO in the blood vessels. So, an optical measurement of MetHb alone or other hemoglobin species alone is not able to measure these excess saturated NO levels. The R values determined by measuring NO level directly using a wavelength in the UV range are thus more sensitive, accurate, have a greater dynamic range and variance, and provide an earlier detection of septic conditions.

A healthcare provider may determine to continue monitoring or perform additional tests or begin a treatment for infection. For $R_{395/940}$ values at 30 or above, the biosensor 100 may be configured to indicate an alert indicating a high health risk or onset of sepsis. A healthcare provider may determine to immediately begin an aggressive treatment for infection or perform additional treatments and intervention.

Figure 26:
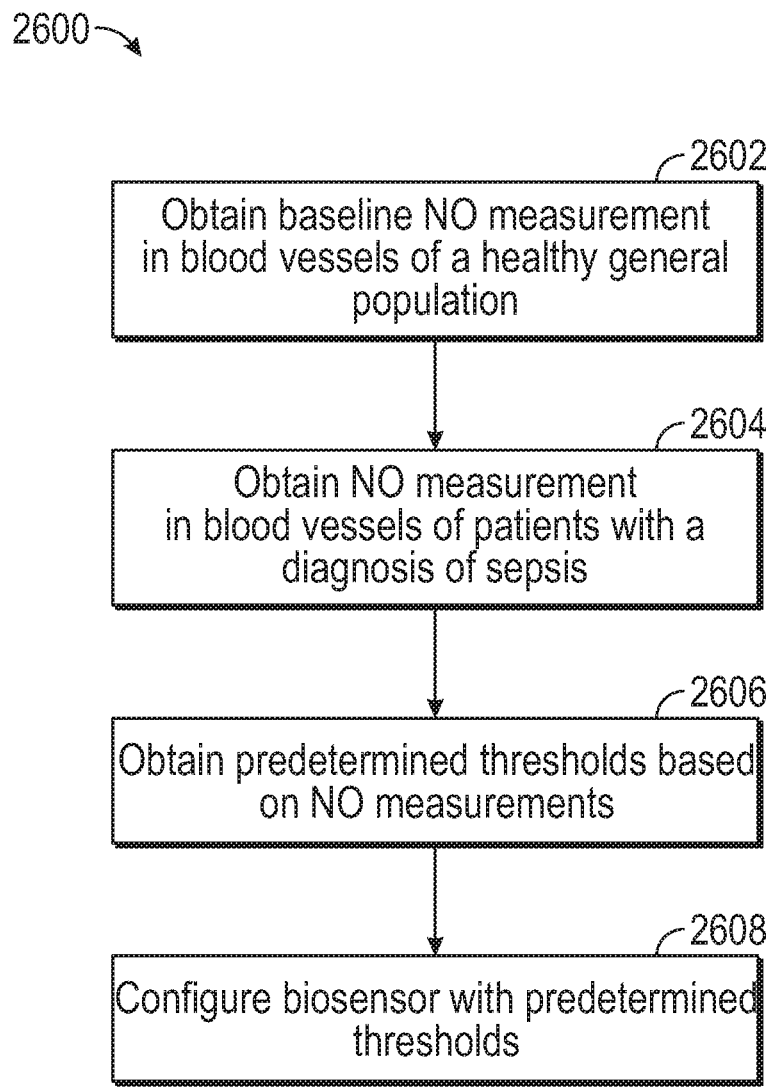
FIG. 26 illustrates a logical flow diagram of an embodiment of a method for determining predetermined thresholds for health alert indicators for sepsis.

FIG. 26 illustrates a logical flow diagram of an embodiment of a method 2600 for determining predetermined thresholds for health alert indicators for sepsis. A baseline NO measurement in blood vessels of a healthy general population is obtained in 2602. For example, the biosensor 100 may obtain R values or other NO measurements using the biosensor 100. For example, the biosensor 100 may measure an $L_{395}$ value, R value or determine a relative level, umol/liter concentration, saturation level, etc. for a general population over a period of time, such as hours or days. These NO measurements are then used (such as determining an average, mean, normalized range) to determine a baseline NO measurement or a baseline range of NO measurements. The measurement of NO levels include levels of one or more of: gaseous NO, nNOS levels and/or other NO compounds, either measured as a relative level, concentration in mmol/liter, percentage, etc.

The NO measurement in blood vessels is then obtained for a patients with a diagnosis of sepsis at 2604. For example, the biosensor 100 may obtain R values or other NO measurements (such as an $L_{395}$ value or a relative level, umol/liter concentration, saturation level, etc.) for patients diagnosed with sepsis using traditional blood tests, such as serum lactate blood tests. The biosensor 100 may monitor the patients throughout the diagnosis and treatment stages. The NO measurements are then then used (such as determining an average, mean, normalized range) to determine a range of values that indicate a septic condition in a patient.

Predetermined thresholds may then be obtained from the NO measurements at 2606. For example, a threshold value indicative of a non-septic condition may be obtained. A threshold value for a septic condition may also be obtained. The biosensor 100 is then configured with the predetermined thresholds for the NO measurement at 2608.

The predetermined thresholds may be adjusted based on an individual patient's pre-existing conditions. For example, a patient with diabetes may have lower R values. A baseline NO value for a patient may also be determined based on monitoring of the patient during periods without infections. The predetermined thresholds stored in the bio sensor 100 may then be adjusted based on any individual monitoring and/or pre-existing conditions.

In addition, the predetermined thresholds may be determined and adjusted based on positioning of the biosensor 100. For example, different R values or other NO measurements may be obtained depending on the characteristics of the underlying tissue, such as tissue with high fatty deposits or with dense arterial blood flow. The thresholds and other configurations of the biosensor 100 may thus be adjusted depending on the underlying skin tissue, such as a forehead, chest, arm, leg, finger, abdomen, etc.

Figure 27:
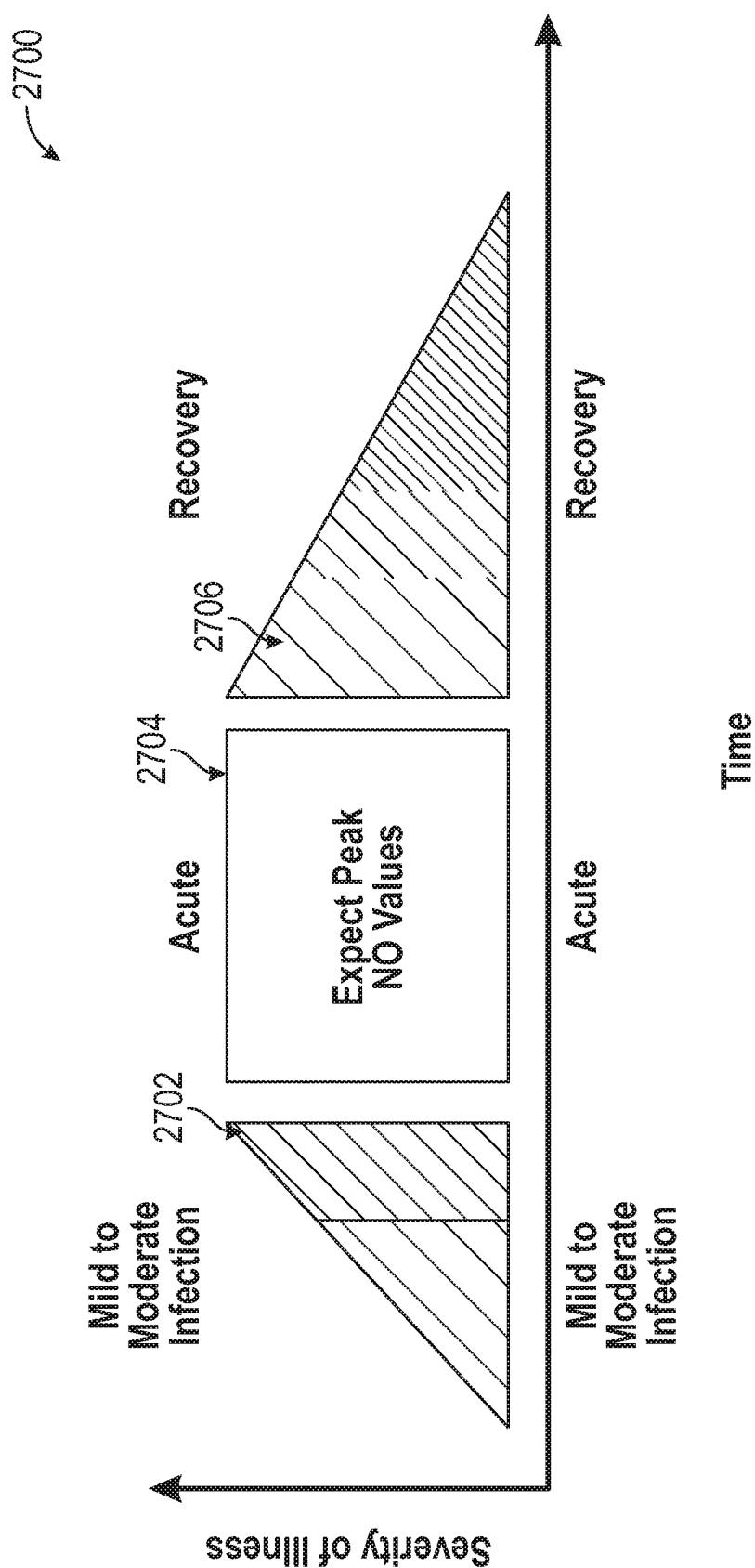
FIG. 27 illustrates a graphical representation of an embodiment of severity levels of an infection.

FIG. 27 illustrates a graphical representation of an embodiment of severity levels 2700 of an infection. In an embodiment, the biosensor 100 may provide screening for infections, such as sepsis, COVID-19, influenza, pneumonia, or other types of infection. The biosensor 100 may detect an activated immune response and determine a severity level of the infection based a measurement of NO levels and other factors. For example, in a first stage 2702, a patient may have a mild or moderate infection but is not septic (e.g., not considered septic per standard blood tests of serum lactate). The patient may have a confirmed or suspected infection but not presenting with SIRS. An immune response is present but may be mild or moderate. In clinical trials, the biosensor 100 was able to detect increased levels of NO and/or spikes or pulses of high levels of NO indicating this first stage of an immune response to an infection.

In a second stage 2704, a patient is diagnosed with sepsis (e.g. diagnosed with standard laboratory tests of blood samples). Sepsis is diagnosed with two or more of the SIRS symptoms and a confirmed or suspected infection. Prior definitions of severe sepsis included signs of organ dysfunction, hypotension or blood tests confirming an elevated lactate level. For example, factors in diagnosis of severe sepsis include elevated lactate, creatinine greater than 2 mg/dL, Bilirubin greater than 2 mg/dL, platelet count less than 100,000 and urine output less than 0.5 mL/kg/hr or more than 2 hours despite fluid resuscitation. The newer definitions of sepsis include a SOFA score based on several similar parameters shown in TABLE 1 above. Nearly all patients with severe sepsis require treatment in an intensive care unit (ICU).

Septic shock ensues from severe sepsis and persistent low blood pressure despite fluid resuscitation. In some studies, it appears that on average, approximately 30% of patients diagnosed with severe sepsis do not survive. Up to 50% of survivors suffer from post-sepsis syndrome. Until a cure for sepsis is found, early detection and treatment is essential for survival and limiting disability for survivors.

In clinical trials, the biosensor 100 was able to detect peak NO levels. In addition, the biosensor 100 was able to determine an onset of sepsis or severe sepsis using measurements of NO indicating increased levels of NO. For example, using a measurement of NO levels, the biosensor 100 was able to determine that sepsis would present in the patient up to 2-8 hours before the clinical diagnosis of sepsis in the patient from laboratory tests. These measurements of NO levels included pulses or spikes indicating high levels of NO.

In a third stage 2706, a patient is in recovery from sepsis or severe sepsis or septic shock. The levels of NO measured by the biosensor 100 are returning to normal levels, and the peaks are not as frequent or have lower levels. The biosensor 100 detects the decreased immune response, recovery from the infection, and a return to health.

In addition to the measurement of NO levels, the biosensor 100 was able to detect other parameters in diagnosing SIRS, sepsis, severe sepsis and septic shock. For example, the biosensor 100 is able to detect heart rate and respiration rate from one or more PPG signals at one or more wavelengths. The biosensor 100 is thus able to detect when the heart rate is greater than 90 bpm and respiratory rate is greater than 20 breaths/min., both of which are indications of SIRS and sepsis. The biosensor 100 may also include a temperature sensor. Another factor in SIRS and sepsis is a temperature of greater than 38 degrees C. or less than 36 degrees C. The biosensor 100 may also detect an estimate of mean arterial pressure changes indicate of hypotension in severe sepsis. The biosensor 100 may also detect oxygen saturation levels, and measurement of creatinine levels, liver enzyme levels, and bilirubin levels. Using one or more of these factors, the biosensor 100 may screen a patient to detect an infection in a patient, such as sepsis, COVID-19, flu, pneumonia, etc. and determine a severity level (SIRS, sepsis, severe sepsis, acute sepsis, recovery). The biosensor 100 may also determine a hybrid qSOFA score or hybrid SOFA score using one or more of these factors.

Figure 28C:
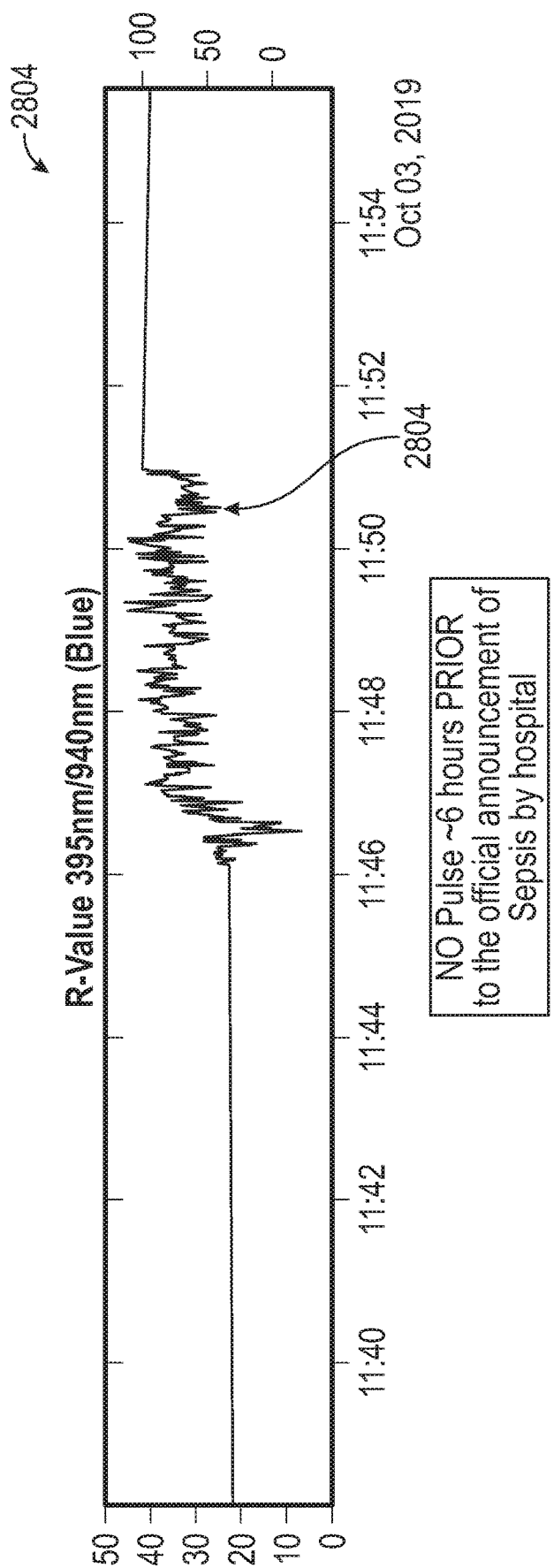
FIG. 28C illustrates a graphical representation of clinical data of the sample patient showing an expansion of a second period in FIG. 28A.

FIG. 28A illustrates a graphical representation of clinical data 2800 of a sample patient over a four day time period. A second clinical trial was conducted to test the biosensor 100 and included 122 patients with a portion of the patients being diagnosed as septic using conventional blood tests, such as CBC complement, serum lactate levels or other tests. FIGS. 28A-C illustrates clinical data 2800 obtained from a sample patient A002 diagnosed with sepsis.

An embodiment of the biosensor 100 obtained PPG signals at a first wavelength of 395 nm and a second wavelength of 940 nm from the patient periodically over the four day time period and determined R values 395 nm/940 nm shown as line 2804. As shown at a first period 2806 during DAY 1, the $R_{395/940}$ values were in a range greater than 20 indicating a high risk of sepsis. At a second period 2808 during DAY 2, the biosensor 100 obtained R values 2804 with large pulses over 30. These large pulses of NO levels obtained by the biosensor 100 indicate that the patient presents with a septic condition. However, it took over 6 hours later after these PPG signals were detected during this second period 2808 for the hospital to obtain a sepsis diagnosis using convention blood tests.

Conventional blood tests for sepsis may thus provide insufficient advance warning of deteriorating patient health or the onset of potentially serious physiological conditions resulting from sepsis (such as SIRS). In conventional tests, blood samples must be taken and laboratory tests performed to obtain a diagnosis of sepsis. For example, blood tests for sepsis include CBC complement, serum lactate levels or other types of tests. These types of blood tests are usually only performed once a day and are invasive, non-continuous, costly, and time consuming. Since sepsis is very dangerous and may escalate to be life threatening conditions quickly, this diagnosis process is not sufficient for early warning of the onset of sepsis or severe sepsis.

FIG. 28B illustrates a graphical representation of clinical data 2800 of the sample patient showing an expansion of the first period 2806 in FIG. 28A. The period 2806 includes about 5 minutes and shows the R value 2804 during this period 2806. The R value ranges from approximately 12 to over 20 during this five minute period 2806.

FIG. 28C illustrates a graphical representation of clinical data 2800 of the sample patient showing an expansion of the second period 2808 in FIG. 28A. The period 2808 includes about 5 minutes and shows the R value 2804 during this period 2808. The R value ranges from approximately 5 to over 40 during this five minute period 2808.

The biosensor 100 is thus able to monitor a patient continuously or periodically throughout the day and obtain a measurement of NO levels in less than five minutes. The biosensor 100 may thus detect an increase in NO levels indicating an escalation of the infection prior to detection by conventional blood tests. Using the measurement of NO levels by the biosensor 100, a patient may be screened within 5 minutes to determine a presence of an infection and a severity level of the infection.

In addition to levels of NO, the biosensor 100 may also consider other factors in the screening and monitoring of patients for infections. For example, FIG. 28A depicts the phase difference 2802 between the PPG signal at 395 nm and the PPG signal at 940 nm. The two wavelengths have different penetrations of depth in tissue of a patient such that changes in the phase difference between the two wavelengths indicates changes in the circulation of vessels in the skin tissue, such as the microvasculature circulation or micro-circulation. For example, the patient received a vasoconstriction medication during period 2806 and period 2808. The phase difference increased after both periods indicating decreased circulation due to the effects of the vasoconstrictor.

The cardiovascular system faces great challenge during systemic inflammatory response syndrome (SIRS). The response of the cardiovascular system (tachycardia and hypotension) has been used as important components in the list of diagnostic criteria for SIRS and sepsis. Thus, the phase difference between the two PPG signals may provide additional information for the screening and monitoring for SIRS and sepsis and other infections, such as COVID-19, influenza, pneumonia, etc.

FIGS. 29A-F illustrate graphical representations of clinical data obtained from a plurality of patients in the second clinical trial. The second clinical trial included n=122 patients admitted and hospitalized. The patients had any of two: an infection with a total SOFA score equal to 0 or 1 and/or a patient without sepsis prone to the development of sepsis (CCI>2). The mean age was 75±13 years and the gender distribution was male=46%, female=54%. A 33% portion of the patients were diabetic and 60% presented with one or more infection(s). Of the 122 patients, 11% of the cases were verified as septic during the clinical trial using conventional blood tests.

The patients shown in FIG. 29 were diagnosed at some point during the clinical trial with sepsis using conventional laboratory tests such as, CBC complement, serum lactate levels or other tests. The biosensor 100 obtained PPG signals from the patients during a sample window of approximately five minutes at two hour intervals. Each interval in the graphs 29A-F indicates the average or mean $R_{395/940}$ value obtained during the corresponding sample window of testing by the biosensor 100.

Figure 29A:
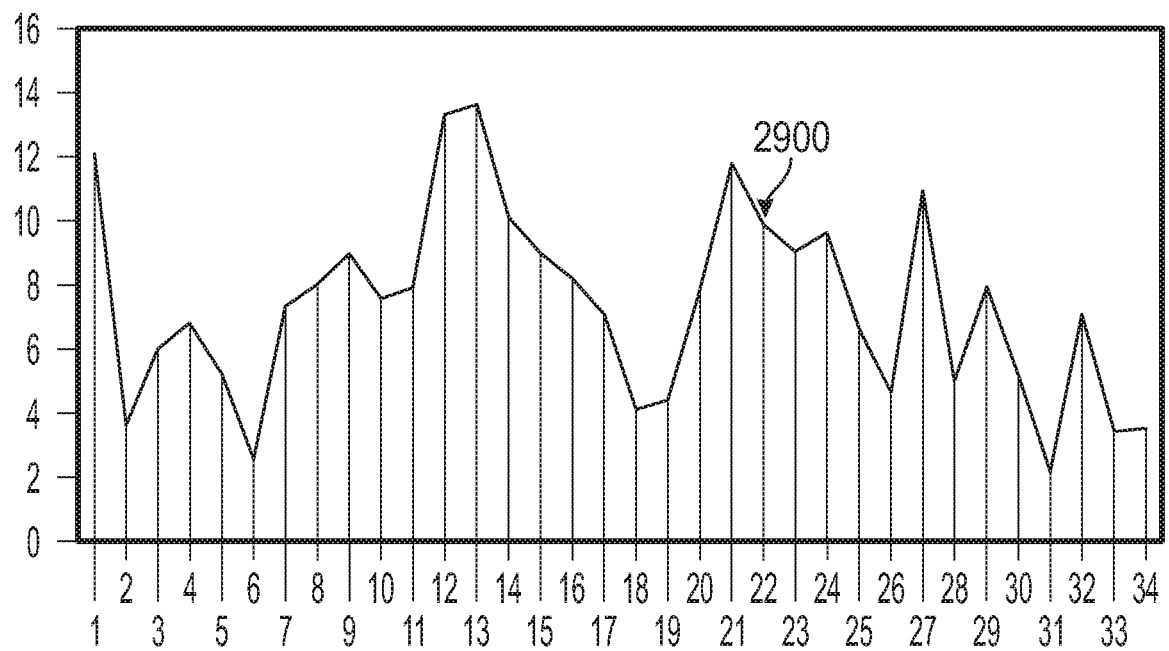
FIG. 29A illustrates a graphical representations of clinical data obtained from one of a plurality of patients in a second clinical trial.
Figure 29B:
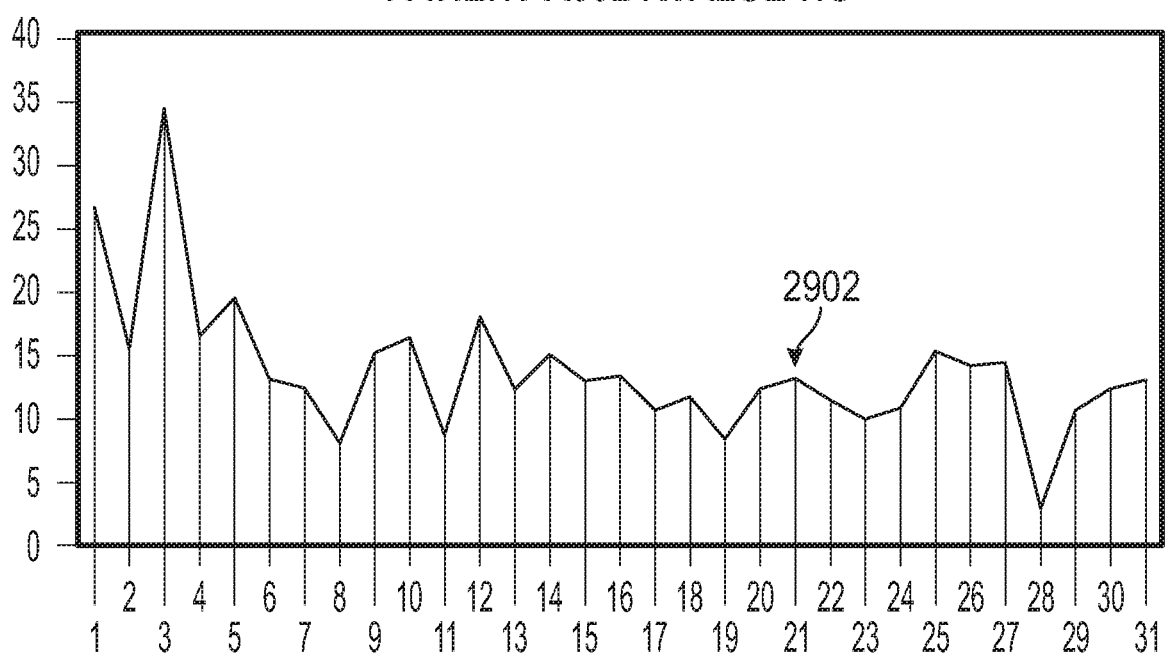
FIG. 29B illustrates a graphical representations of clinical data obtained from one of a plurality of patients in a second clinical trial.
Figure 29C:
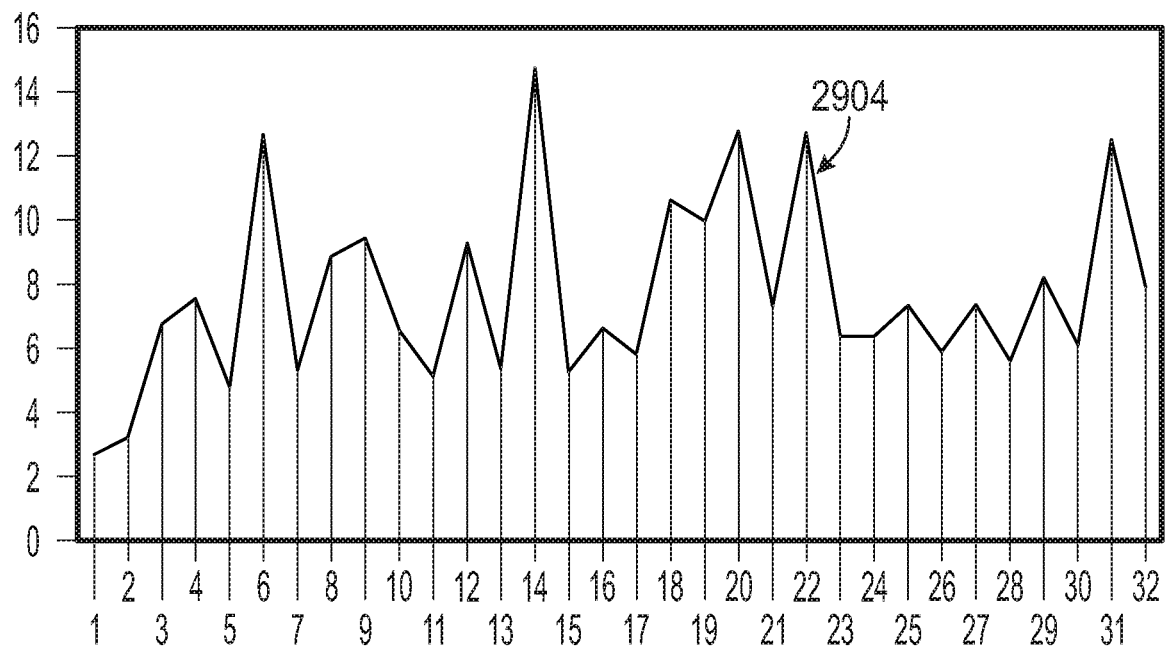
FIG. 29C illustrates a graphical representations of clinical data obtained from one of a plurality of patients in a second clinical trial.
Figure 29D:
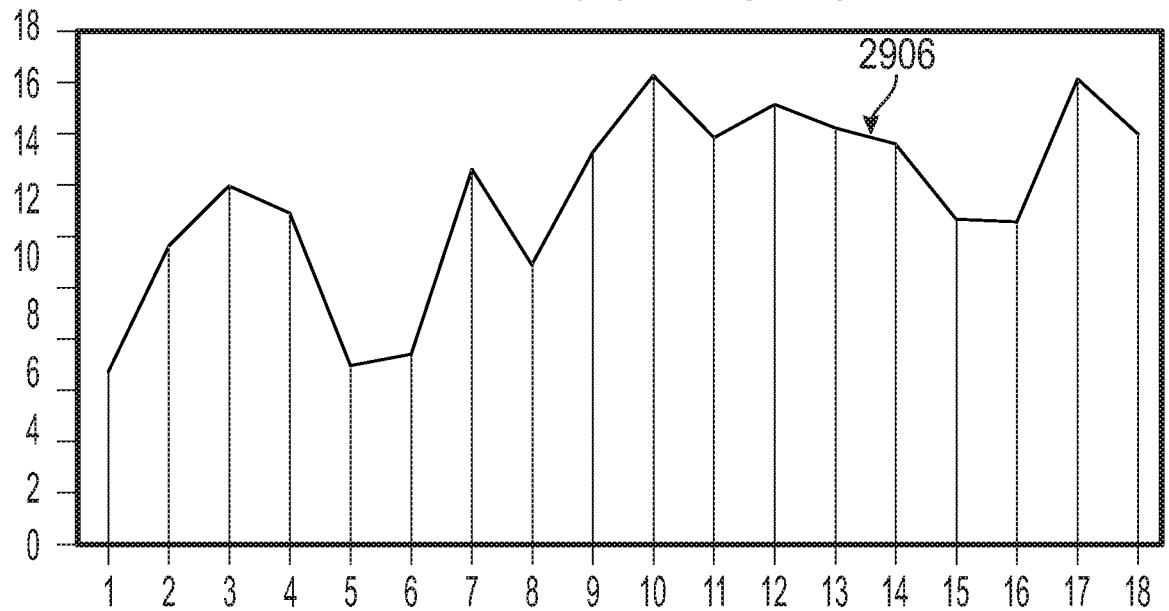
FIG. 29D illustrates a graphical representations of clinical data obtained from one of a plurality of patients in a second clinical trial.
Figure 29E:
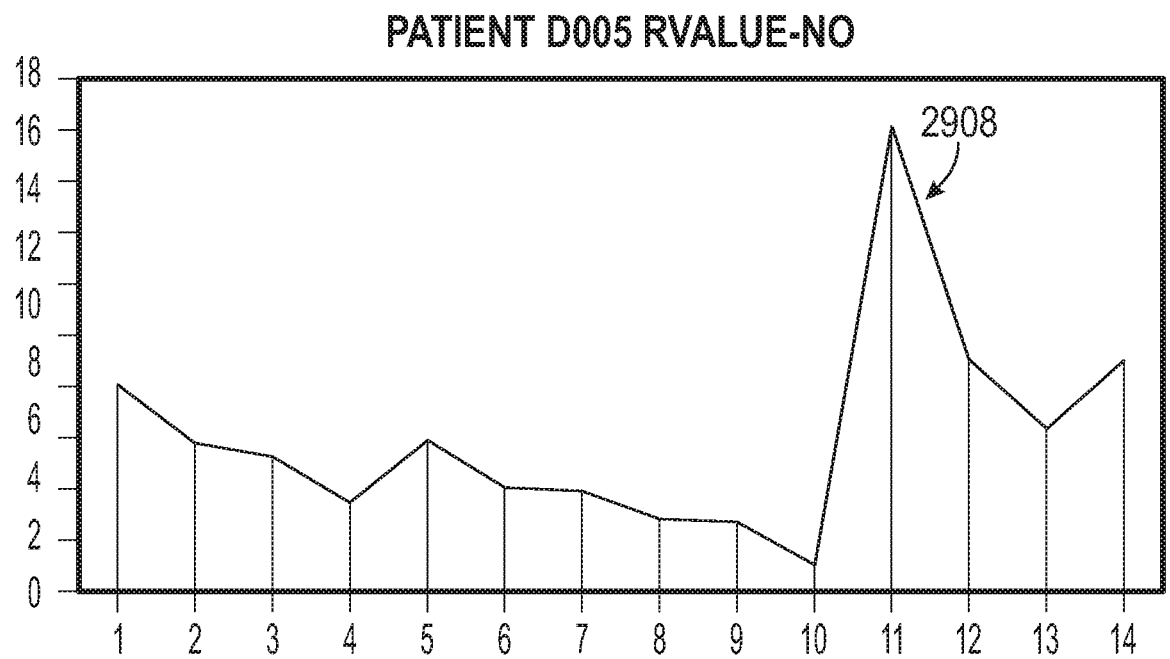
FIG. 29E illustrates a graphical representations of clinical data obtained from one of a plurality of patients in a second clinical trial.
Figure 29F:
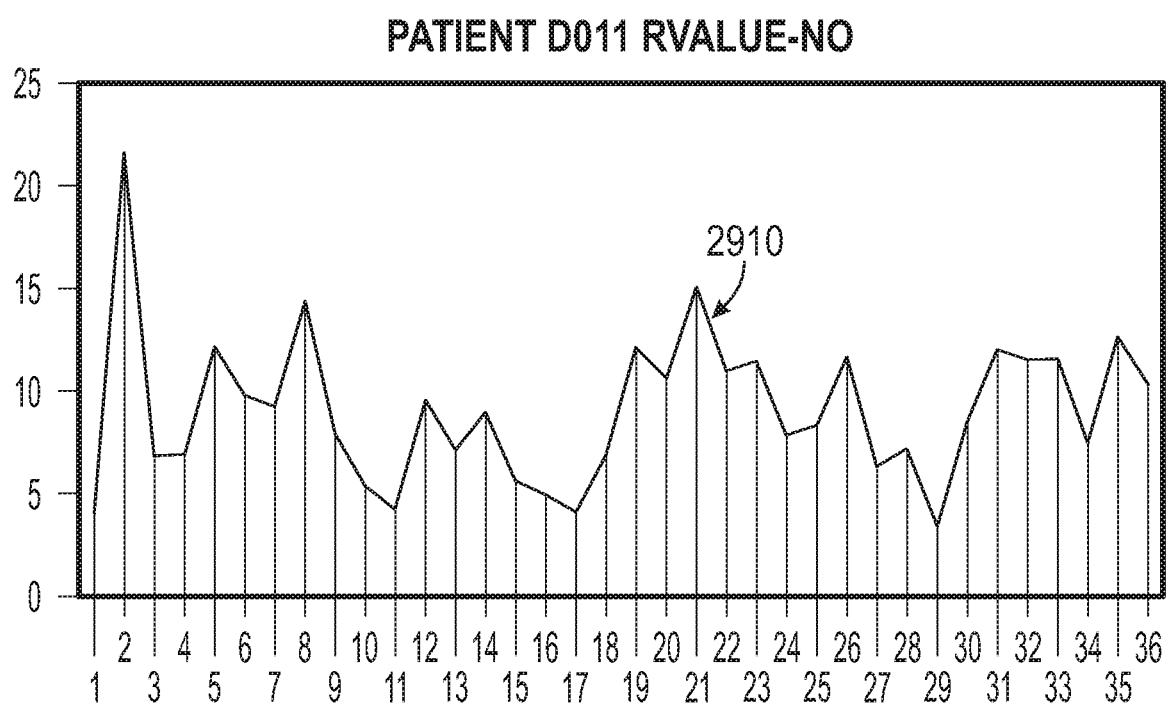
FIG. 29F illustrates a graphical representations of clinical data obtained from one of a plurality of patients in a second clinical trial.

In FIG. 29A, the patient D010 was tested at two hour intervals over a three day period to obtain 34 sample windows. The $R_{395/940}$ values 2900 range from an approximate low of 2 to an approximate high of 14. In FIG. 29B, the patient A002 was tested at two hour intervals for a total of 31 sample windows. The $R_{395/940}$ values 2902 range from an approximate low of 2 to an approximate high of 35. In FIG. 29C, the patient A009 was tested at two hour intervals to obtain 32 sample windows. The $R_{395/940}$ values 2904 range from an approximate low of 2.5 to an approximate high of 15. In FIG. 29D, the patient A010 was tested at two hour intervals to obtain 18 sample windows. The $R_{395/940}$ values 2906 range from an approximate low of 6 to an approximate high of 17. In FIG. 29E, the patient D005 was tested at two hour intervals to obtain 14 sample windows. The $R_{395/940}$ values 2908 range from an approximate low of 1 to an approximate high of 17. In FIG. 29F, the patient D011 was tested at two hour intervals to obtain 36 sample windows. The $R_{395/940}$ values 2910 range from an approximate low of 4 to an approximate high of 22.

Various factors affect the NO levels among the patients. For example, it seems from the R values that patient D010 released less NO in the bloodstream than patient A002. Patient D010 also had issues with kidney function and presented with vascular disease due to diabetes. These underlying illnesses seemed to lessen the NO released in the blood stream and the resulting R values. Thus, the endothelial health of a patient may affect the R values and diagnosis. In an embodiment, the biosensor 100 may adjust its determination of thresholds or other parameters in response to an underlying health condition of a patient, such as diabetes or atherosclerosis.

Figure 30:
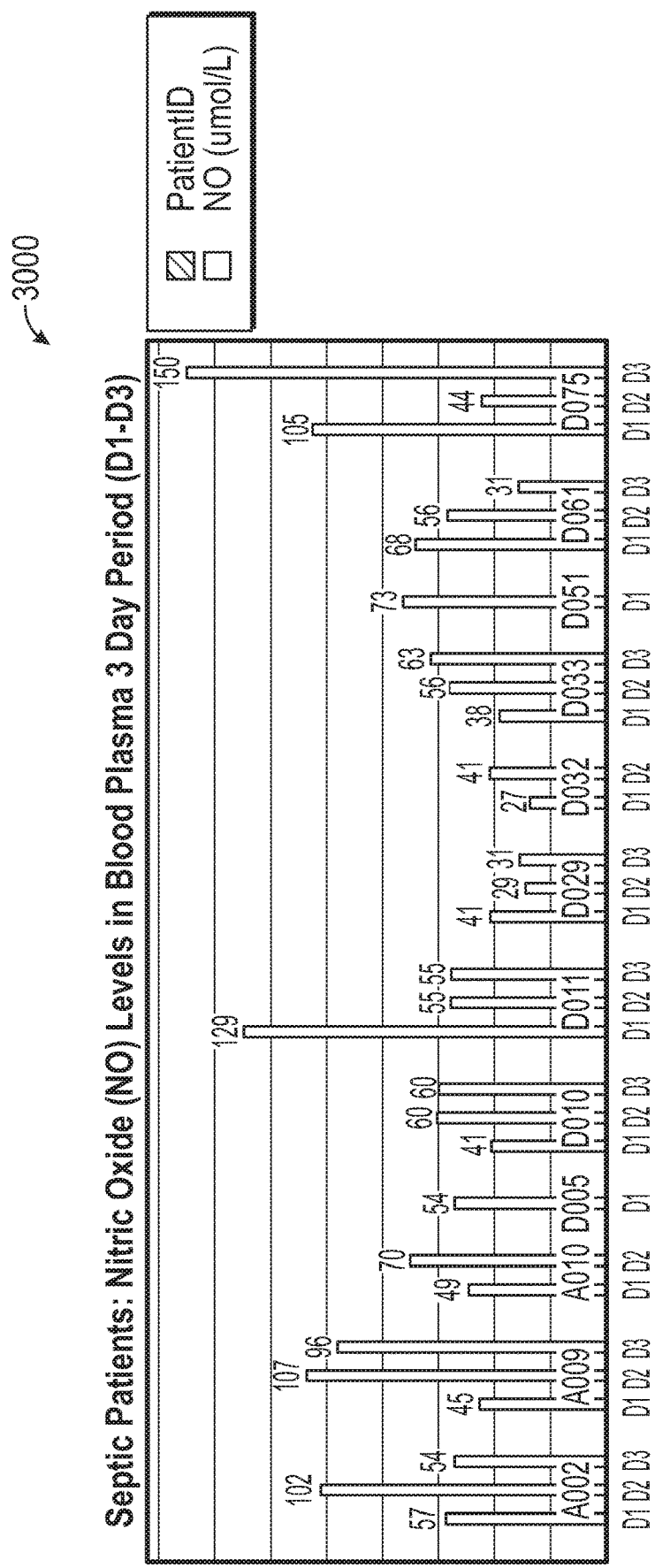
FIG. 30 illustrates a graphical representation of clinical data obtained from blood samples of the patients diagnosed with sepsis during the second clinical trial.

FIG. 30 illustrates a graphical representation 3000 of clinical data obtained from blood samples of the patients diagnosed with sepsis during the second clinical trial. The patients shown in FIG. 30 were diagnosed with sepsis using conventional laboratory tests such as, CBC complement, serum lactate levels or other types of tests. These patients were also identified under qSOFA by the presence of 2 or more clinical criteria: altered mentation, respiratory rate ≥22 breaths/min, and systolic blood pressure ≤100 mm Hg. The NO level was tested in the patients by obtaining a blood sample and analyzing NO levels in blood plasma in vitro. The NO level is illustrated in the graphical representation 300 in units of umol/L. This testing of NO levels was performed once per day over one or more days, D1, D2, D3, for each of the patients identified as A009, A010, D005, D010, D011, D029, D032, D033, D051, D061 and D075.

In contrast, the biosensor 100 was able to obtain a measurement of NO levels in just 5 minutes at two hour intervals. Thus comparing patient A0002, using conventional methods, an NO level was obtained daily, e.g. three times using blood serum data over the three day period. In contrast, the biosensor 100 was able to obtain a measurement of NO levels 28 times over the same three day period at two hour intervals.

The testing shows abnormally high levels of NO in blood plasma due to the infection. The biosensor 100 was able to detect these high levels of NO in the patients at least 2-8 hours before Sepsis-3 identification under qSOFA methods. Thus, it seems that increased NO levels are a precursor to sepsis and may be used as a factor to screen a patient for infection and sepsis to determine hospitalization, ICU placement, respiratory treatment, antibiotic course of treatment, etc.

Figures 31, 32:
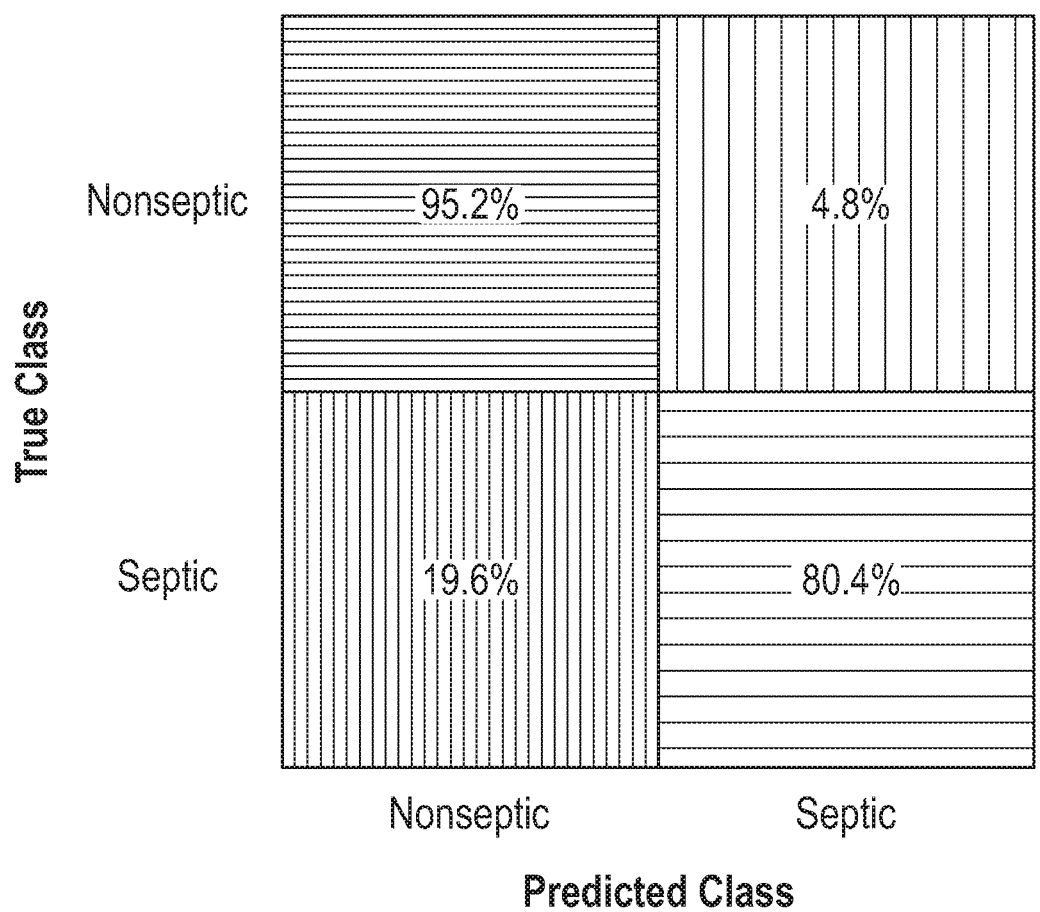
FIG. 31 illustrates a graphical representation of conclusions from data obtained during the second clinical trial.
FIG. 32 illustrates a graphical representation of conclusions from the second clinical trial.

FIG. 31 illustrates a graphical representation of conclusions from data obtained during the second clinical trial. The second clinical trial included n-122 patients with a portion of the patients being diagnosed as septic using conventional laboratory tests, such as CBC complement, serum lactate levels or other tests. Through an analysis of the data, it was determined that healthy patients without sepsis have an average $R_{395/940}$ value in a range from 1-10. In vitro blood serum tests of these patients indicate an approximate NO level of 20 umol/L. Patients with an infection or pre-septic condition have an average $R_{395/940}$ value in a range from 12 to less than 20. In vitro blood serum tests of these patients indicate an approximate NO level of 20 umol/L to less than 90 umol/L. Patients with sepsis or an acute infection requiring hospitalization or treatment in an intensive care unit (ICU) have an average $R_{395/940}$ value greater than 20. In vitro blood serum tests of these patients indicate an approximate NO level of 30 umol/L to less than 180 umol/L. The average $R_{395/940}$ values are thus dependent on the NO levels in blood and provide an indication of a presence of an infection and severity level of the infection (SIRS, sepsis, severe sepsis, septic shock, recovery).

The ranges of $R_{395/940}$ values for healthy, sick and acute infection in FIG. 31 are exemplary and based on limited clinical data of 122 patients. As seen from FIG. 25, in the first clinical trial, a range of the R value was from 0.1 to 8 for a person without a septic condition. The range of the R value for a person with a sepsis condition was from 30 to 200 or above. The ranges of the $R_{395/940}$ values for healthy, sick and acute infection in the second clinical trial shown in FIG. 31 are somewhat more refined than the $R_{395/940}$ values from the first clinical trial shown in FIG. 27. Both of these ranges are based on preliminary clinical data and may vary with additional clinical data. In addition, a position of the biosensor, pre-existing conditions of a patient or other factors may alter the numerical values of the ranges of the R values described herein.

FIG. 32 illustrates a graphical representation of conclusions from the second clinical trial. The second clinical trial included 122 patients with a portion of the patients being diagnosed as septic using conventional laboratory tests, such as CBC complement, serum lactate levels or other tests. The biosensor 100 was able to correctly identify sepsis in 80.4% of the patients with confirmed cases of sepsis. The biosensor 100 was able to identify non-septic patients in 95.2% of the cases.

The biosensor 100 may thus be used as a screening tool to determine a presence of an infection in a presenting patient. The results of the biosensor 100 may be confirmed with conventional laboratory tests or other additional clinical verification. The biosensor 100 may provide a front line screening to determine an activated immune responses and an initial assessment of a severity of illness. The biosensor 100 is a more cost-effective and quick screening tool versus traditional blood sampling and laboratory tests.

In another embodiment, the average R value and/or NO levels detected by the biosensor 100 may be used with traditional factors in determining a qSOFA score. Traditional factors in determining a qSOFA score include mentation of a patient, a fever of more than 100.4° F. (38° C.) or less than 96.8° F. (36° C.), heart rate of more than 90 beats per minute, respiratory rate of more than 20 breaths per minute, arterial carbon dioxide tension (PaCO2) of less than 32 mm Hg., and/or abnormal white blood cell count. In addition to these traditional factors, the measurement of NO levels from the biosensor 100 may also be considered with the qSOFA score for screening patients.

In another embodiment, the average R value and/or NO levels detected by the biosensor 100 may be used with traditional factors in determining a qSOFA score. Traditional factors in determining a qSOFA score include mentation of a patient, a fever of more than 100.4° F. (38° C.) or less than 96.8° F. (36° C.), heart rate of more than 90 beats per minute, respiratory rate of more than 20 breaths per minute, arterial carbon dioxide tension (PaCO2) of less than 32 mm Hg., and/or abnormal white blood cell count. In addition to these traditional factors, the measurement of NO levels from the biosensor 100 may also be considered with the qSOFA score for screening patients.

In another embodiment, the biosensor 100 may monitor a patient with a known or suspected infection for early signs of sepsis or other increased severity in the illness. The biosensor 100 may monitor continuously or at periodic intervals (e.g. for 5 minutes or less every 1-2 hours).

Figure 33:
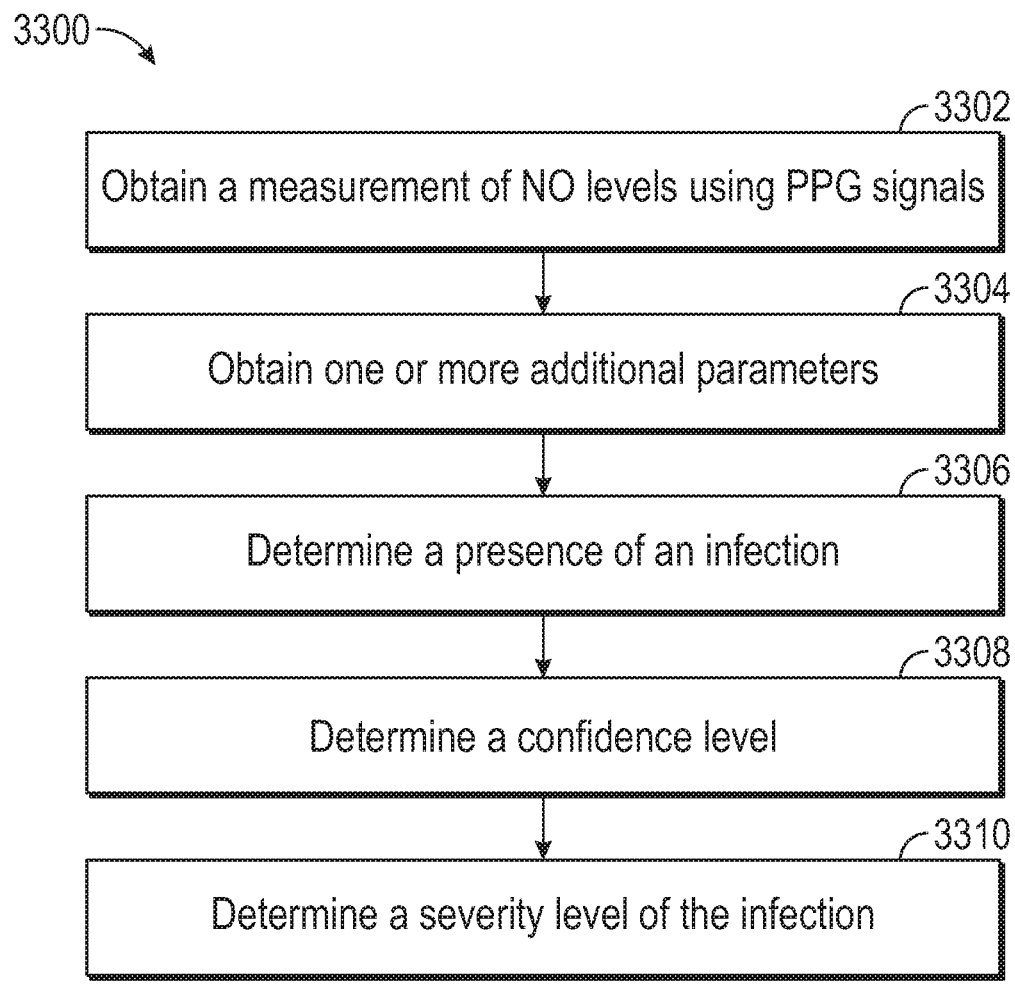
FIG. 33 illustrates a schematic block diagram of an embodiment of a method for screening for an infection by the biosensor.

FIG. 33 illustrates a schematic block diagram of an embodiment of a method 3300 for screening for an infection by the biosensor 100. At 3302, the biosensor 100 obtains a measurement of NO levels using PPG signals, such as $R_{395/940}$. At 3304, the biosensor 100 may obtain one or more additional parameters, such as heart rate, respiration rate, measurement of microcirculation, measurement of bilirubin and creatinine levels, or a blood pressure estimation. The biosensor 100 then determines a presence of an infection using at least the measurement of NO levels. The biosensor may also use one or more of the additional parameters in its determination of a presence of an infection. The infection may be a virus, bacterial infection, fungal infection or parasite. The infection may include sepsis, or other types of underlying infections such as influenza, pneumonia, strep throat, UTI, COVID-10, etc. The biosensor 100 may generate a visual or auditory indication of an infection or no infection. At 3306, the biosensor 100 may indicate a confidence level in its determination. For example, the biosensor 100 may generate a percentage from 0-100%. A 95% confidence interval is a range of values that has 95% certainty it contains the true mean of the population. A confidence level for a data set may be measured in one embodiment by taking half of the size of the confidence interval, multiplying it by the square root of the sample size and then dividing by the sample standard deviation. Other methods may be employed to determine the confidence level for the determination of infection or no infection.

For example, when a patient exhibits a measurement of an NO level greater than 50, then a 95% confidence level may be determined depending on the data set. However, a measurement of an NO level of 11 may generate a 50% confidence level depending on the data set. The confidence level thus provides guidance to a physician on next steps, e.g. further testing or immediate admittance to the hospital/ICU.

The biosensor 100 may also determine a severity level of the infection at 3310 using at least the measurement of the level of NO. The severity level may include one or more classifications, such as mild/moderate, acute, recovery. For example, as shown in FIG. 31, in an embodiment, an R395/940 value of 12 to less than 20 indicates a mild/moderate infection while an R395/940 value of greater than 20 indicates an acute infection, such as sepsis, severe sepsis or septic shock. In another embodiment, the biosensor 100 may generate a range of values to designate the severity level. The SOFA score has a range of 0-24. The biosensor 100 may also determine a range 0-24 to indicate the relative severity level of the infection. The severity level may be based on the measurement of the NO level as well as one or more other parameters, such as respiration rate, temperature, heart rate, estimation of blood pressure, etc.

Figure 34:
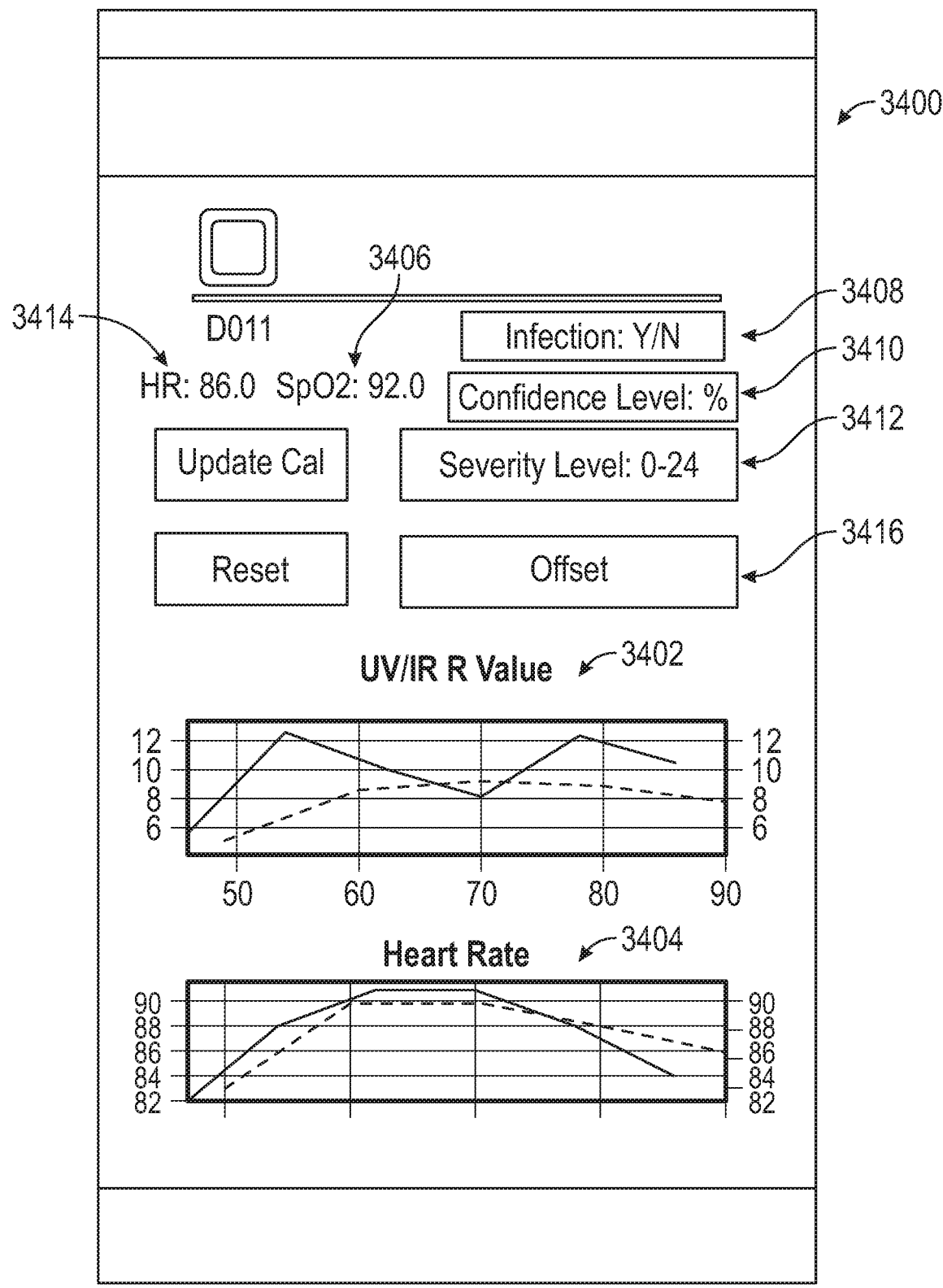
FIG. 34 illustrates a schematic block diagram of an embodiment of an example graphical user interface (GUI) for displaying data obtained from the biosensor.

FIG. 34 illustrates a schematic block diagram of an embodiment of an example graphical user interface (GUI) 3400 for displaying data obtained from the biosensor 100. The GUI 3400 may display a measurement of NO levels determined using $R_{UV/IR}$ values 3402 (such as $R_{395\ nm/940\ nm}$). The display may also illustrate a chart of the heart rate 3404 determined from the PPG signals and a current or moving average heart rate 3414. Oxygen saturation 3406 determined from the PPG signals may also be displayed.

The biosensor 100 may determine and display an indicator of an infection 3408. In an embodiment, the indicator of the infection 3408 is binary, either yes or no. The biosensor 100 may also display a confidence level 3410 of its determination of the infection. The biosensor 100 further may display a severity level 3412, such as a classification (mild/moderate, acute, recovery) or a range (0-10). The confidence level 3410 and severity level 3412 provide additional guidance to a caregiver on next steps for treatment of the patient, e.g. further testing, admitting to the hospital/ICU, immediate antibiotic treatment, etc.

The biosensor 100 may also determine an offset 3416. The offset provides a calibration factor for an individual based on any underlying endothelial dysfunction or other illness, such as diabetes. In operation, the biosensor 100 obtains PPG signals reflected from or transmitted through the tissue of the patient. In less than five minutes, the biosensor 100 is able to determine and provide the indicator of the infection, the confidence level and the severity level.

Figure 35:
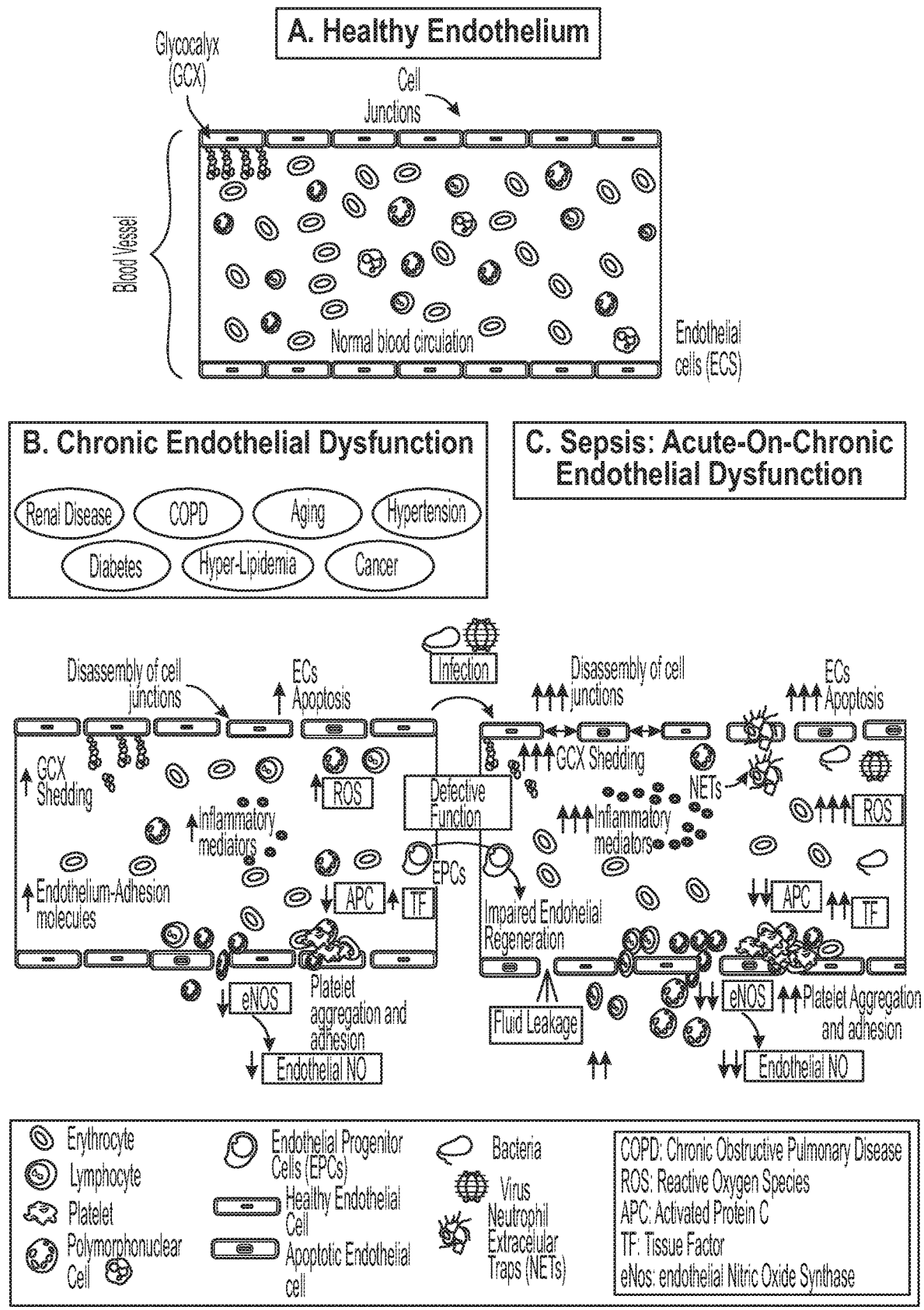
FIG. 35 illustrates a schematic diagram of endothelial dysfunction in a patient with sepsis.

FIG. 35 illustrates a schematic diagram of endothelial dysfunction in a patient with sepsis. The diagram is from the article entitled "Shared Features of Endothelial Dysfunction between Sepsis and Its Preceding Risk Factors (Aging and Chronic Disease)", Bermejo-Martin J F, Martín-Fernandez M, López-Mestanza C, Duque P, Almansa R., J Clin Med. 2018; 7(11):400, Published 2018 Oct. 30, doi:10.3390/jcm7110400, incorporated by reference herein. The diagram illustrates healthy endothelium at A. In A, the endothelial cells are lining a blood vessel with normal blood circulation. The diagram illustrates chronic endothelial dysfunction at B. Endothelial cells are becoming disjointed with disassembly of cell junctions. Endothelial NO (in the form of eNOS) is leaking from the vessels into the tissue creating an increase in NO. The diagram further illustrates acute or chronic endothelial dysfunction as occurs with sepsis at C. In C, the disassembly of cell junctions is further aggravated resulting in fluid leakage from the blood vessels. The level of NO due to leaking of endothelial NO in acute dysfunction may now be double or triple the levels in healthy endothelial of A. The levels of NO in the blood and surrounding tissue may thus provide guidance on the presence of sepsis and the severity of sepsis.

Embodiment—Screening for COVID-19

The severe acute respiratory syndrome coronavirus 2 (SARS-CoV-2) virus causes the disease COVID-19. The SARS-CoV-2 virus is not a living organism, but a protein module (DNA) covered by a protective layer of lipid (fat), which, when absorbed by the cells of the ocular, nasal, or buccal mucosa, changes their genetic code. The SARS-CoV-2 virus mutates cells and coverts them into aggressor and multiplier cells. Current COVID-19 testing includes the COVID-19 RT-PCR test. It is a real-time reverse transcription polymerase chain reaction (RT-PCR) test for the qualitative detection of nucleic acid from SARS-CoV-2 in upper and lower respiratory specimens (such as nasopharyngeal or oropharyngeal swabs, sputum, lower respiratory tract aspirates, bronchoalveolar lavage, and nasopharyngeal wash/ aspirate or nasal aspirate) collected from individuals suspected of SARS-COV-2 viral infection by their healthcare provider. These COVID-19 RT-PCR tests are critically low and even if administered, it takes 1-5 days to obtain a result. Furthermore, screening of patients is problematic because it currently is based on limited information, such as temperature and individuals' self-assessment of their state of health or contact with other persons diagnosed with COVID-19.

In an embodiment, the biosensor 100 and methods thereof may assist in screening patients for SARS-COV-2 to determine a presence of an infection. In initial testing, blood plasma data from thirty patients with COVID-19 was obtained. The blood plasma data includes NO levels over two periods seven days apart with increasing severity of illness. Based on initial testing using the blood plasma data, the blood plasma did contain elevated levels of NO. The biosensor 100 may thus screen patients for COVID-19 using a measurement of NO levels.

The biosensor 100 may detect whether a patient has an infection and provide a confidence factor and even a severity level. As described with respect to FIG. 31, in a second clinical trial, healthy patients without infection had an average $R_{395/940}$ value in a range from 1-10. Patients with an infection or pre-septic condition had an average $R_{395/940}$ value in a range from 12 to less than 20. Patients with sepsis or an acute infection requiring hospitalization or treatment in an intensive care unit (ICU) had an average $R_{395/940}$ value greater than 20. Additional clinical data and verification may be obtained to derive the R values, e.g. measurements of NO levels, present in COVID-19 patients at various stages of the illness.

A physician may use the screening information from the biosensor 100 to determine treatment and further testing for a patient. For example, when the patient has no elevated levels of NO, e.g. an R value of 1-10, the patient may be advised that no further testing is required. In another example, when the patient has a measurement value of NO around 15, the physician may request further testing including COVID-19 RT-PCR testing since the immune expression may be correlated with the presence of the SARS-COV-2 virus. In another example, when the patient has a measurement value of NO around 30, the physician may advise immediate hospitalization and testing.

A person may have COVID-19 and be asymptomatic (no cough or fever), but once a person is exposed the coronavirus, the body starts producing an immune response to fight the infection. The biosensor 100 may thus provide a more accurate screening of persons needing to be tested for COVID-19. Additionally, when a person is not asymptomatic, the measurement of the NO levels by the biosensor 100 may be used along with one or more of the symptoms, such as cough, fever, contact with other COVID-19 patients, in determining screening and testing.

The biosensor 100 may thus screen for infections, such SARS-COV-2. The biosensor 100 may differentiate between patients that need further testing, such as a conventional COVID -19 RT-PCR test and/or a flu test, and healthy patients with no infection that need no further screening. Moreover, sepsis is strongly linked to poor outcomes and mortality in patients with COVID-19. The biosensor 100 may provide monitoring of COVID-19 patients and provide early indications of sepsis in COVID-19 patients.

Figure 36:
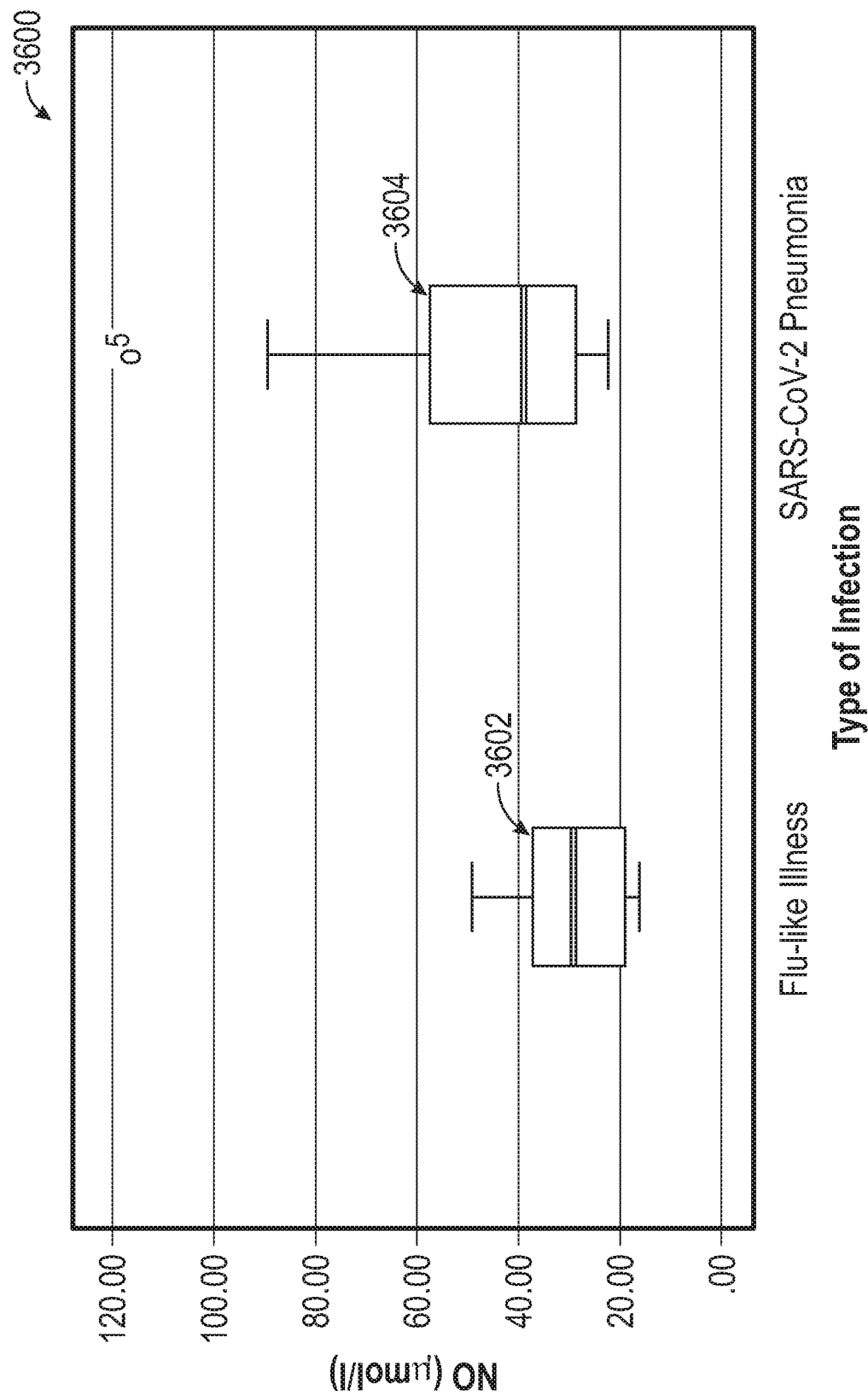
FIG. 36 illustrates a graphical representation of NO levels in patients with a flu-like illness and in COVID-19 patients at a first time period.

FIG. 36 illustrates a graphical representation 3600 of NO levels in patients with a flu-like illness and in COVID-19 patients at a first time period. Blood data of at least 30 patients with a flu-like illness and blood data of at least 30 patients with the SARS-COV-2 virus and pneumonia were analyzed for NO levels. The patients diagnosed with COVID-19 had elevated Nitric Oxide (NO) levels 3604 in blood plasma >=40 umol/L while patients with Flu-Like illness had NO levels 3602 in blood plasma of approximately 30 umol/L. Healthy patients in general have NO levels of approximately 20 umol/L. These findings were provided by European PI on Mar. 17, 2020 via blood serum sampling of 30 COVID-19 patients vs 30 Flu-Like patients at a first time period and then at a second time period seven days later.

As seen in FIG. 36, the range of NO levels is distinct between healthy patients, patients with a flu-like illness and patients with COVID-19. Thus, with further data and verification, the biosensor 100 may thus use a measurement of the NO level of a patient to screen a patient as healthy or with COVID-19. In addition, to the NO levels, the biosensor 100 may use other parameters for this screening.

Figure 37:
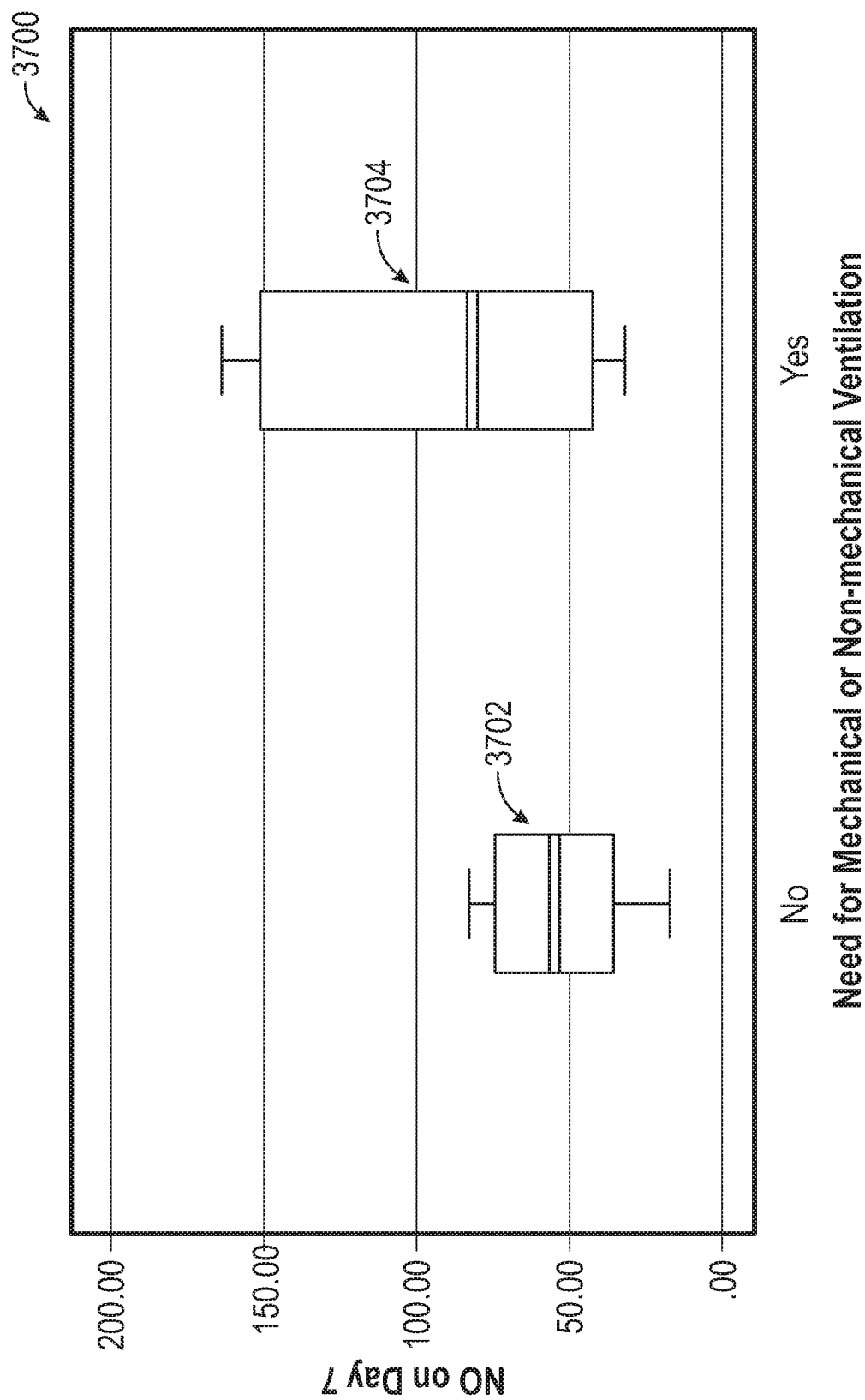
FIG. 37 illustrates a graphical representation of NO levels in patients with a flu-like illness and in COVID-19 patients at a second subsequent time period.

FIG. 37 illustrates a graphical representation 3700 of NO levels in patients with a flu-like illness and in COVID-19 patients at a second subsequent time period. At the second time period seven days later, the patients diagnosed with COVID-19 had greatly elevated Nitric Oxide (NO) levels 3704 in blood plasma >=70 umol/L while patients with Flu-Like illness had NO levels 3702 in blood plasma of approximately 50 umol/L. Healthy patients in general have NO levels of approximately 20 umol/L. These findings were provided by European PI on Mar. 17, 2020 via blood serum sampling of 30 COVID-19 patients vs 30 Flu-Like patients at a first time period and then at a second time period seven days later.

The patients with COVID-19 exhibited increasing NO levels with increased severity of illness after 7 days. The biosensor 100 may monitor the NO levels of patients with COVID-19 to track and predict the severity of the illness over time. The biosensor 100 may thus indicate a severity of COVID-19 in patients with a short, non-invasive test of 5 minutes or less that may easily be administered periodically (e.g., every 1-2 hours) or continuously. These measurements of NO levels may be used to determine a need for hospitalization, ICU, mechanical or non-mechanical ventilation of a patient or early warning of an onset of sepsis.

FIG. 38 illustrates a graphical representation of embodiments of methods of the biosensor 100 for screening and monitoring COVID-19 patients. In a first use case 3802, the biosensor 100 may provide screening for COVID-19 in patients, including public and health care workers. Current state 3804 of screening methods includes determining whether a person has symptoms consistent with COVID-19. To verify, the COVID-19 RT-PCR test is administered including a nasopharyngeal swab and oropharyngeal swab, nasopharyngeal aspirate, endotracheal aspirate, BAL or sputum tests. The time to test results may be 1-5 days depending on the lab service capacity, work-load and prioritization. In a method 3806 with the biosensor 100, the biosensor 100 screens patients for COVID-19. In five minutes or less, the biosensor 100 may detect a measurement of NO levels to screen for COVID-19. The biosensor 100 may detect other parameters and use these parameters as well to screen for COVID-19, such as heart rate, respiration rate, temperature, etc.

In another use case 3802, the biosensor 100 may monitor patients either at home or in a hospital or other care facility.

Conventional methods of monitoring patients with COVID-19 include a clinical assessment of severity of expression of the immune system response to the SARS-CoV-2 virus to determine medication, hospitalization, ICU, oxygen therapy or ventilation. The clinical assessment is dependent on clinical progression of symptoms of COVID-19 in patients over time after first presentation. In an embodiment, the biosensor 100 monitors a patient and assists a clinician in determining a severity level, such as healthy, severe, critical. For example, the biosensor 100 determines a measurement of NO level which is used to determine the severity of the immune response and need for medication, hospitalization, ICU, oxygen therapy or ventilation.

In another use case 3802, the biosensor 100 may monitor patients at high risk such as in nursing homes or homes for the disabled. Current methods include monitoring a patient for severe infection or sepsis according to qSOFA guidelines. However, the qSOFA guidelines may not be met until 2-8 hours after onset of sepsis. In an embodiment, the biosensor 100 may monitor patients for severe infection/sepsis using current hospital protocols and the measurements of NO levels from the biosensor 100. The biosensor 100 may determine elevated NO levels indicating early onset of sepsis up to 2-8 hours before standard clinical methods (such as qSOFA guidelines).

The biosensor 100 may track other indicators of COVID-19, such as heart rate, respiration rate, oxygen saturation and temperature. By tracking NO levels, respiratory rate, heart rate, oxygen saturation and temperature, the biosensor 100 may build a model for early COVID-19 detection.

In another use case, the biosensor 100 may determine when a patient has recovered from COVID-19 and may return to work or exit quarantine. Currently, a person must test negative twice at least 24 hours apart to be considered "recovered" and allowed to return to work. However, due to the shortage of tests and length of time to obtain results, this method may prevent healthy persons from returning to essential jobs. The biosensor 100 may detect the measurement of NO levels and other parameters to determine whether a person still has an immune response to the SARS-CoV-2 virus. For example, if the patient has no temperature and no elevated NO levels (e.g., $R_{395/940}$ value is 10 or less) over a 24 hour period, the person may be deemed "recovered" and allowed to return to work.

Embodiment—Neural Network Processing of a Plurality of Parameters for Infection Screening and Monitoring One or more types of neural networks (a.k.a., machine learning algorithms) may be implemented herein to diagnose an infection (such as sepsis, influenza, COVID-19, pneumonia, etc.) in a patient and/or determine a severity of the infection in the patient.

For example, neural networks may be used to analyze data derived from PPG signals. Neural network models can be viewed as simple mathematical models defining a function $f$ wherein $f:X \rightarrow Y$ or a distribution over X or both X and Y. Types of neural network engines or APIs currently available include, e.g. TensorFlow™, Keras™, Microsoft® CNTK™, Caffe™, Theano™ and Lasagne™.

Sometimes the various machine learning techniques are intimately associated with a particular learning rule. The function $f$ may be a definition of a class of functions (where members of the class are obtained by varying parameters, connection weights, thresholds, etc.). The neural network learns by adjusting its parameters, weights and thresholds iteratively to yield desired output. The training is performed using defined set of rules also known as the learning algorithm. Machine learning techniques include ridge linear regression, a multilayer perceptron neural network, support vector machines and random forests. For example, a gradient descent training algorithm is used in case of supervised training model. In case, the actual output is different from target output, the difference or error is determined. The gradient descent algorithm changes the weights of the network in such a manner to minimize this error. Other learning algorithms include back propagation, least mean square (LMS) algorithm, etc. A set of examples or a training set is used for learning by the neural network. The training set is used to identify the parameters [e.g., weights] of the network.

Figure 39:
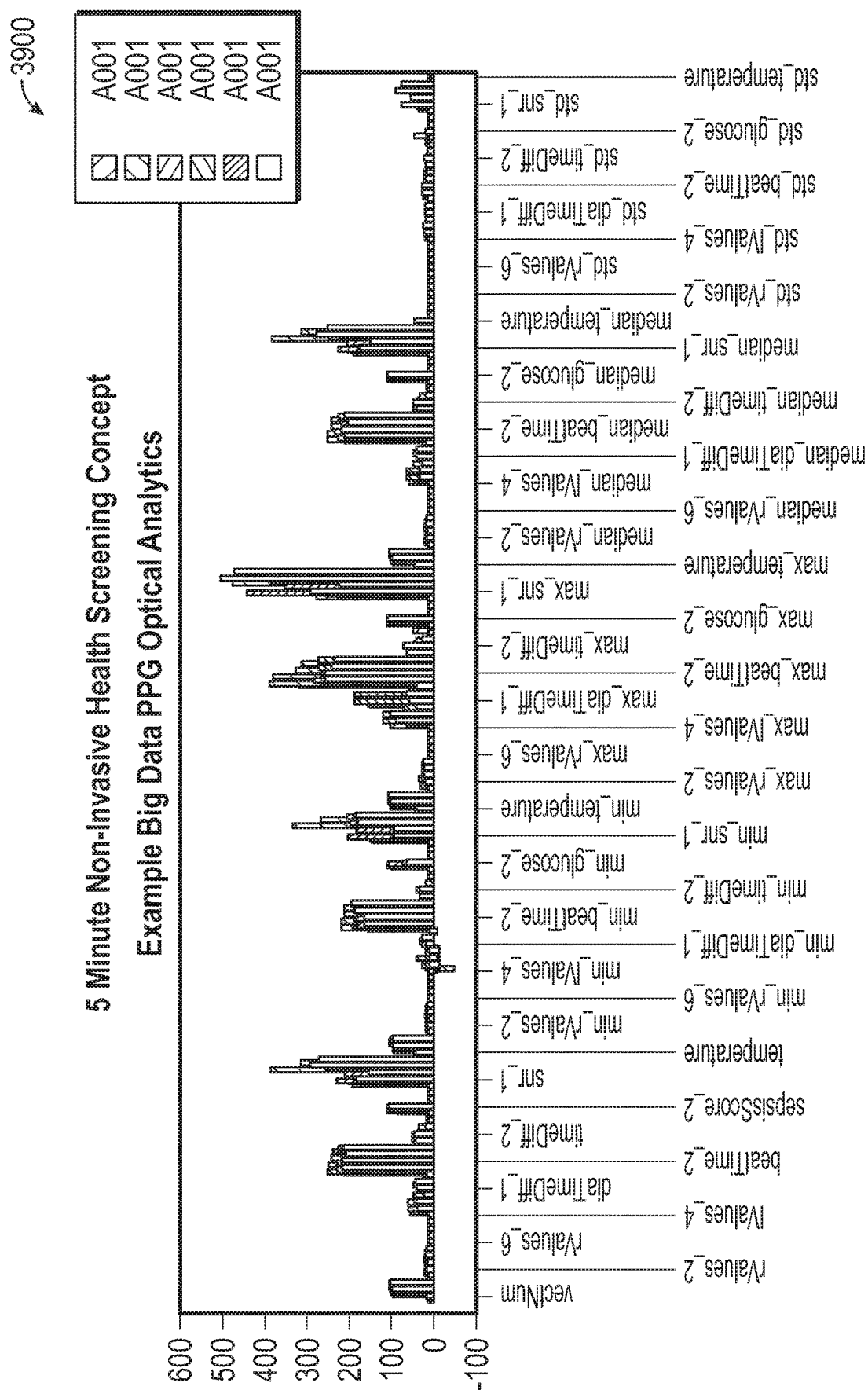
FIG. 39 illustrates a graphical representation of a plurality of parameters that may be analyzed to diagnose a patient with an infection and/or determine a severity level of the infection.

FIG. 39 illustrates a graphical representation of a plurality of parameters 3900 that may be analyzed to diagnose a patient with an infection (such as sepsis, influenza, COVID-19, pneumonia, etc.) and/or determine a severity level of the infection. As previously discussed, an R value obtained using $L\lambda 1=380$ nm-410 nm and $L\lambda 2 \geq 660$ nm may be used as a measurement of a level of NO in blood flow. In an embodiment, the measurement of the level of NO may be used to diagnose a patient with an infection (such as sepsis, influenza, COVID-19, pneumonia, etc.) and determine a severity level of the illness. In addition to the R value obtained using $L\lambda 1=380$ nm-410 nm and $L\lambda 2 \geq 660$ nm, other parameters may be considered in addition to and/or alternatively to this R value in diagnosing an infection (such as sepsis, influenza, COVID-19, pneumonia, etc.) and determining a severity level of the illness. For example, one or more of the following parameters may be used in these determinations:

R value obtained using PPG signals at 395 nm (or in a range of 380 nm-410 nm) and at 940 nm (or equal to or above 660 nm)

R value obtained using PPG signals at 395 nm (or in a range of 380 nm-400 nm) and at 530 nm (or in a range of 510 nm-550 nm)

R value obtained using PPG signals at 530 nm (or in a range of 510 nm-550 nm) and at 940 nm (or equal at or above 660 nm)

R value obtained using PPG signals at 460 nm (or in a range of 440 nm-480 nm) and at 940 nm (or equal at or above 660 nm)

R value obtained using PPG signals at 530 nm (or in a range of 510 nm-550 nm) and at 940 nm (or equal at or above 660 nm)

R value obtained using PPG signals at 468 nm (or in a range of 448 nm-488 nm) and at 940 nm (or equal at or above 660 nm)

L value determined using PPG signals around 395 nm (or in a range of 380 nm-400 nm)

L value determined using PPG signals around 940 nm (or equal at or above 660 nm)

Measurement of a Time or Phase Difference between PPG signals at 395 nm (or in a range of 380 nm-400 nm) and at 940 nm (or equal at or above 660 nm)

Measurement of Correlation of Phase Shape between PPG signals at 395 nm (or in a range of 380 nm-400 nm) and at 940 nm (or equal at or above 660 nm)

Periodicity of a PPG signal at 395 nm (or in a range of 380 nm-400 nm) or at 940 nm (or equal at or above 660 nm)

Skin Temperature

The above parameters are exemplary and additional or alternate parameters may also be considered to diagnose a patient with sepsis or COVID-19 and/or determine a severity level of the illness.

The biosensor 100 may measure creatinine levels using the PPG circuit by detecting PPG signals around 530 nm or in ranges +/−20 nm thereof. Creatinine is produced by the kidneys and various factors can affect the kidney production levels of creatinine. The level of creatinine is also used to determine a SOFA score as shown in Table 1 hereinabove. The biosensor 100 may detect spectral responses, e.g. at 530 nm and 940 nm or in ranges +/−20 nm thereof and obtain an $R_{530/940}$ value. The biosensor 100 may then then provide the measurement of the level of creatinine in blood flow to the neural network.

In another aspect, the biosensor 100 may detect various electrolyte concentration levels or blood analyte levels, such as bilirubin (using L460 nm and L>660 nm or in ranges +/−20 nm thereof to determine an R value) and iron (using L510 nm, L651 nm, L300 nm and L>660 nm or in ranges +/−20 nm thereof to determine an R value) and potassium (using L550 nm or in ranges +/−20 nm thereof and L>660 nm to determine an R value). In particular, the level of bilirubin is a parameter to determine a SOFA score as shown in Table 1 hereinabove. In another aspect, the biosensor 100 may detect sodium chloride NACL (using L450 nm or in ranges +/−20 nm thereof and L>660 nm or in ranges +/−20 nm thereof to determine an R value) concentration levels in the arterial blood flow and determine dehydration level. In another aspect, the biosensor 100 may detect various the levels of the liver enzyme P450 (using L468 nm and L>660 nm or in ranges +/−20 nm thereof to determine an R value).

In an embodiment, the parameters include L values and/or R values obtained using wavelengths having different depths of penetration into the tissue, e.g. 395 nm, 530 nm, 660 nm, 940 nm. The R and L values may thus reflect the level of circulation at various layers of tissue. Poor circulation results in varying R and L values measured using the different wavelengths while good circulation results in less variable R and L values. The differences in good and bad circulation affect the R and L values, and the immune system response.

Other parameters may also include a time delay and/or pulse shape correlation between PPG signals at different depths of tissue, e.g. between PPG signals at 395 nm and 940 nm. For example, the PPG signals at 395 nm and 940 nm may be processed using a cross correlation function or a Hilbert transformation or another algorithm that determines similarities in pulse shape and temporal relationship between the PPG signals. The time delay between the two PPG signals may also be calculated from the phase shift of their wavelet transforms. The Phase Delay and Pulse Shape Correlation provides a measurement of the effects of outer and inner tissue layers of vessels on the PPG signal, e.g. muscle cells during vasoconstriction. The Phase Delay and a Pulse Shape Correlation provide information on a level of vasoconstriction or vasodilation, circulation and arterial stiffness.

When the PPG signals have a greater difference in phase or timing, this indicates that blood flow in the tissue near the surface is decreased, e.g. due to vasoconstriction, due to low blood circulation level or an imbalance of NO and ET-1 or arterial stiffness. When blood flow is increased to the tissue, the PPG signals at the UV and IR wavelengths exhibit a lower variance in pulse shape and a higher correlation value. This decrease in the difference in the pulse shape of the PPG signals at the different wavelengths indicates an increase of blood flow, e.g. due to vasodilation. The vascular flow at the different tissue depths thus provides information on circulation. In addition, when the correlation between pulse shapes decreases, it may indicate circulation issues are occurring.

Another parameter may also include a measurement of periodicity of a PPG signal, e.g. at 395 nm and/or at 940 nm. For example, the periodicity of a PPG signal may include a frequency domain analysis, using a Discrete Fourier Transform (DFT)/determining the periodogram of a signal or using an autocorrelation (cross-product measures similarity across time). Specific measurements or the PPG signal may be determined and input as parameters or compared, e.g. a time between systolic and diastolic points of the PPG signal, e.g. a stroke length, stroke period, amplitude, etc. A signal to noise ratio of a PPG signal may be input. During moments of stress, the PPG signal exhibits decreased periodicity or similarity. Blood volume may change with heart rate as well.

The biosensor 100 may also use the PPG signals to monitor respiration rate and respiration cycles to determine shortness of breath or respiratory effort. Temperature of the patient, such as skin temperature, may be monitored by the biosensor 100 or input. The biosensor 100 may sample temperature periodically, e.g., once a minute, so it may detect slight increases that could signal infection days before symptoms show. The biosensor 100 may also monitor heart rate and oxygen saturation. Blood pressure, oxygen saturation, or temperature may be input as parameters.

The biosensor 100 may also measure the amplitude of the pressure pulse wave as an estimation of blood pressure. In another embodiment, the neural network processing device 4000 may estimate a systolic blood pressure from PPG signals, as described in the article Khalid SG, Zhang J, Chen F, Zheng D. Blood Pressure Estimation Using Photoplethysmography Only: Comparison between Different Machine Learning Approaches. J Healthc Eng. 2018; 2018:1548647. Published 2018 Oct. 23. doi:10.1155/2018/1548647, incorporated by reference herein. The article describes using a single PPG based cuffless blood pressure estimation using three machine learning algorithms (regression tree, multiple linear regression (MLR). The training dataset consisted of three PPG waveform features (pulse area, pulse rising time, and Width_25%) from each of 8133 PPG segments and their corresponding reference systolic and diastolic blood pressure (SBP and DBP). The biosensor 100 may perform similar modeling and training of the neural network using the same or additional or alternative PPG waveform features.

A sepsis SOFA or qSOFA score if available may also be an input parameter to the neural network.

One or more of these parameters may be used to diagnose a patient with an infection, such as sepsis, influenza, pneumonia and/or COVID-19 and/or determine a severity level of the illness. An absolute value, minimum value, maximum value, median value and standard deviation of the values of one or more of these parameters may be input into the neural network.

Figure 40:
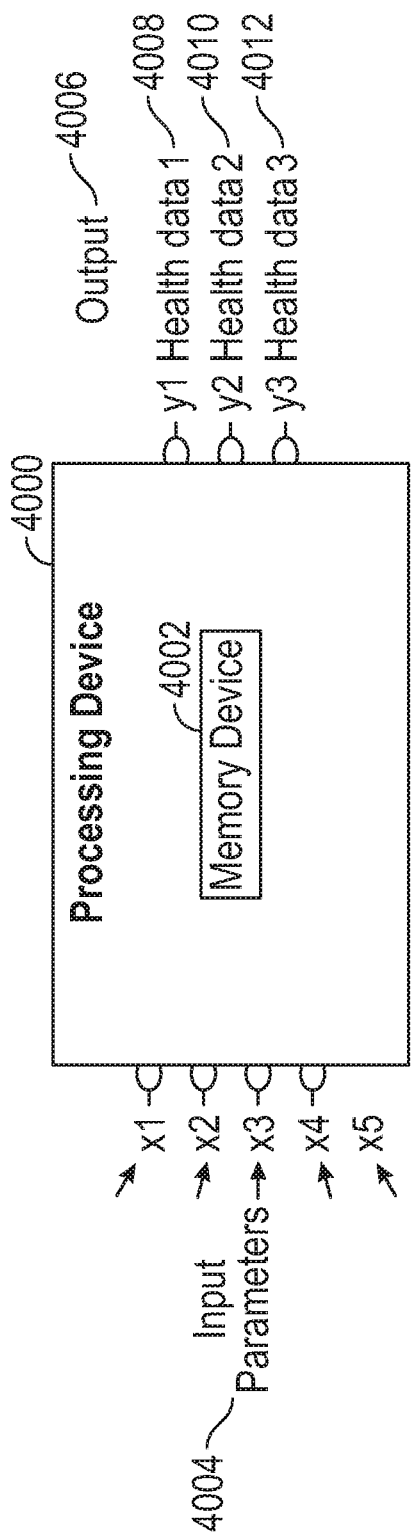
FIG. 40 illustrates a schematic block diagram of an embodiment of a processing device for processing the one or more of the plurality of input parameters.

FIG. 40 illustrates a schematic block diagram of an embodiment of a processing device for processing the one or more of the plurality of input parameters 4004. The processing device 4000 performs one or more of the functions described herein in response to instructions stored in a memory device 4002 and/or other storage devices, either local or remote.

In an embodiment, one or more types of artificial intelligence or neural network processing models may be implemented by the processing device 4000 to determine an output 4006 including health data 4008, 4010, 4012 from one or more of the input parameters 4004. For example, the processing device 4000 may implement a regression model or classifier type model. A regression module neural network may be trained using one or more learning vectors with similar types of input parameters and known outputs as described further hereinabove. A classifier neural network may be applied to the one or more input parameters 4004 to classify a patient as having an infection or no infection.

In another embodiment, a custom algorithm or correlation may be applied to one or more of the input parameters 4004 to determine to determine a severity level of an illness or classify a patient as healthy or having an infection, such as sepsis, COVID-19, influenza, etc. In addition, other types of AI or neural network or machine learning processing, custom algorithms or quantum processing may be applied to determine health data from one or more of these parameters.

Figure 41:
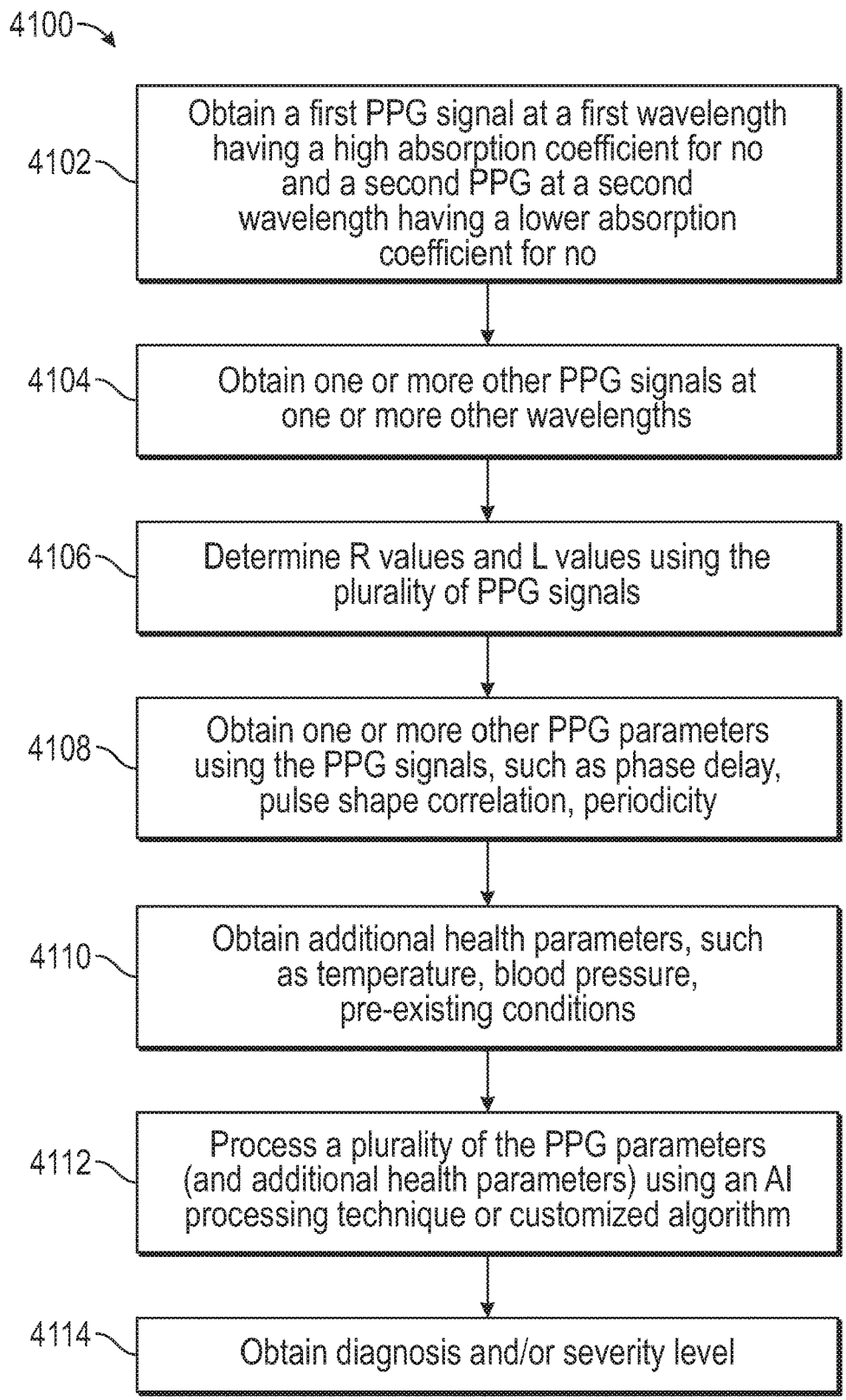
FIG. 41 illustrates a logical flow diagram of an embodiment of a method for using a machine learning or neural network technique for detection of health data

FIG. 41 illustrates a logical flow diagram of an embodiment of a method 4100 for using a machine learning or neural network technique for detection of health data. At 4102, a first PPG signal at a first wavelength (e.g., 380-410 nm) having a high absorption coefficient for NO is obtained and a second PPG at a second wavelength (e.g. greater than 660 nm) having a lower absorption coefficient for NO is obtained. PPG signals at one or more other wavelengths having different depths of penetration into skin tissue are obtained at 4104. The L values and/or R values are obtained at 4106 using the wavelengths having different depths of penetration into the tissue, e.g. 395 nm, 460, 468, 530 nm, 660 nm, 940 nm.

Various parameters of the PPG signals may be determined or measured at 4108. These parameters include the plurality of parameters described hereinabove with respect to FIG. 39, such as heart rate, respiration rate, oxygen saturation, diastolic and systolic points, transfer functions, timing differences between wavelengths, the L values, R values, pulse shape (measured by autoregression coefficients and moving averages), characteristic features of the shape of the PPG waveform, the average distance between pulses, variance, instant energy information, energy variance, etc. Other parameters may be extracted by representing the PPG signal as a stochastic auto-regressive moving average (ARMA). Parameters also may be extracted by modeling the energy of the PPG signal using the Teager-Kaiser operator, calculating the heart rate and cardiac synchrony of the PPG signal, and determining the zero crossings of the PPG signal. The biosensor 100 may also use the PPG signals to determine respiration rate and respiration cycles to measure shortness of breath or respiratory effort. The biosensor 100 may also monitor heart rate, oxygen saturation and estimate blood pressure. These and other parameters may be obtained using one or more PPG signals. The PPG input data may include the PPG signals, and/or one or more parameters derived from the PPG signals.

In an embodiment, additional health parameters or patient data is obtained at 4110. The patient data may include one or more of: age, weight, body mass index, temperature, SOFA or qSOFA score, mean arterial pressure (MAP), pre-existing medical conditions, trauma events, mental conditions, injuries, demographic data, physical examinations, laboratory tests, diagnosis, treatment procedures, medications, radiology examinations, historic pathology, medical history, surgeries, etc. Other factors, such as contact with persons with COVID-19 or in a geographic area with a high density of COVID-19 cases may also be considered.

The plurality of PPG and health parameters of the patient are processed by a processing device executing a neural network (aka machine learning algorithm) at 4112. The processing device executes the machine learning algorithm or neural network techniques to determine health data. The health data includes a diagnosis of whether an infection is present in the patient. The diagnosis may also include a type of infection, such as sepsis, influenza, COVID-19, pneumonia, etc. The health data may also include a confidence factor in the diagnosis. The health data may further include a severity level of the illness. Alarms or warnings may be issued based on the health data. Recommended further screening or tests may be included as well.

The biosensor 100 may classify patients as not having an infection or as having an infection or as needing further testing, such as a conventional PCR test for SARS-COV-2 and/or an influenza test. The biosensor 100 may diagnose a patient as having a certain type of infection, such as sepsis, COVID-19 or other flu-like illness. The biosensor 100 may also indicate a level of severity of the condition, such as mild, acute, critical, recovery, etc. or in a range from 0-10. The biosensor 100 may also determine a confidence level in its diagnosis.

The biosensor 100 may thus indicate a diagnosis of an infection, such as sepsis or COVID-19 and a severity of the infection in patients with a short, non-invasive test of 5 minutes or less that may easily be administered periodically (e.g., every 1-2 hours) or continuously. These measurements may be used to determine a need for hospitalization, ICU, mechanical or non-mechanical ventilation of a patient.

The neural network processing device 4000 needs to be pre-configured with weights, parameters or other learning vectors derived from a training set. The training set preferably includes sets with the same type of information in the input parameters 4004 and known values of the health data 4008, 4010, 4012 in the output 4006. For example, during a learning stage, a neural network adjusts parameters, weights and thresholds iteratively to yield a known output vector from a known input vector. The training is performed using defined set of rules also known as the learning algorithm. For example, a gradient descent training algorithm is used in case of supervised training model. In the case, the actual output is different from target output, the difference or error is determined. The gradient descent algorithm changes the weights of the network in such a manner to minimize this error. Other learning algorithms include back propagation, least mean square (LMS) algorithm, etc. Thus, the training set is used for learning or modeling by the neural network.

In an embodiment, the training set is obtained in a clinical setting. For example, patient data may be obtained during a clinical trial or during use of the biosensor 100. The patient data includes independently verifiable values, such as infection, type of infection (sepsis, COVID-19, pneumonia, influenza, etc.) and severity of illness (SOFA score). Other data may include age, weight, temperature, heart rate, respiration rate, blood pressure, pre-existing conditions, and/or medical history.

Input parameters 4004 and clinically verified output 4006 is obtained for the training set. Preferably, the output 4006 is obtained using a verifiable, independent method. For example, an NO level and COVID-19 status of the patient is obtained using a known method such as a blood test and COVID-19 PCR test respectively. Then PPG signals at one or more wavelengths are obtained, such as at 390 nm, 460 nm, 468 nm, 530 nm, 660 nm and 940 nm or in a range of +/−20 nm from these wavelengths. PPG parameters may be determined from the PPG signals, as described hereinabove.

Temperatures from a temperature sensor on the biosensor 100 may also be used as part of the training set. The input parameters 4004 are then derived from the PPG parameters and patient data. The training set is then generated using the input parameters 4004 and verified output 4006.

The training set is preferably derived from thousands or hundreds of thousands of patients having infections, such as sepsis, COVID-19, influenza and pneumonia. The breadth of data helps the model and training of the neural network processing device 4000.

The training set is processed, e.g. using a learning algorithm for a neural network. The neural network determines a learning vector, e.g. using an estimator function or other learning algorithms. The estimator function system may work blindly, in the sense that no functional restriction is imposed on the relationship between the input and output. In an embodiment, the machine learning algorithm may include one or more of: a "random forest", deep belief network trained using restricted Boltzmann machines, or support vector machine. The analysis may use any known classifier or regression analysis technique, such as, for example and without limitation, random forests, support vector machines, or a deep belief network trained using restricted Boltzmann machines.

The learning vector is thus generated and includes one or more configuration parameters for the neural network processing device 4000. The neural network processing device 4000 is configured with the processing parameters in the learning vector 2106 to process input vectors to obtain output vectors.

In an embodiment, the training set is continually updated, e.g. from clinical settings and user input. The learning vector may be periodically updated (such as hourly, daily, etc.). The updated learning vector may then be obtained and configured on the neural network processing device 4000 periodically as well (such as hourly, daily, etc.).

Embodiment—Hybrid SOFA and qSOFA score

The qSOFA score (also known as quickSOFA) helps identify patients with suspected infections who are at greater risk for a poor outcome outside the intensive care unit (ICU). It uses three criteria, assigning one point for each criteria: low blood pressure (SBP≤100 mmHg), high respiratory rate (≥22 breaths per min), or altered mentation (Glasgow coma scale<15). Organ dysfunction can be identified as an acute change in total qSOFA score ≥2 points consequent to infection. The baseline qSOFA score can be assumed to be zero in patients not known to have preexisting organ dysfunction. The qSOFA score ≥2 reflects an overall mortality risk of approximately 10% in a general hospital population with suspected infection. The qSOFA criteria is used to prompt clinicians to further investigate for organ dysfunction, to initiate or escalate therapy as appropriate, and to consider referral to critical care or increase the frequency of monitoring, if such actions have not already been undertaken.

Figure 42A:
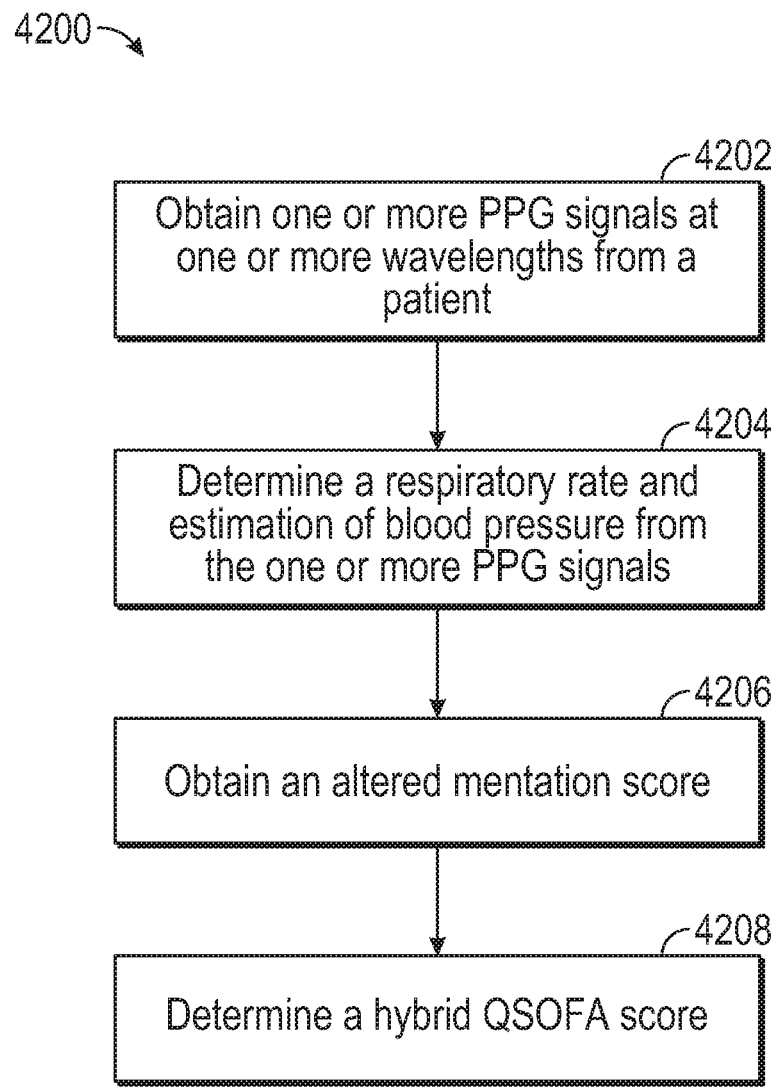
FIG. 42A illustrates a schematic block diagram of an embodiment of a method for generating a hybrid qSOFA score by the biosensor.

FIG. 42A illustrates a schematic block diagram of an embodiment of a method 4200 for generating a hybrid qSOFA score by the biosensor 100. In an embodiment, the biosensor 100 may generate a hybrid qSOFA score. The biosensor 100 obtains one or more PPG signals at one or more wavelengths from a patient at 4202. For example, the biosensor 100 may obtain PPG signals at 395 nm, 660 nm, 940 nm and determine a S/N ratio for the PPG signals to determine one or more signals to use for the hybrid qSOFA score. Using the one or more of the PPG signals, the biosensor 100 may determine a respiratory rate and estimation of blood pressure at 4204. To obtain the estimation of blood pressure, the biosensor 100 may measure an amplitude of the pressure pulse wave and correlate the pressure pulse wave measurement to a range that correlates to hypotension.

In another embodiment, the neural network processing device 4000 may estimate a systolic blood pressure from the one or more PPG signals, as described in the article Khalid SG, Zhang J, Chen F, Zheng D. Blood Pressure Estimation Using Photoplethysmography Only: Comparison between Different Machine Learning Approaches. J Healthc Eng. 2018; 2018:1548647. Published 2018 Oct. 23. doi:10.1155/2018/1548647, incorporated by reference herein. The article describes using a single PPG based cuffless blood pressure estimation using three machine learning algorithms (regression tree, multiple linear regression (MLR). The training dataset consisted of three PPG waveform features (pulse area, pulse rising time, and Width_25%) from each of 8133 PPG segments and their corresponding reference systolic and diastolic blood pressure (SBP and DBP). The biosensor 100 may perform similar modeling and training of the neural network processing device 4000 using the same or additional or alternative PPG waveform features to estimate SBP.

The third criteria of the qSOFA score is an altered mentation (Glasgow coma scale<15). An altered mentation score may need to be input into the biosensor 100 or considered in addition to the hybrid qSOFA score generated by the biosensor 100. For example, organ dysfunction can be identified as an acute change in total SOFA score ≥2 points consequent to infection. The biosensor 100 may determine a qSOFA score ≥2 points using only the respiratory rate and the estimation of blood pressure. The altered mentation criteria may not need to be considered then to escalate treatment of the patient. When the biosensor 100 generates a qSOFA score of 1 point from only the respiratory rate and the estimation of blood pressure, the biosensor 100 may prompt the caregiver to consider mentation independently. In another aspect, the biosensor 100 may prompt an input of a measure of mentation, such as a Glasgow coma scale, as a third factor to determine the overall hybrid qSOFA score.

Figure 42B:
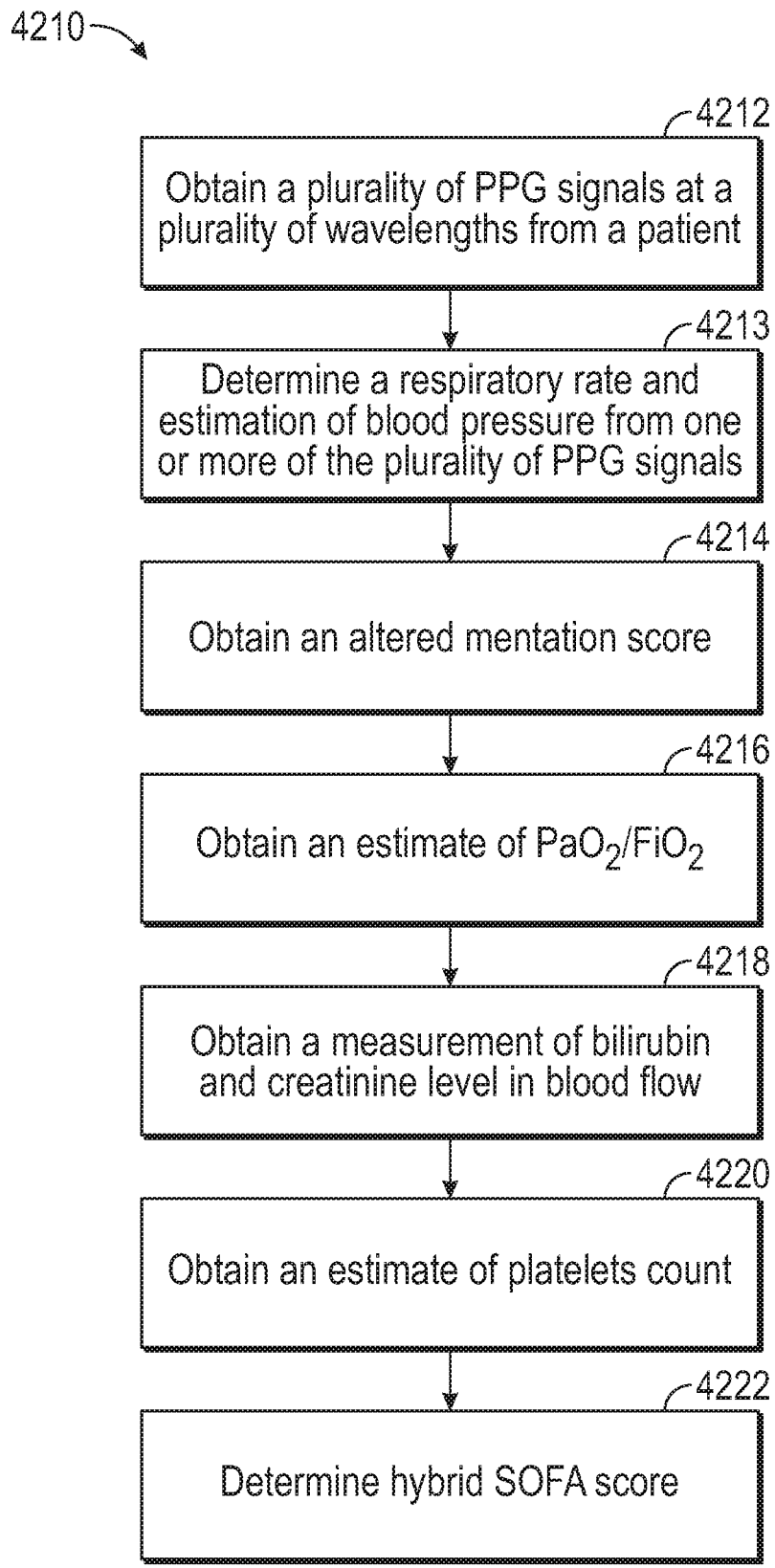
FIG. 42B illustrates a schematic block diagram of an embodiment of a method for generating a hybrid SOFA score by the biosensor.

FIG. 42B illustrates a schematic block diagram of an embodiment of a method 4210 for generating a hybrid SOFA score by the biosensor 100. In an embodiment, the biosensor 100 may generate a hybrid SOFA score. Table 1 hereinabove lists the criteria of a SOFA score 0-4. According to Sepsis-3 definitions, a new increase in SOFA score above baseline (score 0) in the presence of infection makes the diagnosis of sepsis. Increasing SOFA scores are associate with incremental increases in mortality. It is generally advised to calculate the SOFA score using the worst value for each variable in the preceding 24-hour period.

The biosensor 100 obtains a plurality of PPG signals at a plurality of wavelengths from a patient at 4212. As described with respect to FIG. 42A, the biosensor 100 may determine a respiratory rate and estimation of systolic and diastolic blood pressure from one or more of the plurality of PPG signals. The mean arterial pressure (MAP) may be determined from the SBP and DBP. The biosensor 100 may select a worst value or worst average over a sliding window (such as 5-10 minute windows) for each criteria in the preceding 24-hour period.

For the mentation criteria, the biosensor 100 may prompt an input of a measure of mentation, such as a Glasgow coma scale at 4214. In another embodiment, the biosensor 100 does not consider the measure of mentation to generate the hybrid SOFA score. The altered mentation criteria may need to be considered with the hybrid SOFA score by a caregiver to escalate treatment of the patient.

Another criteria in the SOFA score is the ratio $PaO_2/FiO_2$. The partial pressure of oxygen, also known as $PaO_2$, is a measurement of oxygen pressure in arterial blood and is determined by blood tests. It reflects how well oxygen is able to move from the lungs to the blood, and it is often altered by severe illnesses. $FiO_2$ is defined as the percentage or concentration of oxygen that a person inhales (the fraction of inspired oxygen). Natural air includes 21% oxygen, which is equivalent to $FiO_2$ of 0.21. Oxygen-enriched air has a higher $FiO_2$ than 0.21; up to 1.00 which means 100% oxygen. $FiO_2$ is typically maintained below 0.5 even with mechanical ventilation, to avoid oxygen toxicity. This ratio $PaO_2/FiO_2$ may be input into the biosensor 100. Alternatively, the biosensor 100 may use a measurement of oxygen saturation as an estimate of the ratio $PaO_2/FiO_2$ at 4216.

The SOFA criteria also include bilirubin and creatinine levels. A measurement of bilirubin levels in blood flow may be measured by the biosensor 100 at 4218 using L460 nm and L>660 nm or in ranges +/−20 nm to determine an R value. The biosensor 100 may measure creatinine levels using PPG signals around 530 nm or in ranges +/−20 nm thereof to determine an R value.

The SOFA criteria further includes a platelets count that is normally obtained using a blood test. The biosensor 100 may determine an estimate of platelets count using PPG signals at 4220 to detect platelets in blood flow. In another embodiment, the platelet count may be input into the biosensor 100.

Using one or more of these criteria, the biosensor 100 may determine a hybrid SOFA score at 4222. The biosensor 100 may also use one or more other factors described herein to determine the hybrid SOFA score and qSOFA score, such as R values, L values, PPG parameters, etc. One or more of the criteria may be estimated by the biosensor 100 or substituted for other measures of the condition.

Embodiment—Infectious Disease Form Factor

Figure 43A:
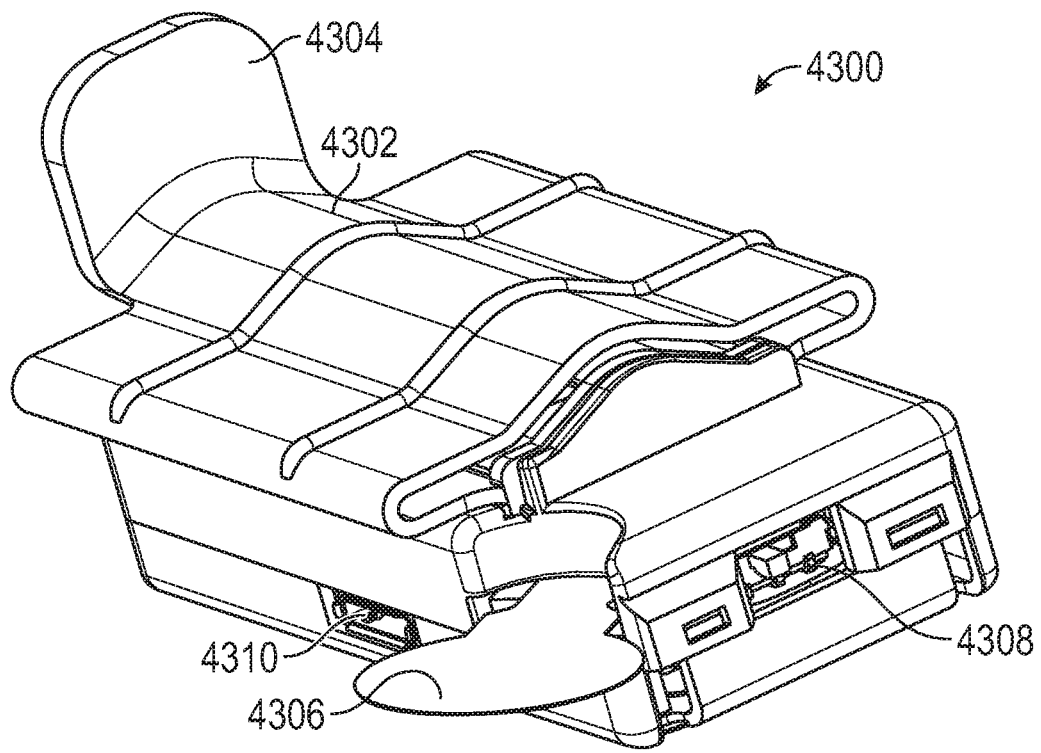
FIG. 43A illustrates a perspective view of a disposable form factor of the biosensor.

FIG. 43A illustrates a perspective view of a disposable form factor 4300 of the biosensor 100. In an embodiment, the biosensor 100 may be implemented in a disposable form factor 4300 with a finger attachment. The biosensor 100 is designed for use with a single patient and may be disposed after use by the single patient. This disposal helps prevent spread of infectious diseases between patients.

The biosensor includes a finger boot 4302 configured to securely hold the biosensor 100 onto a finger. The finger boot 4202 may include rubber or other pliable material that may stretch around and exert a pressure on the finger to hold it securely. A handle 4304 may be used to stretch a top of the finger boot 4302 for insertion of the finger or removal of the finger from the finger boot 4302. A power switch 4308 may be implemented to initiate power and scanning by the biosensor 100. A wired USB port 4310 may be implemented that connects the biosensor 100 to another processing device for viewing and/or analyzing the data collected by the biosensor 100. The biosensor 100 may also include a wireless interface, such as a Bluetooth interface, to transmit data to another processing device. In addition, a removable memory card is connected to a pull tab 4306. The memory card may be easily removed by pulling the tab 4306. The memory card may be sanitized and the data collected by the biosensor 100 retrieved from the memory card.

Figure 43B:
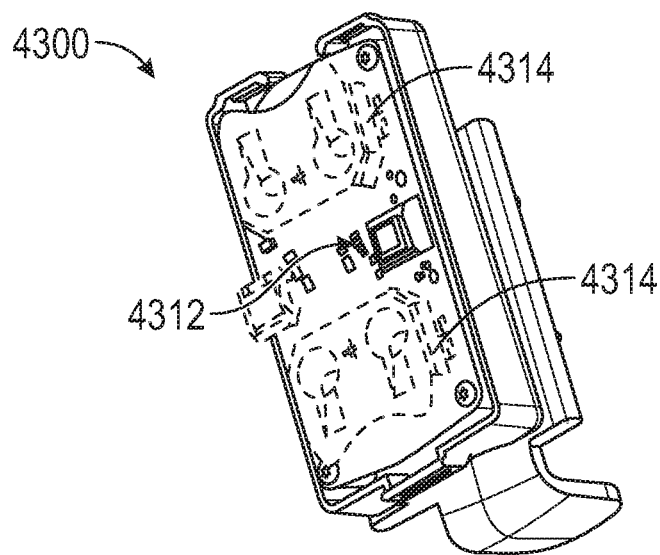
FIG. 43B illustrates a perspective view of internal components of the biosensor.

FIG. 43B illustrates a perspective view of internal components of the biosensor 100 implemented in a disposable form factor with the finger attachment 4300. The biosensor 100 includes one or two batteries 4314, such as coin cells, or other power source. The biosensor 100 also includes a Bluetooth wireless transceiver 4312 and/or other type of wireless transceiver. The biosensor 100 may also include one or more LEDs that indicate a presence of an infection (such as green LED lit for yes or RED LED for no). In another embodiment, the biosensor 100 includes a display, such as shown in FIG. 34.

Figure 44:
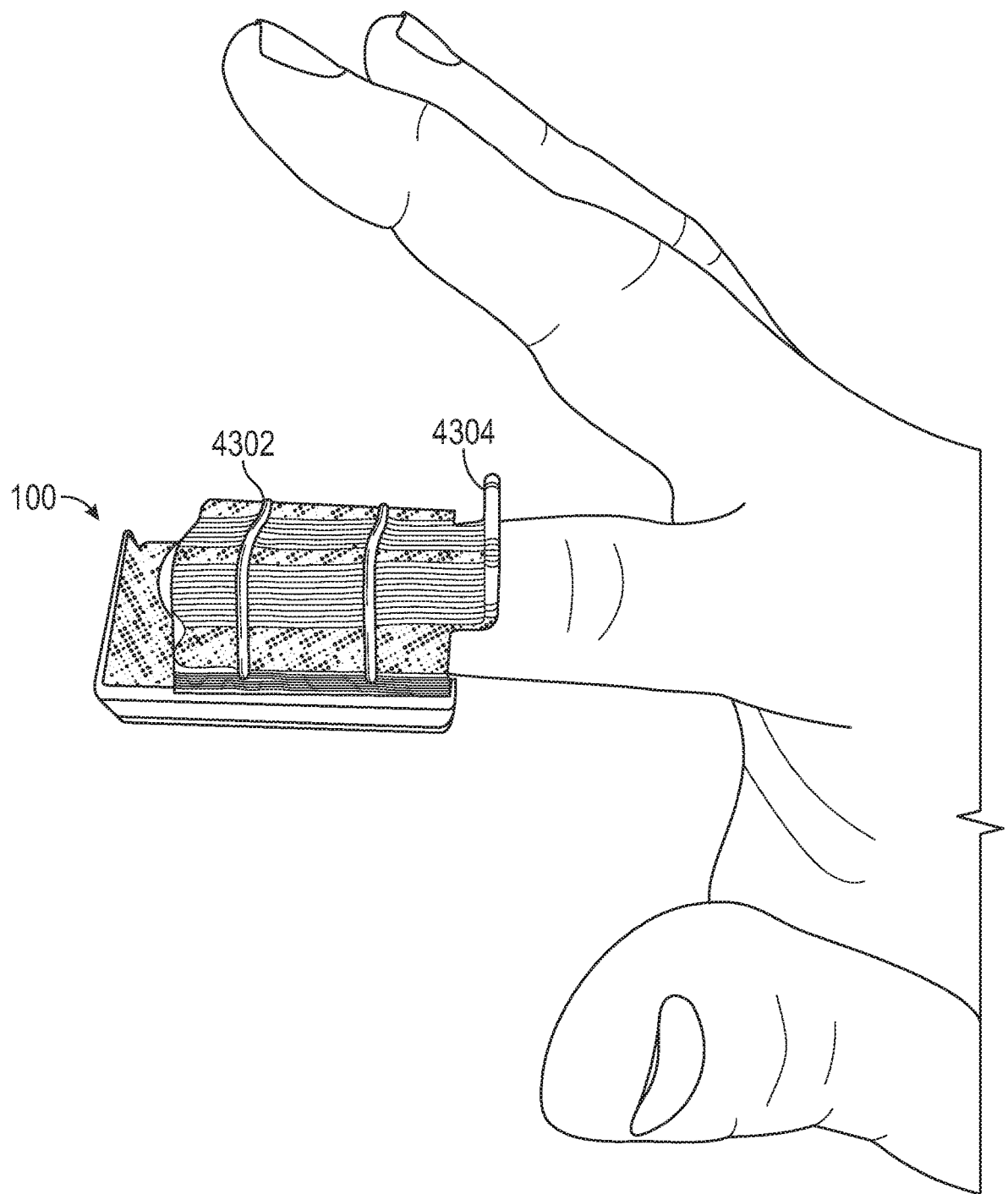
FIG. 44 illustrates a perspective view of the biosensor positioned on a finger of a patient.

FIG. 44 illustrates a perspective view of the biosensor 100 positioned on a finger of a patient. The biosensor 100 includes the finger boot 4302 configured to securely hold the biosensor 100 onto the finger. The finger boot 4302 may include rubber or other pliable material that may stretch around and exert a pressure on the finger to hold it securely. The handle 4304 may be used to stretch a top of the finger boot 4302 for insertion of the finger or removal of the finger from the finger boot 4302.

Figure 45A:
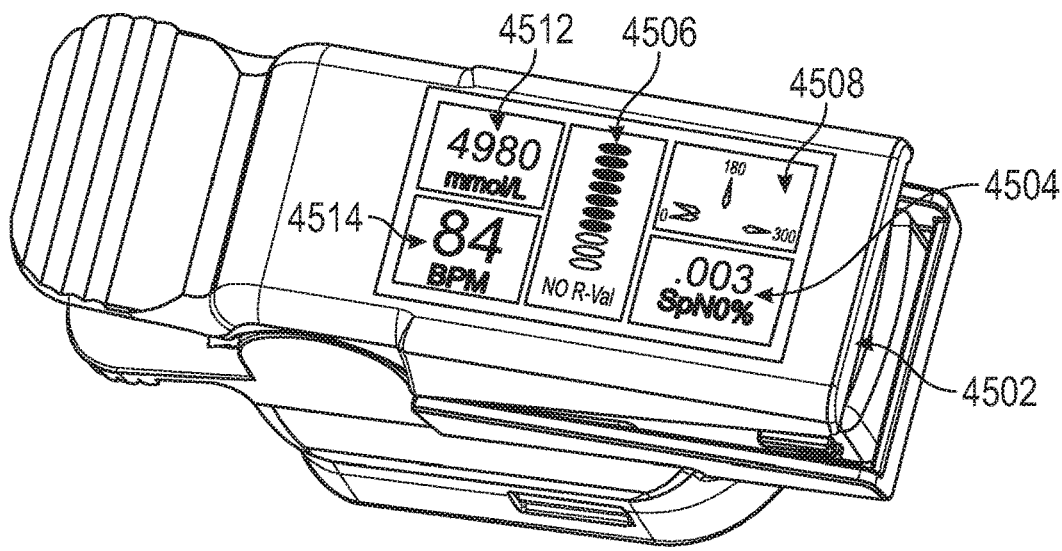
FIG. 45A illustrates a first perspective view of a non-disposable form factor of the biosensor.
Figure 45B:
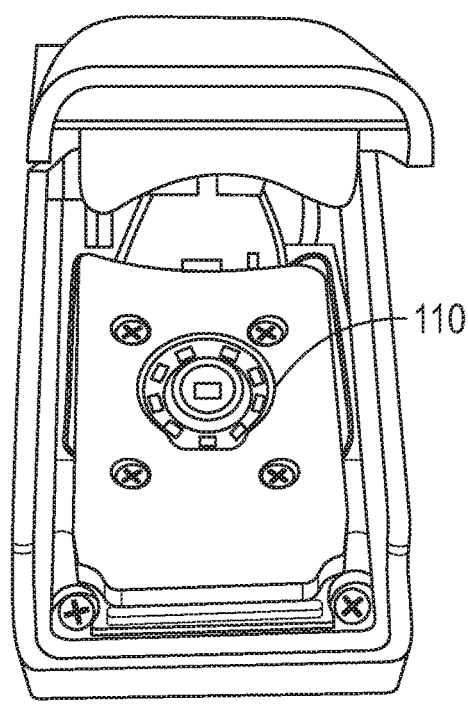
FIG. 45B illustrates a second perspective views of a non-disposable form factor of the biosensor.

FIG. 45A and FIG. 45B illustrate first and second perspective views of a non-disposable form factor of the biosensor 100. In this embodiment, the biosensor 100 includes a finger attachment 4502. The finger attachment 4502 includes the PPG circuit 110 and is configured to securely hold a finger that is inserted into the finger attachment 4502.

In use, a patient places a finger inside the finger attachment 4502. The biosensor 100 is configured to monitor PPG signals of the patient. The biosensor 100 may also monitor temperature using a temperature sensor array in the finger attachment 4502. The biosensor 100 may continuously monitor the patient, e.g. the NO measurements may be obtained a plurality of times per minute and averaged over a predetermined time period, or may be monitored during sample windows (such as five minutes or less) at periodic intervals (such as 1-2 hour periods).

The biosensor 100 may display one or more measurements of the NO levels. The displays may include, e.g., a nitric oxide saturation level 4504 (such as SpNO %). The display may include a bar meter 4506 illustrating a relative measured NO level. The display may include a dial type display 4508 that indicates a relative measured NO level. The biosensor 100 may display the measured NO level in mmol/liter units 4512. These types of displays are examples only and other types of display may be employed to indicate the level of NO measured in a patient. The biosensor 100 may also obtain and display other patient vitals such as heart rate, respiration rate, oxygen saturation and temperature. Though in this embodiment, the display is located on the finger attachment 4502, the biosensor 100 may transmit data to a monitoring station or user device for display of the information. The biosensor 100 may also include a separate device (such as a user device) that processes the PPG signals to obtain the health data described herein.

The biosensor 100 may be implemented in other compact form factors, such as on a patch, wrist band, ring or earpiece. Due to its compact form factor, the biosensor 100 may be configured for measurements on various skin surfaces of a patient, including on a forehead, arm, wrist, abdominal area, chest, leg, ear, ear lobe, finger, toe, ear canal, etc.

Figure 46B:
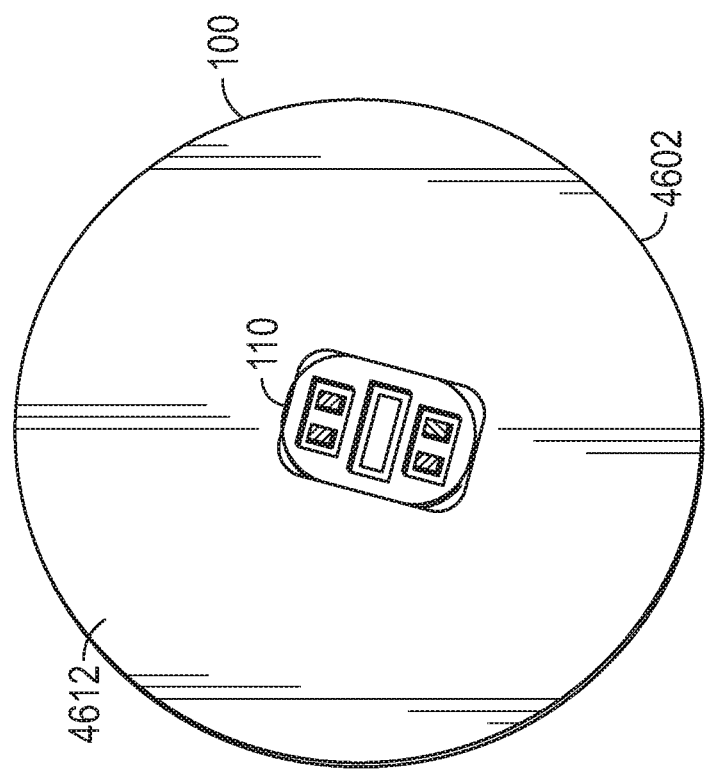
FIG. 46B illustrates a perspective view of a back 4 of the biosensor implemented in a patch form factor.
Figure 46A:
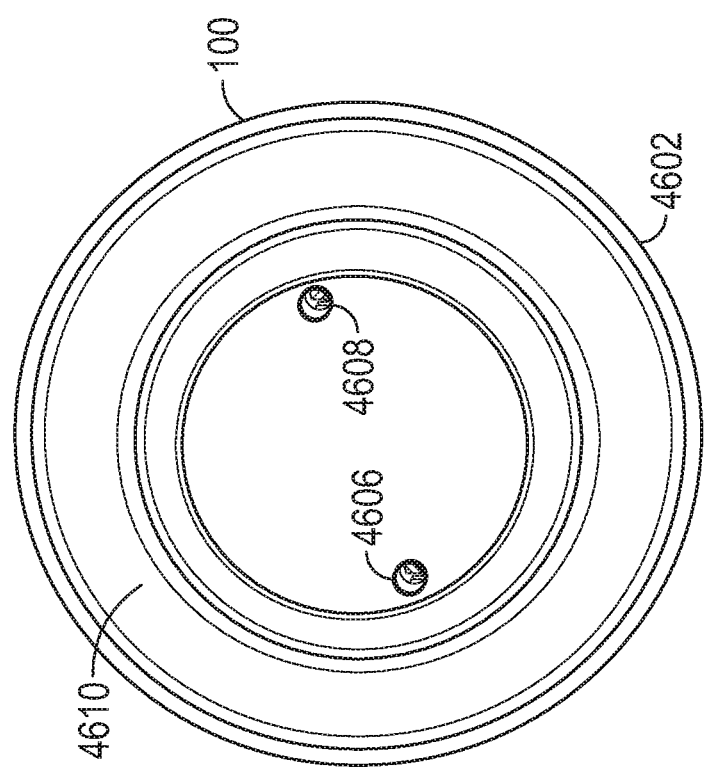
FIG. 46A illustrates a perspective view of a top of a biosensor implemented in a patch form factor.

FIG. 46A and FIG. 46B illustrate perspective views of an embodiment of the biosensor 100 implemented in a patch 4602. FIG. 46A illustrates a perspective view of a top 4610 of the biosensor 100 while FIG. 46B illustrates a perspective view of the back 4612 of the biosensor 100. The biosensor 100 is configured for placement of the back 4612 of the patch 4602 adjacent to skin tissue of the patient. The patch 4602 may include an adhesive backing 104 such that it may adhere to a patient's skin. The patch 4602 may alternatively be secured through other means, such as tape, etc.

The patch 4602 includes the optical sensor photoplethysmography (PPG) circuit 110. The biosensor 100 further includes a health alert indicator to provide an indicator of an infection in the patient. The health alert indicator in this embodiment includes a first LED 4606. When symptoms of an infection are detected, the first LED 4606 may illuminate to provide a warning. For example, the first LED 106 may illuminate a first color (e.g. green) to indicate no or little risk of infection, such as sepsis, COVID-19 or other infection while a second color (e.g. red) may indicate that symptoms have been detected indicating a risk of an infection. The biosensor 100 may also measure other patient vitals such as heart rate, e.g. beats per minute (bpm), respiration rate, oxygen saturation or temperature. These measurements may also be considered when determining an infection, such as sepsis or COVID-19 or other infection. Due to its compact form factor, the patch 4602 may be attached on various skin surfaces of a patient, including on a forehead, arm, wrist, abdominal area, chest, leg, hand, etc.

In an embodiment, the patch 4602 is designed to be disposable, e.g. designed to be used on a single patient. For example, the biosensor 100 may include a battery with a relatively short life span of 24-48 hours. In use, the biosensor 100 is activated and the adhesive backing is peeled and attached to a single patient for monitoring. A second LED 4608 may indicate activation of the biosensor 100. For example, when the second LED 4608 is illuminated, it indicates that the biosensor 100 is activated and monitoring the patient. When the second LED 4608 is not lit, it indicates that monitoring has stopped. When monitoring is complete for that single patient or the battery of the biosensor 100 has lost charge, the patch 4602 is removed and thrown away.

Figure 47:
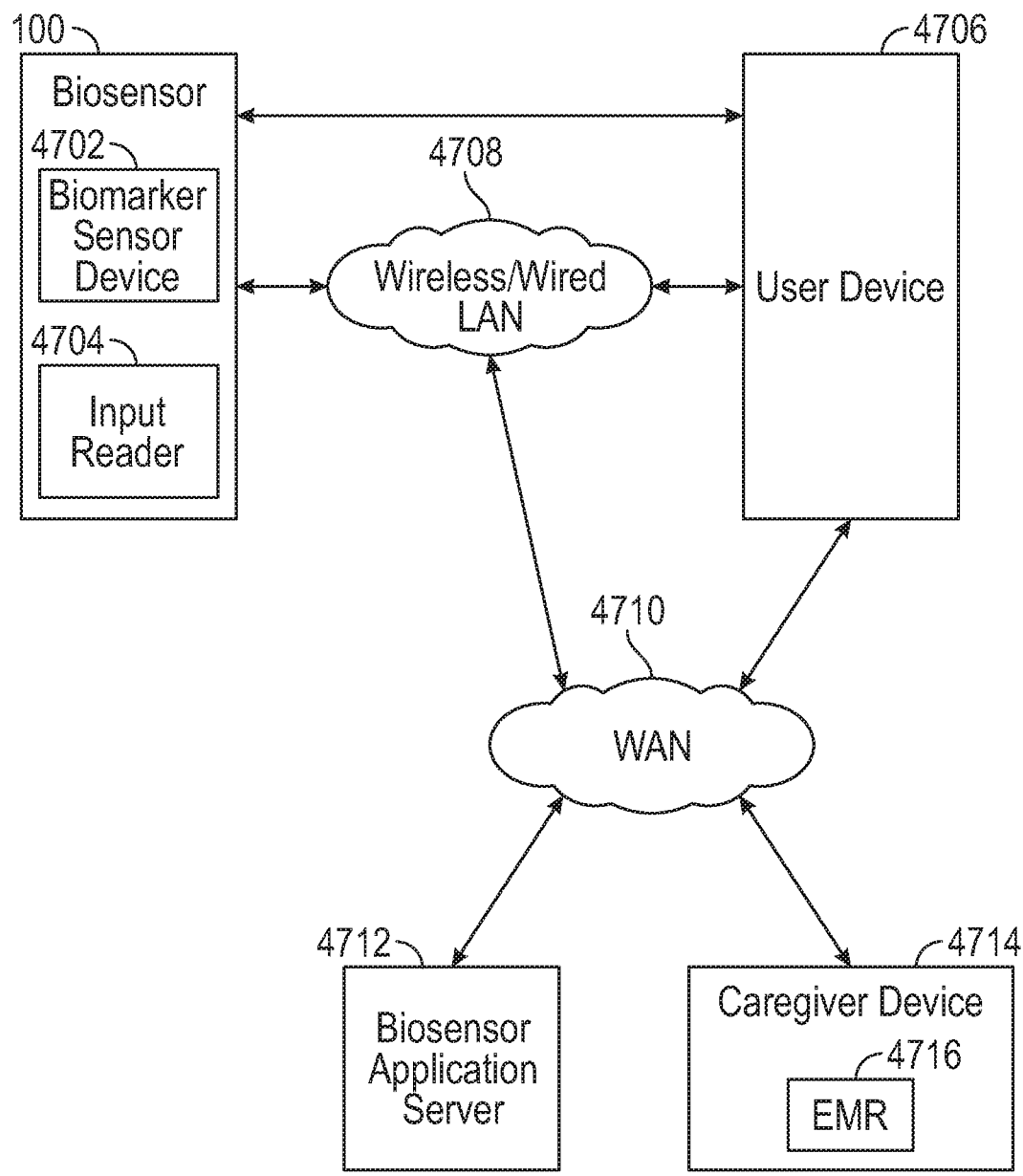
FIG. 47 illustrates a schematic block diagram of an embodiment of the biosensor with another biomarker sensor device.

FIG. 47 illustrates a schematic block diagram of an embodiment of the biosensor 100 with another biomarker sensor device 4702. The biosensor 100 may include or be incorporated with or communicate with one or more other types of sensor devices. In one embodiment, the biosensor 100 is configured to include a biomarker sensor device 4702 that analyzes fluid samples from a patient. For example, the patient may test saliva, blood, urine or other fluid onto a chip or test strip. The input reader 4704 receives the fluid samples, e.g. on a chip or test strip. The biomarker sensor device 4702 may perform one or more tests to detect conditions of the patient.

In one example, a test for infection such as COVID-19 is incorporated into the biosensor 100. A patient swabs a throat and rinses the swab in a test liquid. The test liquid is inserted into a chip for insertion into the input reader 4704. The biosensor 100 may perform tests on the chip to determine a presence of an infection.

The biosensor 100 may communicate over a wired or wireless local area network 4708 to a user device 4706. In another embodiment, the biosensor 100 may communicate directly with the user device 4706 using Bluetooth, RFID or other short range communication. The user device 4708 and/or biosensor 100 may communicate over a wide area network (WAN) 4710 to a biosensor application server 4712. The biosensor application server 4712 may collect data of a plurality of users for modeling of the data and determination of infections in geographical areas and determining demographic data of infections. The biosensor 100 may also communicate patient data to a caregiver device 4714. The patient data may be stored in an electronic medical record (EMR) 4716.

In one or more aspects herein, a processing module or circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. A biosensor, comprising:
a photoplethysmography (PPG) circuit configured to obtain at least a first PPG signal from light reflected from or transmitted through skin tissue of a patient, wherein the light includes a first wavelength in a range of 380 nm to 410 nm; and
a processing circuit configured to:
obtain a measurement of nitric oxide (NO) level in blood flow using at least the first PPG signal;
determine an infection present in the patient using the measurement of the NO level in blood flow; and
generate an indication of the infection.

2. The biosensor of claim 1, wherein the processing circuit is further configured to generate a severity level of the infection in the patient.

3. The biosensor of claim 1, wherein the processing circuit is further configured to determine a heart rate and respiration of the patient using the first PPG signal and generate the indication of the infection in the patient using the measurement of NO and the heart rate and the respiration rate.

4. The biosensor of claim 1, further comprising:
a temperature sensor configured to measure a skin temperature of the patient; and
wherein the processing circuit is further configured to determine the infection in the patient using the measurement of NO and the skin temperature of the patient.

5. The biosensor of claim 1, wherein the optical circuit is configured to obtain a plurality of PPG signals at a plurality of different wavelengths reflected from tissue of a user, wherein the plurality of different wavelengths have varying penetration depths of tissue, wherein one of the plurality of PPG signals is the first PPG signal.

6. The biosensor of claim 5, wherein the processing circuit is further configured to:
determine a plurality of L values using the plurality of PPG signals, wherein each of the plurality of L values is determined by isolating an alternating current (AC) component of a different one of the plurality of PPG signals;
determine a plurality of R values using the plurality of L values, wherein each of the plurality of R values is determined using a ratio of two L values of the plurality of L values; and
determine the infection in the patient using the plurality of L values and the plurality of R values.

7. The biosensor of claim 6 wherein the processing circuit is further configured to:
determine one or more other PPG parameters using the plurality of PPG signals;
determine the infection in the patient using the plurality of L values, the plurality of R values and the one or more other PPG parameters.

8. The biosensor of claim 7, wherein the one or more other PPG parameters include at least one of: a phase delay between the first PPG signal and a second PPG signal of the plurality of additional PPG signals, a correlation of phase shape between the first PPG signal and the second PPG signal or a periodicity of first PPG signal or the second PPG signal.

9. The biosensor of claim 7, wherein the processing circuit is configured to determine a confidence level in the indication of infection in the patient using the plurality of L values, the plurality of R values and the one or more other PPG parameters.

10. The biosensor of claim 7, wherein the processing circuit is further configured to determine a type of the infection using the plurality of L values, the plurality of R values and the one or more other PPG parameters, wherein the type of infection includes at least one of: sepsis, COVID-19, pneumonia, or influenza.

11. The biosensor of claim 7, wherein the plurality of L values includes:
a first L value determined using the first PPG signal obtained at the first wavelength in a range of 380 nm-410 nm; and a second L value determined using a second PPG signal of the plurality of PPG signals, wherein the second PPG signal is obtained at a second wavelength equal to or above 660 nm.

12. The biosensor of claim 7, wherein the plurality of R values includes:
   an R value determined using the first PPG signal obtained at the first wavelength in a range of 380 nm-410 nm and the second PPG signal obtained at the second wavelength equal to or above 660 nm;
   an R value determined using the first PPG signal obtained at the first wavelength in the range of 380 nm-410 nm and a third PPG signal of the plurality of additional PPG signals, wherein the third PPG signal is obtained at a third wavelength in a range of 510 nm-550 nm; or
   an R value determined using the third PPG signal obtained at the third wavelength in the range of 510 nm-550 nm and the second PPG signal obtained at the second wavelength equal to or above 660 nm.

13. The biosensor of claim 7, wherein the processing circuit includes a neural network processing circuit, wherein the neural network processing device is pre-configured with a learning vector generated from a training set, wherein the training set includes the plurality of L values, the plurality of R values and the one or more other PPG parameters obtained from a plurality of patients diagnosed with the infection.

14. A biosensor, comprising:
   an optical circuit configured to obtain at least a first PPG signal from light reflected from skin tissue of a patient, wherein the light includes a first wavelength in an ultraviolet (UV) range and at least a second PPG signal from light reflected from skin tissue of the patient, wherein the light includes a second wavelength in an infrared (IR) range; and
   one or more processing circuits configured to:
      obtain a measurement of nitric oxide (NO) levels in blood flow using the first PPG signal and the second PPG signal, wherein the measurement of NO levels is an R value determined using a ratio of an AC component of the first PPG signal and an AC component of the second PPG signal;
      generate an indication of infection in the patient using at least the measurement of NO levels; and
      generate a severity level of the infection using at least the measurement of NO levels.

15. The biosensor of claim 14, wherein the one or more processing circuits is further configured to:
   determine a respiratory rate from the first or second PPG signals;
   determine an estimation of blood pressure from the first or second PPG signals; and
   determine a hybrid quick Sequential Organ Failure Assessment (qSOFA) score using the respiratory rate, the measurement of NO levels and the estimation of blood pressure.

16. The biosensor of claim 14, wherein the one or more processing circuits is further configured to:
   determine a heart rate and a respiration rate of the patient using one or more of the first PPG signal or the second PPG signal and generate the indication of the risk of infection in the patient using the measurement of NO and the heart rate and the respiration rate.

17. The biosensor of claim 16, further comprising:
   a temperature sensor configured to measure a skin temperature of the patient; and
   wherein the one or more processing circuits is further configured to generate the indication of the risk of infection in the patient using the measurement of NO, the heart rate, the respiration rate and the skin temperature of the patient.

18. The biosensor of claim 14, wherein the one or more processing circuits is further configured to:
   determine the R value using the first PPG signal obtained at the first wavelength in a range of 380 nm-400 nm and the second PPG signal obtained at the second wavelength equal to or above 660 nm; and
   generate the indication of the infection in the patient using the R value.

19. The biosensor of claim 18, wherein the one or more processing circuits is further configured to:
   determine a second R value using a third PPG signal obtained at a third wavelength in the range of 510 nm and 550 nm and the second PPG signal obtained at the second wavelength equal to or above 660 nm, wherein the second R value is a measurement of creatinine in blood flow; and
   generate the indication of the infection in the patient using the first R value for the measurement of NO levels in blood flow and the second R value for the measurement of creatinine in blood flow.

20. The biosensor of claim 19, wherein the one or more processing circuits is further configured to:
   determine a third R value using a fourth PPG signal obtained at a fourth wavelength in the range of 448 nm and 488 nm and the second PPG signal obtained at the second wavelength equal to or above 660 nm, wherein the third R value is a measurement of a liver enzyme P450 in blood flow; and
   generate the indication of the infection in the patient using the first R value for the measurement of NO levels in blood flow, the second R value for the measurement of creatinine in blood flow and the third R value for the measurement of the liver enzyme P450 in blood flow.

21. The biosensor of claim 14, wherein the one or more processing circuits is further configured to:
   determine a heart rate and respiratory rate from the first or second PPG signals;
   determine an estimation of blood pressure from the first or second PPG signals; and
   determine a hybrid quick Sequential Organ Failure Assessment (qSOFA) score using the respiratory rate, the heart rate, the estimation of blood pressure and the R value.

22. A biosensor, comprising:
   an optical circuit configured to obtain a plurality of PPG signals from light at a plurality of different wavelengths reflected from skin tissue of a patient, wherein at least a first PPG signal is obtained from a first wavelength in a range of 380 nm to 410 nm and at least a second PPG signal is obtained from a second wavelength in a range of 920 nm to 960 nm; and
   one or more processing devices configured to:
      obtain a first R value using the first PPG signal and the second PPG signal; and
      generate an indication of a severity of an infection in the patient using at least the first R value.

23. The biosensor of claim 22, wherein the one or more processing devices are further configured to:
   determine a heart rate using one or more of the plurality of PPG signals; and
   generate the indication of the severity of the infection in the patient using at least the first R value and the heart rate.

24. The biosensor of claim 23, wherein the one or more processing devices are further configured to:
- determine a second R value using a third PPG signal and the second PPG signal, wherein the third PPG signal is obtained from a third wavelength in a range of 510 nm to 550 nm; and
- generate the indication of the severity of the infection in the patient using at least the first R value, the second R value and the heart rate.

25. The biosensor of claim 24, wherein the one or more processing devices are further configured to:
- determine a third R value using the third PPG signal and a fourth PPG signal, wherein the fourth PPG signal is obtained from a fourth wavelength at 660 nm; and
- generate the indication of the severity of the infection in the patient using at least the first R value, the second R value, the third R value and the heart rate.

26. The biosensor of claim 25, wherein the one or more processing devices are further configured to:
- determine a measurement of a time difference between the first PPG signal and the second PPG signal; and
- generate the indication of the severity of the infection in the patient using at least the first R value, the second R value, the third R value, the measurement of the time difference and the heart rate.

27. The biosensor of claim 26, wherein the one or more processing devices are further configured to:
- determine a measurement of oxygen saturation, wherein the measurement includes a fourth R value determined from the fourth PPG signal obtained from the fourth wavelength at 660 nm and from the second PPG signal obtained from the second wavelength in the range of 920 nm to 960 nm; and
- generate the indication of the severity of the infection in the patient using at least the first R value, the second R value, the third R value, the fourth R value, the measurement of the time difference and the heart rate.

28. The biosensor of claim 27, wherein the one or more processing devices includes at least one neural network processing device.

* * * * *